US008835628B2

(12) United States Patent
Mauduit et al.

(10) Patent No.: US 8,835,628 B2
(45) Date of Patent: Sep. 16, 2014

(54) STABLE AND HIGHLY TUNABLE METATHESIS CATALYSTS

(75) Inventors: Marc Mauduit, Vitré (FR); Frédéric Caijo, Thorigné Fouiliard (FR); Christophe Crevisy, Pont-Péan (FR)

(73) Assignees: Ecole Nationale Superieure de Chimie de Rennes, Rennes Cedex (FR); Centre National de la Recherche Scientifique CNRS, Paris Cedex (FR)

( * ) Notice: Subject to any disclaimer, the term of this patent is extended or adjusted under 35 U.S.C. 154(b) by 0 days.

(21) Appl. No.: 13/813,397

(22) PCT Filed: Jul. 30, 2010

(86) PCT No.: PCT/EP2010/004668
§ 371 (c)(1), (2), (4) Date: Apr. 12, 2013

(87) PCT Pub. No.: WO2012/013208
PCT Pub. Date: Feb. 2, 2012

(65) Prior Publication Data
US 2013/0197218 A1 Aug. 1, 2013

(51) Int. Cl.
*C07D 207/20* (2006.01)
*B01J 31/12* (2006.01)

(52) U.S. Cl.
USPC .............................. 544/64; 548/565; 560/122

(58) Field of Classification Search
USPC .............................. 544/64
See application file for complete search history.

(56) References Cited

U.S. PATENT DOCUMENTS

2010/0113795 A1 5/2010 Arlt et al.

FOREIGN PATENT DOCUMENTS

| | | | |
|---|---|---|---|
| WO | WO 02/14376 | A2 | 2/2002 |
| WO | WO 2004/035596 | A1 | 4/2004 |
| WO | WO 2007/003135 | A1 | 1/2007 |
| WO | WO 2008/046106 | A2 | 4/2008 |
| WO | WO 2008/065187 | A1 | 6/2008 |

OTHER PUBLICATIONS

Wakamatsu, Hideaki et al., *A New Highly Efficient Ruthenium Metathesis Catalyst*, Communications, Angew. Chem. Int. Ed. 2002, 41, No. 13, 2403-2405, 3 pages.

Clavier, Herve et al., *Towards Long-Living Metathesis Catalysts by Tuning the N-Heterocyclic Carbene (NHC) Ligand on Trifluoroacetamide-Activated Boomerang Ru Complexes*, Full Paper, Euro. J. Org. Chem. 2009, 4254-4265, 12 pages.

Love, Jennifer A., et al., *A Practical and Highly Active Ruthenium-Based Catalyst that Effects the Cross Metathesis of Acrylonitrile*, Communications, Agnew. Chem. Int. Ed. 2002, 41, No. 21, 4035-4038, 3 pages.

Schrock, Richard R., et al., *Synthesis of Molybdenum Imido Alkylidene Complexes and Some Reactions Involving Acyclic Olefins*, J. Am. Chem. Soc. 1990, 112, 3875-3886, 12 pages.

Barbasiewicz, Michal et al., *Probing of the Ligand Anatomy: Effects of the Chelating Alkoxy Ligand Modifications on the Structure and Catalytic Activity of Ruthenium Carbene Complexes*, Full Papers, Adv. Synth. Catal. 2007, 349, 193-203, 11 pages.

Grela, Karol, et al., *A Highly Efficient Ruthenium Catalyst for Metathesis Reactions*, Communications, Angew. Chem. Int. Ed. 2002, 41, No. 21, 4038-4040, 3 pages.

Garber, Steven B. et al., *Efficient and Recyclable Monomeric and Dendritic Ru-Based Metathesis Catalysts*, J. Am. Chem. Soc. 2000, 122, 8168-8179, 12 pages.

Wakamatsu, Hideaki, et al., *A Highly Active and Air-Stable Ruthenium Complex for Olefin Metathesis*, Angew. Chem. Int. Ed. 2002, 41, No. 5, 794-796, 3 pages.

Romero, Patricio E., et al., *Rapidly Initiating Ruthenium Olefin-Metathesis Catalysts*, Olefin Metathesis, Angew. Chem. Int. Ed. 2004, 43, 6161-6165, 2 pages.

Michrowska, Anna, et al., *Nitro-Substituted Hoveyda-Grubbs Ruthenium Carbenes: Enhancement of Catalyst Activity through Electronic Activation*, J. Am. Chem. Soc. 2004, 126, 9318-9325, 8 pages.

Hryniewicka, Agnieszka, et al., *New efficient ruthenium metathesis catalyst containing chromenyl ligand*, Journal of Organometallic Chemistry, ScienceDirect, 695 (2010), 1265-1270, 6 pages.

Rix, Diane, et al., *Aminocarbonyl Group Containing Noveyda-Grubbs-Type Complexes: Synthesis and Activity in Olefin Metathesis Transformations*, JOC Notes, J. Org. Chem. 2008, 73, 4225-4228, 4 pages.

International Search Report dated Oct. 27, 2010, issued in PCT/EP2010/004668; 2 pages.

Bienick, Michael et al., *Advanced Fine-Tuning of Grubbs/Hoveyda Olefin Metathesis Catalysts: A Further Step Toward an Optimum Balance Between Antinomic Properties*, J. Am. Chem. Soc. 2006, 128, pp. 13652-13653.

*Primary Examiner* — Kahsay Habte
(74) *Attorney, Agent, or Firm* — Christie, Parker & Hale, LLP

(57) ABSTRACT

The present invention relates to catalytically active compounds of the general formula (1) that are highly tunable, as well as to a method of their preparation and their use in any type metathesis reaction. The new compounds of the present invention comprise activation sites that allow for specific catalyst design. Particularly, side chains and ligands allow efficient activity and specificity control of the catalysts of the present invention.

(1)

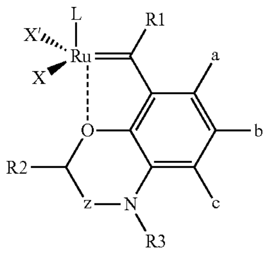

40 Claims, 6 Drawing Sheets

STABLE AND HIGHLY TUNABLE METATHESIS CATALYSTS

CROSS-REFERENCE TO RELATED APPLICATION

This application is a National Phase Patent Application and claims the priority of International Application Number PCT/EP2010/004668 filed on Jul. 30, 2010.

The present invention concerns novel ruthenium compounds and the use thereof as catalyst in olefin metathesis reactions. The present invention also concerns a method for the preparation of said ruthenium compounds.

Ruthenium compounds or complexes, as well as their use as catalysts are well known in prior art. Methods for their preparation are vastly studied and can be found in a great number of scientific publications.

For instance, the compounds called Grubbs III, Schrock catalyst, Piers-Grubbs II are well known as highly active catalysts for olefins metathesis and are respectively described in the following scientific publications: *Angew. Chem. Int. Ed.* 2002, 41, 4035-4038*; J. Am. Chem. Soc.* 1990, 112, 3875-3886*; Angew. Chem. Int. Ed.,* 2004, 43, 6161-6165.

The ruthenium complex of the formula A, known as Hoveyda-Grubbs catalyst, is disclosed in WO 02/14376 A2 and in the original paper: *J. AM. CHEM. SOC.,* 2000, 122, 8168-8179.

(A)

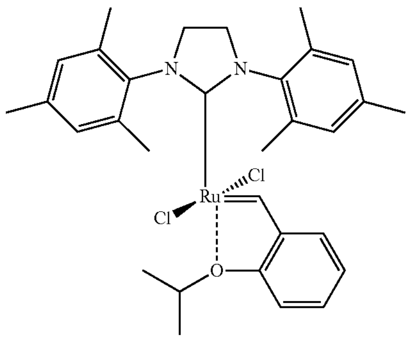

The Hoveyda-Grubbs catalyst is considered in prior art as an active, air stable and recoverable metathesis catalyst. In order to enhance and improve the activity towards olefin metathesis transformations, several structural modifications have been achieved through the styrenylether benzylidene ligand.

These structural modifications have led to other well-known catalysts, showing a higher catalytic activity than the classic Hoveyda-Grubbs catalyst of formula A.

For instance, WO 2004/035596, *Angew. Chem. Int. Ed.* 2002, 41, 4038-4040 and *J. Am. Chem. Soc.* 2004, 126, 9318-9325 disclose a catalyst of formula B (also referred to as Grela catalyst):

(B)

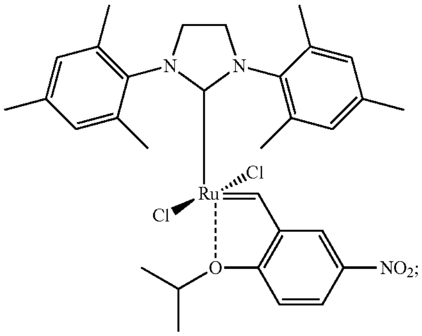

WO 2007/003135 discloses a catalyst of formula C (also referred to as Zannan catalyst):

(C)

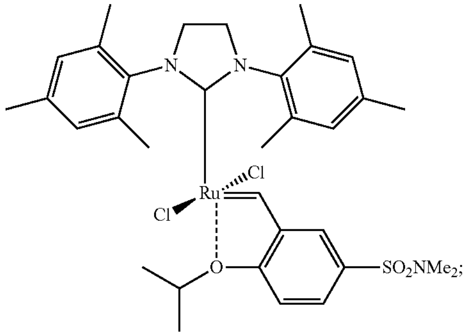

WO 2008/065187 A1 and *Eur. J. Org. Chem.* 2009, 4254-4265 disclose a catalyst of formula D:

(D)

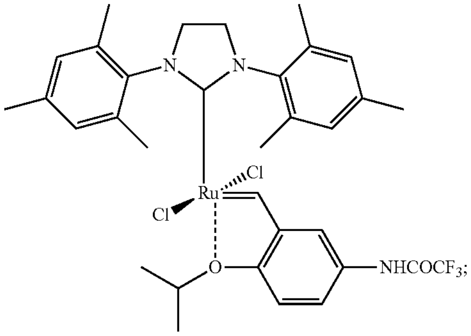

*Angew. Chem. Int. Ed.* 2002, 41, 794-796 discloses a catalyst of formula E:

(E)

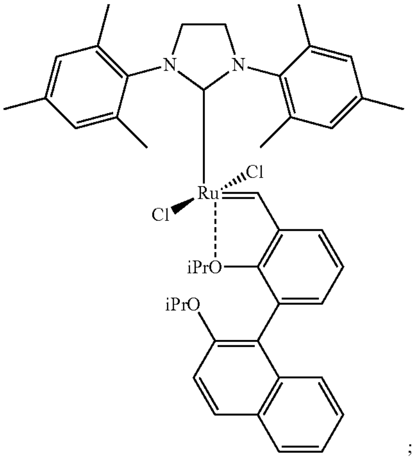

;

*Angew. Chem. Int. Ed.* 2002, 41, 2403-2405 discloses a catalyst of formula F (also referred to as Blechert catalyst), (F)

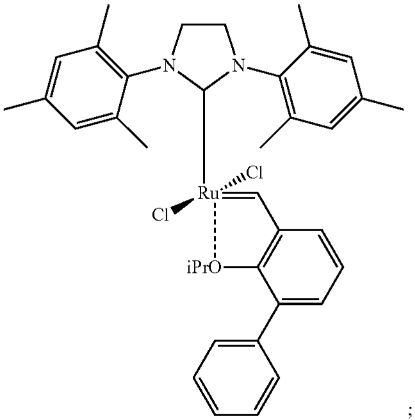

;

*J. Am. Chem. Soc.* 2006, 128, 13652-13653 discloses a catalyst of formula G:

(G)

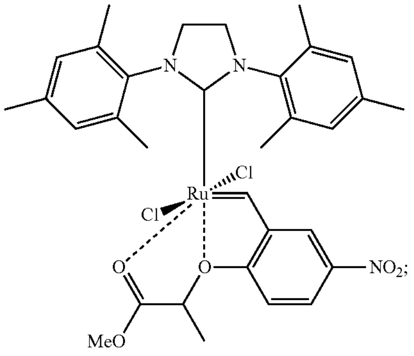

US 2010/0113795 A1 discloses a catalyst of formula H:

(H)

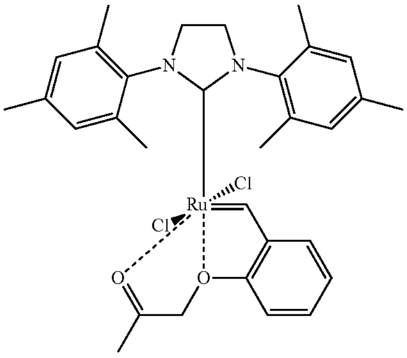

;

*Adv. Synth. Catal.* 2007, 349, 193-203 discloses a catalyst of formula I:

(I)

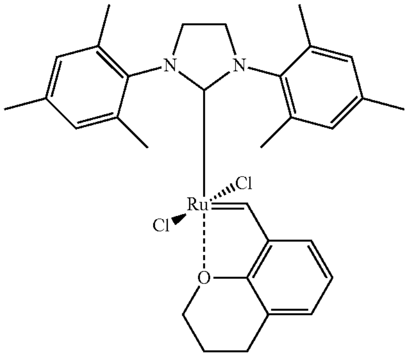

;

and

*J. Organomet. Chem.* 2010, 695, 1265-1270 discloses a catalyst of formula J:

(J)

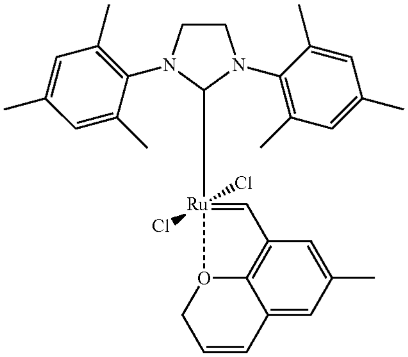

.

The improvement in the activity of B, C, D compared to A is attributed to the electronic effects of the substituents on the styrenylether benzylidene ligand (respectively $NO_2$, $SO_2NMe_2$ and $NHCOCF_3$).

The improvement in the activity of E and F compared to A is attributed to the steric effects of the ortho-substituents on the styrenylether benzylidene ligand (respectively a naphtol and a phenyl).

The improvement in the activity of G and H compared to A is attributed to the additional coordinating functions on the styrenylether benzylidene ligand (respectively an ester and a ketone). An additional electronic effect can be involved, as showed in G with a $NO_2$ substituent.

The improvement in the activity of I and J compared to A is attributed to the conformational constraints of the chelating ether into the styrenylether benzylidene ligand (respectively a chroman and chromenyl ring).

One between other problems of prior art catalysts is that catalytic activity goes along with complex instability. In fact, generally the more a catalyst is active the less said catalyst is stable.

The present invention improves the situation.

For this purpose, the invention proposes ruthenium compounds having a novel backbone structure.

In fact, the applicant surprisingly found that ruthenium compounds comprising an oxazinone or oxazine function in their backbone show a significant activity increase compared to prior art catalysts such as those of formula A, B, C, D, E, F, G, H, I or J.

The oxazinone or oxazine function is set as new coordinating alkoxy ligand into the benzylidene fragment of the prior art catalysts.

Moreover, in the present invention the applicant identified three different activation sites within the new chelating benzylidene ligand. These activation sites allow efficient and specific control of the catalytic activity of the ruthenium complexes in olefin metathesis transformation.

Further, the improvement of the catalytic activity does not occur at the detriment of the complex stability. Indeed, the complex of the invention remains remarkably stable towards moisture, air and solvents.

To this end, the invention proposes compound of the general formula 1, (1)

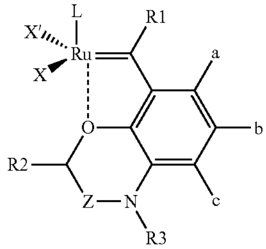

wherein,

- X and X' are anionic ligands;
- L is an uncharged ligand;
- z is a methylene or a carbonyl group;
- a, b and c are each, independently of one another, H, or a substituted or unsubstituted, charged or uncharged side chain comprising up to 20 carbon atoms and optionally comprising one or more functional groups;
- R1, R2 and R3 are each, independently of one another, H or a substituted or unsubstituted, charged or uncharged side chain comprising up to 20 carbon atoms and optionally comprising one or more functional groups.

When z is carbonyl, general formula 1 can be represented by following formula $1^a$; and when z is methylene general formula 1 can be represented by following formula $1^b$.

($1^a$)

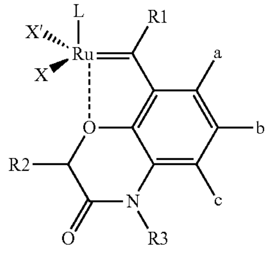

($1^b$)

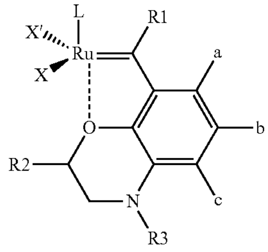

Preference is given here to the compounds of general formula 1 in which X and X' are halogen and particularly to the compounds in which said halogen are selected from the group consisting of Cl and Br.

In the above mentioned compounds of general formula 1, preference is given to those in which a, b and c are each selected from the group consisting of H; $—NO_2$; $C_{1-12}$-alkyl; $C_{5-12}$-cycloalkyl; $C_{1-12}$-alkoxy; cyano; aryl or heteroaryl, preferentially phenyl optionally substituted by a radical selected from the group consisting of $C_{1-6}$-alkyl and $C_{1-6}$-alkoxy; monohalogenated or polyhalogenated aryl radicals or hetero-aryl radicals; monohalogenated or polyhalogenated $C_{1-6}$-alkyl radicals; monohalogenated or polyhalogenated $C_{1-6}$-alkyl-substituted aryl radicals; $C_{1-6}$-alkylcarbonyl radicals; monohalogenated or polyhalogenated $C_{1-6}$-alkylcarbonyl radicals; $C_{1-6}$-alkoxycarbonyl radicals; monohalogenated or polyhalogenated $C_{1-6}$-alkoxycarbonyl radicals; arylcarbonyl radicals; monohalogenated or polyhalogenated arylcarbonyl radicals; aryloxycarbonyl radicals; monohalogenated or polyhalogenated aryloxycarbonyl radicals; $—(C{=}O)—N(R^a)_2$ radicals wherein $R^a$ is a $C_{1-6}$-alkyl or aryl radical; $—NH—(C{=}O)—R^a$ radicals wherein $R^a$ is a $C_{1-6}$-alkyl or aryl radical; $C_{1-6}$-alkylsulfonyl radicals; $C_{1-6}$-alkylsulfinyl radicals; $—P({=}O)(R^a)_2$ radicals wherein $R^a$ is a $C_{1-6}$-alkyl or aryl radical; $—NH—SO_2—R^a$ radicals wherein $R^a$ is a $C_{1-6}$-alkyl or aryl radical; $(SO_2)NR^a_2$ radicals wherein $R^a$ is a $C_{1-6}$-alkyl or aryl radical; $P({=}O)(OR^a)(R^a)$ radicals wherein $R^a$ is a $C_{1-6}$-alkyl or aryl radical.

In a particular preferred embodiment a, b and c are each H.

Further, preference is given here to the compounds of general formula 1 in which R1 is selected from the group consisting of H, $C_{2-12}$-alkenyl, $C_{2-12}$-alkynyl or aryl.

In a particular preferred embodiment R1 is H.

Furthermore, preference is given here to the compounds of general formula 1 in which R2 is selected from the group consisting of H, $C_{1-12}$-alkyl, $C_{5-12}$-cycloalkyl, $C_{7-18}$-aralkyl or aryl.

In a particular preferred embodiment R2 is a methyl-, ethyl- or isopropyl-group.

Furthermore, preference is given to the compounds of general formula 1 in which R3 is selected from the group consisting of H, $C_{1-12}$-alkyl, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyl, nitrile or a radical selected from the group consisting of ketones COR4, esters $CO_2R4$, oxalates $COCO_2R4$, sulfones $SO_2R4$ or amides CONHR4 wherein R4 is selected from the group consisting of H, $C_{1-12}$-alkyl, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyle, nitrile.

Particular preference is given to the compounds of general formula 1 in which z is methylene, and R3 is a side chain of following formula $R3^a$ or $R3^b$:

($R3^a$)

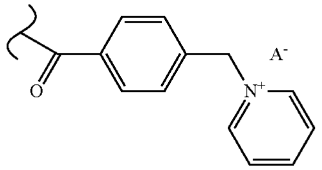

-continued (R3$^b$)

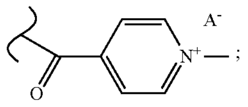

in this preferred embodiment, $A^-$ is selected from the group consisting of $F^-$, $Cl^-$, $Br^-$, $I^-$, tetrafluoroborate $BF_4^-$, hexafluorophosphate $PF_6^-$ and bis(trifluoromethylsulfonyl) amide $NTf_2^-$.

In another preferred embodiment, R3 is a side chain of following formula R3$^c$, R3$^d$, R3$^e$, R3$^f$, R3$^g$, R3$^h$, R3$^i$, R3$^j$, R3$^k$, R3$^l$, R3$^m$, R3$^n$, R3$^o$ or R3$^p$:

(R3$^c$)

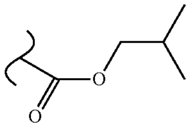

(R3$^d$)

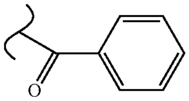

(R3$^e$)

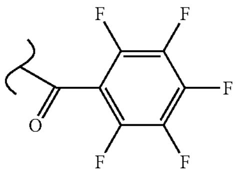

(R3$^f$)

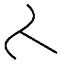

(R3$^g$)

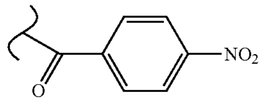

(R3$^h$)

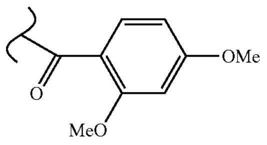

(R3$^i$)

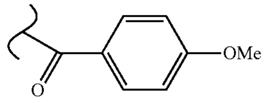

(R3$^j$)

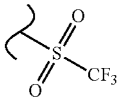

(R3$^k$)

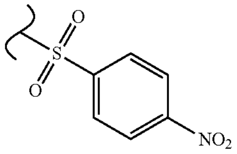

-continued (R3$^l$)

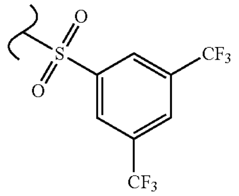

(R3$^m$)

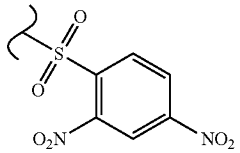

(R3$^n$)

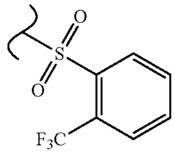

(R3$^o$)

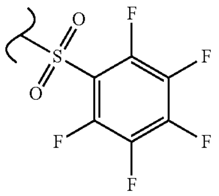

(R3$^p$)

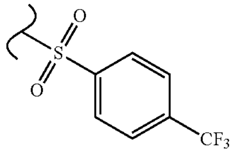

Preference is given to the compounds of general formula 1 in which L is a phosphine $P(R8)_3$ or a phosphate $P(OR9)_3$ and wherein R8 and R9 are each independently of one another $C_{1-6}$-alkyl, $C_{5-12}$-cycloalkyl or aryl.

Another preference is given to the compounds of general formula 1 in which L is a ligand of following formula L1, L2, L3 or L4:

(L1)

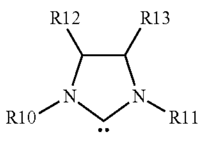

(L2)

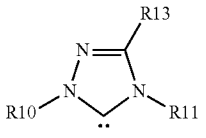

(L3)

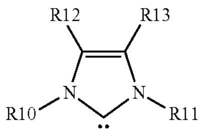

-continued (L4)

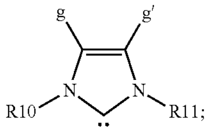

in this embodiment, R10 and R11 are each, independently of one another a substituted or an unsubstituted side chain comprising 1 to 30 carbon atoms and optionally comprising one or more functional groups. Further, in this embodiment R12 and R13 are each, independently of one another, H, $C_{1-6}$-alkyl optionally substituted by a alkoxy radical OR15, or aryl optionally substituted by a alkoxy radical OR15, or form a 3- or 4-membered alkylene bridge, and wherein R15 is selected from the group consisting of $C_{1-20}$-alkyl, aryl and $C_{7-18}$-aralkyl, and wherein g and g' are each halogen. In a particular preferred embodiment g and g' are either Cl or Br atoms.

Furthermore, in the above mentioned embodiment, particular preference is given to the compounds in which R10 and R11 are each, independently of one another, $C_{1-30}$-alkyl optionally substituted by a alkoxy radical OR15, $C_{2-30}$-alkenyl optionally substituted by a alkoxy radical OR15, aryl optionally substituted by a alkoxy radical OR15, aminoalkyl or aminocycloalkyl.

Particular preference is given to the compounds of general formula 1 in which L is a ligand of following formula $L1^a$, $L1^b$, $L1^c$, $L1^d$, $L1^e$, $L1^f$ or $L1^g$:

($L1^a$)

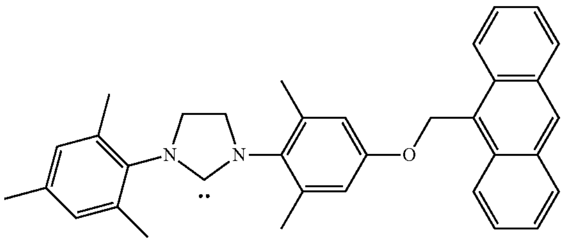

($L1^b$)

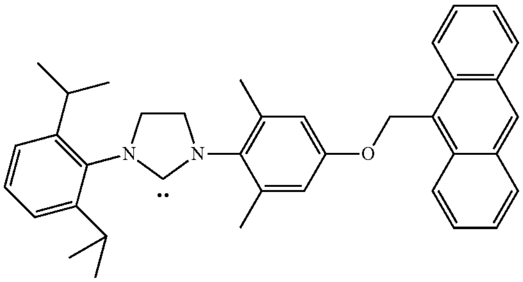

($L1^c$)

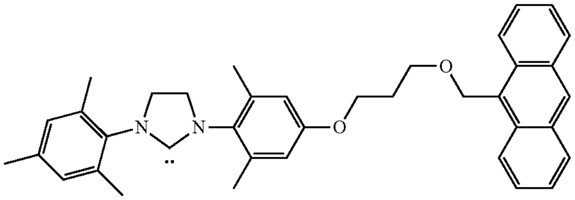

-continued ($L1^d$)

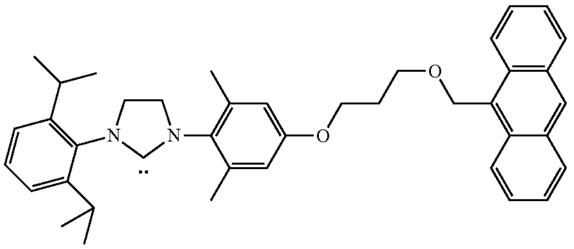

($L1^e$)

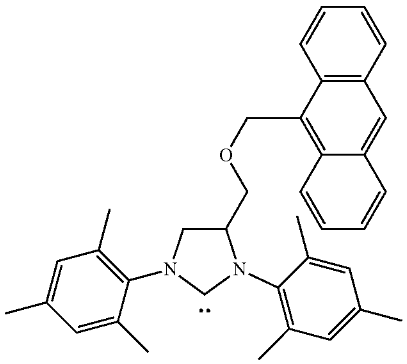

($L1^f$)

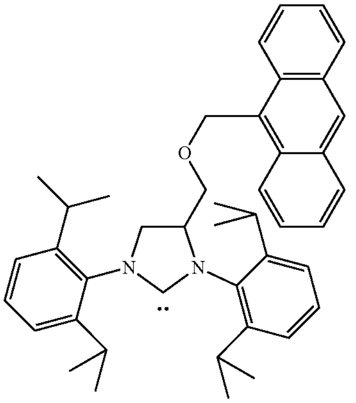

($L1^g$)

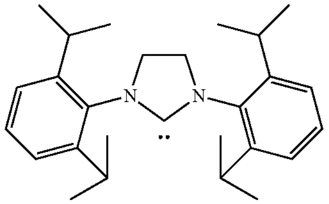

An additional aspect of the present invention is the use of the compound described above as a catalyst for a chemical reaction. More particularly, said chemical reaction is a metathesis reaction such as ring-closing metathesis (RCM), cross-metathesis (CM) and ring-opening metathesis polymerization (ROMP).

An additional aspect of the present invention is a method for preparing the new compounds of general formula 1 disclosed hereinabove. The method of the present invention comprises a step of reacting a compound of the below general formula (2) with a ruthenium complex of the below general formula (3):

(2)

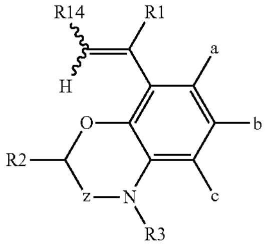

(3)

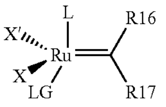

wherein

X and X' are anionic ligands;

L is an uncharged ligand;

z is a methylene or a carbonyl group;

a, b and c are each, independently of one another, H, or a substituted or unsubstituted, charged or uncharged side chain comprising up to 20 carbon atoms and optionally comprising one or more functional groups;

R1, R2 and R3 are each, independently of one another, H or a substituted or unsubstituted, charged or uncharged side chain comprising up to 20 carbon atoms and optionally comprising one or more functional groups, and wherein, LG is a leaving group, preferentially LG is a phosphine $P(R8)_3$ wherein R8 is selected from the group consisting of $C_{1-6}$-alkyl; $C_{5-12}$-cycloalkyl preferentially cyclohexyl; aryl; more preferentially LG is a pyridine wherein pyridine is unsubstituted or substituted by a charged or uncharged side chain comprising up to 20 carbon atoms, R14 is selected from the group consisting of H; $C_{1-12}$-alkyl, preferentially a methyl group; $C_{5-12}$-cycloalkyl, R16 and R17 are each independently of one another H, $C_{1-6}$-alkyl, optionally substituted by one or more halogens or by aryl, optionally substituted by one or more halogens or by $C_{1-6}$-alkyl; or R16 and R17 form together a 5- to 12-membered aliphatic and/or aromatic ring system, optionally substituted by one or more halogens, $C_{1-6}$-alkyl or by aryl; and preferentially R16 and R17 form an indenylidene system.

Preference is given here to the method in which X and X' are halogen. In this embodiment, X and X' are preferably selected from the group consisting of Cl and Br.

Further, preference is given to the method in which, a, b and c are each selected from the group consisting of H; —$NO_2$; $C_{1-12}$-alkyl; $C_{5-12}$-cycloalkyl; $C_{1-12}$-alkoxy; cyano; aryl or heteroaryl, preferentially phenyl optionally substituted by a radical selected from the group consisting of $C_{1-6}$-alkyl and $C_{1-6}$-alkoxy; monohalogenated or polyhalogenated aryl radicals or hetero-aryl radicals; monohalogenated or polyhalogenated $C_{1-6}$-alkyl radicals; monohalogenated or polyhalogenated $C_{1-6}$-alkyl-substituted aryl radicals; $C_{1-6}$-alkylcarbonyl radicals; monohalogenated or polyhalogenated $C_{1-6}$-alkylcarbonyl radicals; $C_{1-6}$-alkoxycarbonyl radicals; monohalogenated or polyhalogenated $C_{1-6}$-alkoxycarbonyl radicals; arylcarbonyl radicals; monohalogenated or polyhalogenated arylcarbonyl radicals; aryloxycarbonyl radicals; monohalogenated or polyhalogenated aryloxycarbonyl radicals; —(C═O)—$N(R^a)_2$ radicals wherein $R^a$ is a $C_{1-6}$-alkyl or aryl radical; —NH—(C═O)—$R^a$ radicals wherein $R^a$ is a $C_{1-6}$-alkyl or aryl radical; $C_{1-6}$-alkylsulfonyl radicals; $C_{1-6}$-alkylsulfinyl radicals; —$P(═O)(R^a)_2$ radicals wherein $R^a$ is a $C_{1-6}$-alkyl or aryl radical; —NH—$SO_2$—$R^a$ radicals wherein $R^a$ is a $C_{1-6}$-alkyl or aryl radical; $(SO_2)NR^a_2$ radicals wherein $R^a$ is a $C_{1-6}$-alkyl or aryl radical; $P(═O)(OR^a)(R^a)$ radicals wherein $R^a$ is a $C_{1-6}$-alkyl or aryl radical.

Particular preference is given to the method in which a, b and c are each H.

Another preference is given to the method in which R1 is selected from the group consisting of H, $C_{2-12}$-alkenyl, $C_{2-12}$-alkynyl or aryl.

Particular preference is given to the method in which R1 is H.

Another preference is given to the method in which R2 is selected from the group consisting of H, $C_{1-12}$-alkyl, $C_{5-12}$-cycloalkyl, $C_{7-18}$-aralkyl or aryl.

Particular preference is given to the method in which R2 is a methyl-, ethyl- or isopropyl-group.

Another preference is given to the method in which R3 is selected from the group consisting of H, $C_{1-12}$-alkyl, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyle, nitrile or a radical selected from the group consisting of ketones COR4, esters $CO_2R4$, oxalates $COCO_2R4$, sulfones $SO_2R4$ or amides CONHR4 wherein, R4 is selected from the group consisting of H, $C_{1-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyle, nitrile.

In a preferred embodiment of the method, z is methylene, and R3 is a side chain of following formula $R3^a$ or $R3^b$:

($R3^a$)

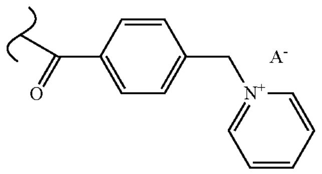

($R3^b$)

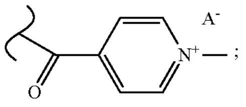

in this embodiment, $A^-$ is selected from the group consisting of $F^-$, $Cl^-$, $Br^-$, $I^-$, tetrafluoroborate $BF_4^-$, hexafluorophosphate $PF_6^-$ and bis(trifluoromethylsulfonyl)amide $NTf_2^-$.

Another preferred embodiment of the method, R3 is a side chain of following formula $R3^c$, $R3^d$, $R3^e$, $R3^f$, $R3^g$, $R3^h$, $R3^i$, $R3^j$, $R3^k$, $R3^l$, $R3^m$, $R^n$, $R3^o$ or $R3^p$:

($R3^c$)

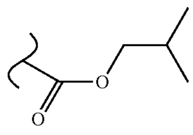

($R3^d$)

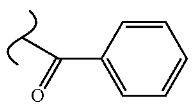

-continued ($R3^e$)

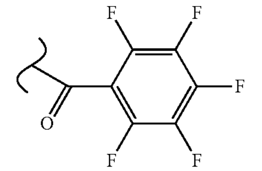

($R3^f$)

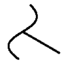

($R3^g$)

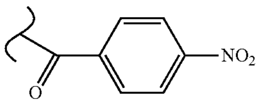

($R3^h$)

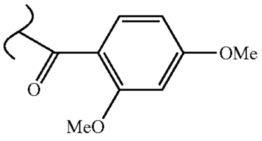

($R3^i$)

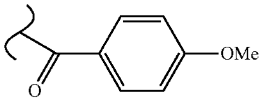

($R3^j$)

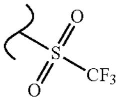

($R3^k$)

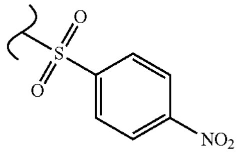

($R3^l$)

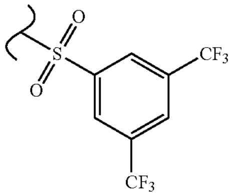

($R3^m$)

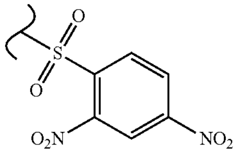

($R3^n$)

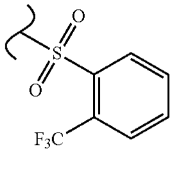

-continued ($R3^o$)

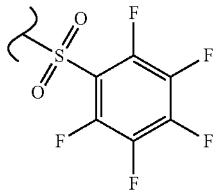

($R3^p$)

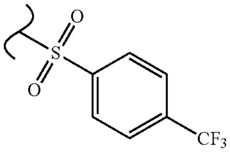

Preference is given to the method in which L is a phosphine $P(R8)_3$ or a phosphate $P(OR9)_3$ and wherein R8 and R9 are each independently of one another $C_{1-6}$-alkyl, $C_{5-12}$-cycloalkyl or aryl.

Another preference is given to the method in which L is a ligand of following formula L1, L2, L3 or L4:

(L1)

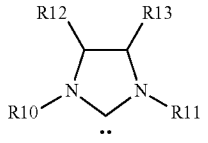

(L2)

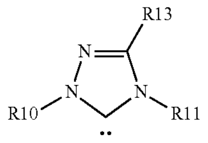

(L3)

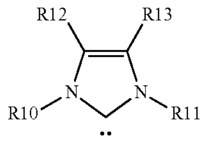

(L4)

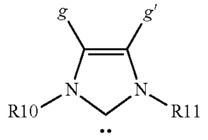

in this embodiment, R10 and R11 are each, independently of one another a substituted or an unsubstituted side chain comprising 1 to 30 carbon atoms and optionally comprising one or more functional groups. Further, in this embodiment R12 and R13 are each, independently of one another, H, $C_{1-6}$-alkyl optionally substituted by a alkoxy radical OR15, or aryl optionally substituted by a alkoxy radical OR15, or form a 3- or 4-membered alkylene bridge, and wherein R15 is selected from the group consisting of $C_{1-20}$-alkyl, aryl and $C_{7-18}$-aralkyl, and wherein g and g' are each halogen. In a particular preferred embodiment g and g' are either Cl or Br atoms.

Furthermore, in the above mentioned embodiment, particular preference is given to the method in which R10 and R11 are each, independently of one another, $C_{1-30}$-alkyl optionally substituted by a alkoxy radical OR15, $C_{2-30}$-alkenyl optionally substituted by a alkoxy radical OR15, aryl optionally substituted by a alkoxy radical OR15, aminoalkyl or aminocycloalkyl.

Another particular preference is given to the method in which L is a ligand of following formula L1$^a$, L1$^b$, L1$^c$, L1$^d$, L1$^e$, L1$^f$ or L1$^g$:

(L1$^a$)

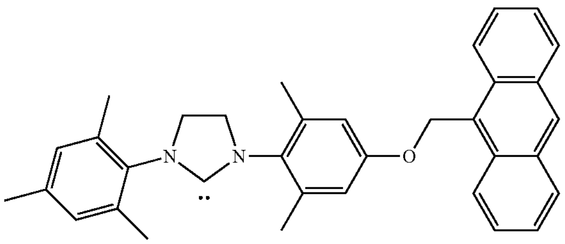

(L1$^b$)

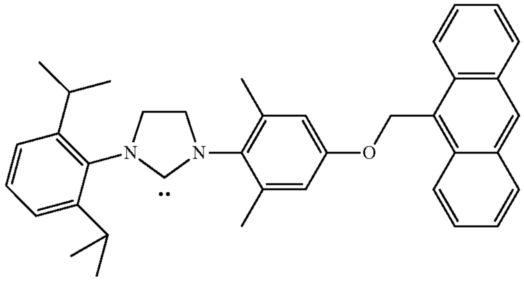

(L1$^c$)

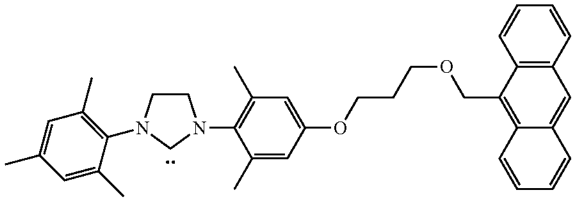

(L1$^d$)

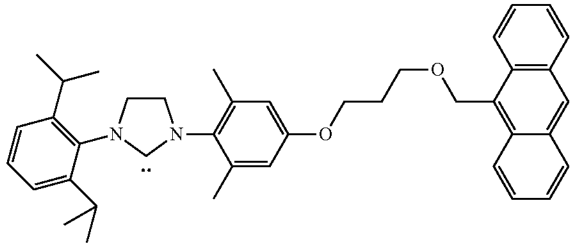

(L1$^e$)

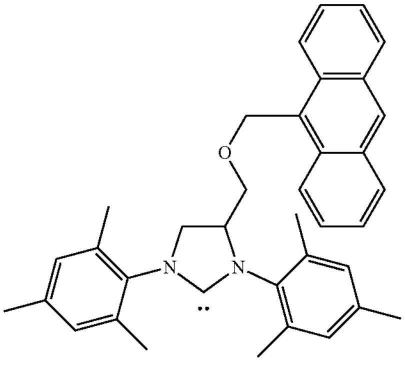

-continued (L1$^f$)

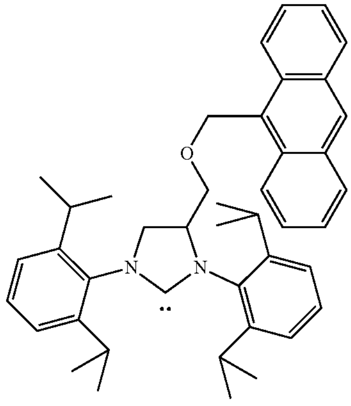

(L1$^g$)

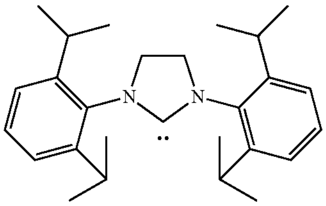

Other characteristics and advantages of the invention will become apparent upon examination of the upcoming description, examples and the accompanying drawings in which:

FIG. 1 is a graph showing the conversion rate over time of a product P60 into a product P61 a by metathesis reaction and in the presence of catalysts P32 and P41 according to the present invention, FIG. 2 is a graph showing the conversion rate over time of the product P60 into the product P61 a by metathesis reaction and in the presence of catalysts P33, P34, P35, P36 P37, P38, P39 and P40 according to the present invention, FIG. 3 is a graph showing the conversion rate over time of the product P60 into the product P61 a by metathesis reaction and in the presence of catalysts P42, P43, P44, P45 and P47 according to the present invention, FIG. 4 is a graph showing the conversion rate over time of the product P60 into the product P61 a by metathesis reaction and in the presence of catalysts P48, P49, P50 and P51 according to the present invention, FIG. 5 is a graph showing the conversion rate over time of the product P60 into the product P61 by a metathesis reaction and in the presence of catalysts P52, P53, P54, P55, P56 and P57 according to the present invention, FIG. 6 is a graph showing the conversion rate over time of the product P60 into the product P61 by metathesis reaction and in the presence of catalysts P58 and P59 according to the present invention, FIG. 7 is a graph showing the conversion rate over time of a product P62 into a product P63 by metathesis reaction and in the presence of four different prior art catalysts (Grubbs III, Schrock catalyst, Piers-Grubbs II and compound of formula G) in comparison with catalyst P34 according to the present invention, FIG. 8 is a graph showing the conversion rate over time of a product P64 into a product P65 by metathesis reaction and in the presence of three different prior art catalysts (Blechert, Umicore M71 SIPr of formula D, Grela of formula B, Zannan of formula C and compound of formula 1) in comparison with catalysts P33 and P34 according to the present invention, FIG. 9 is a stability graph showing the degradation rate over time of catalysts P33, P34, P35 and P37 according to the present invention, FIG. 10 is a stability graph showing the degradation rate over time of catalysts P42, P43, P44, P45 and P47 according to the present invention, FIG. 11 is a stability graph showing the degradation rate over time of catalysts P48, P49, P50, and P51 according to the present invention, and FIG. 12 is a stability graph showing the degradation rate over time of catalysts P52, P53, P54 and P55 according to the present invention.

The following description, examples and drawings contain elements of definite nature. They may therefore not only serve to explain and clarify the present invention, but also may serve to contribute to its definition, where appropriate.

Terminology and Definitions

For the purposes of the present invention, the term "anionic ligand" (X or X') refers to negatively charged molecules or atoms having electron donor properties. Examples which may be mentioned are halogens such as fluorine, chlorine, bromine or iodine.

For the purposes of the present invention, the term "uncharged ligand" (L) refers to uncharged or apparently charge-neutral molecules or atoms having electron donor properties. Examples which may be mentioned are tertiary phosphines containing aliphatic, cycloaliphatic and aromatic hydrocarbon radicals, e.g. trioctylphosphine, tridodecylphosphine, tricyclohexylphosphine, tris(2-methylcyclohexyl) phosphine and tris(o-tolyl)phosphine.

Particularly preferred uncharged ligands (L) are ligands such as the compounds described by the formulae:

(L1)

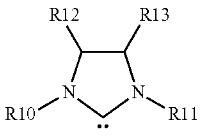

(L2)

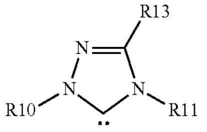

(L3)

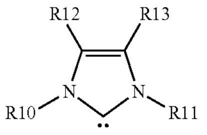

(L4)

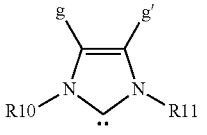

where R10 and R11 are each, independently of one another a substituted or an unsubstituted side chain comprising 1 to 30 carbon atoms and optionally comprising one or more functional groups, and where R12 and R13 are each, independently of one another, H, $C_{1-6}$-alkyl optionally substituted by a alkoxy radical OR15, or aryl optionally substituted by a alkoxy radical OR15, or form a 3- or 4-membered alkylene bridge, and where R15 is selected from the group consisting of C1-20-alkyl, aryl and C7-18-aralkyl, and where g and g' are each halogen, preferably Cl or Br As will be better understood while inspecting the catalyst examples according to the present invention, the ligand (L) is covalently bounded via the carbon atom marked with two dots (carbene radical) to the ruthenium (Ru) metal atom of the general formula 1 backbone.

The term "$C_{1-30}$-alkyl" refers (also when this is a constituent of other radicals) to branched and unbranched alkyl groups having from 1 to 30 carbon atoms. Correspondingly, the term "$C_{1-20}$-alkyl" refers to branched and unbranched alkyl groups having from 1 to 20 carbon atoms. The term "$C_{1-12}$-alkyl" refers to branched and unbranched alkyl groups having from 1 to 12 carbon atoms, the term "$C_{1-6}$-alkyl" refers to branched and unbranched alkyl groups having from 1 to 6 carbon atoms and the term "$C_{1-4}$-alkyl" refers to branched and unbranched alkyl groups having from 1 to 4 carbon atoms. Preference is given to alkyl groups having from 1 to 6 carbon atoms, particularly preferably from 1 to 4 carbon atoms. Examples which may be mentioned are: methyl, ethyl, n-propyl, isopropyl, n-butyl, isobutyl, sec-butyl, tert-butyl, n-pentyl, isopentyl, neopentyl and hexyl. The abbreviations Me, Et, n-Pr, i-Pr, n-Bu, i-Bu, t-Bu, etc., may also be used for the abovementioned groups. Unless indicated otherwise, in the case of propyl, butyl, pentyl and hexyl, the definitions encompass all conceivable isomeric forms of the respective radicals. Thus, for example, propyl encompasses n-propyl and isopropyl, butyl encompasses isobutyl, sec-butyl and tert-butyl, etc.

The term "$C_{1-12}$-ammonium-alkyl" refers to an alkyl chain having from 1 to 12 carbon atoms and comprising an ammonium function. The term "$C_{1-12}$-pyridinium-alkyl" refers to an alkyl chain having from 1 to 12 carbon atoms and comprising a pyridinium function. The term "$C_{1-12}$-aldehyde-alkyl" refers to an alkyl chain having from 1 to 12 carbon atoms and comprising an aldehyde function. The term "$C_{1-12}$-nitro-alkyl" refers to an alkyl chain having from 1 to 12 carbon atoms and comprising a nitro function. The term "$C_{1-12}$-nitrile-alkyl" refers to an alkyl chain having from 1 to 12 carbon atoms and comprising a nitrile function.

The term "$C_{2-30}$-alkenyl" refers (also when it is a constituent of other radicals) to branched and unbranched alkenyl groups having from 2 to 30 carbon atoms, as long as they have at least one double bond. Correspondingly, the term "$C_{2-12}$-alkenyl" refers to alkenyl groups having from 2 to 12 carbon atoms and the term "$C_{2-6}$-alkenyl" refers to branched and unbranched alkenyl groups having from 2 to 6 carbon atoms, the term "$C_{2-4}$-alkenyl" refers to branched and unbranched alkenyl groups having from 2 to 4 carbon atoms. Preference is given to alkenyl groups having from 2 to 6 carbon atoms, particularly preferably from 2 to 4 carbon atoms. Examples which may be mentioned are: ethenyl and vinyl, propenyl, butenyl, pentenyl and hexenyl. Unless indicated otherwise, in the case of propenyl, butenyl, pentenyl and hexenyl, the definitions encompass all conceivable isomeric forms of the respective radicals. Thus, for example, propenyl encompasses 1-propenyl and 2-propenyl, butenyl encompasses 1-, 2- and 3-butenyl, 1-methyl-1-propenyl, 1-methyl-2-propenyl, etc.

The term "$C_{2-12}$-alkynyl" refers (also when it is a constituent of other radicals) to branched and unbranched alkynyl groups having from 2 to 12 carbon atoms, as long as they have at least one triple bond. Correspondingly, the term "$C_{2-6}$-alkynyl" refers to alkynyl groups having from 2 to 6 carbon atoms and the term "$C_{2-4}$-alkynyl" refers to branched and unbranched alkynyl groups having from 2 to 4 carbon atoms.

Preference is given to alkynyl groups having from 2 to 6 carbon atoms, particularly preferably from 2 to 4 carbon atoms. Examples which may be mentioned are: ethynyl, propynyl, butynyl, pentynyl and hexynyl. Unless indicated otherwise, in the case of propynyl, butynyl, pentynyl or hexynyl, the definitions encompass all conceivable isomeric forms of the respective radicals. Thus, for example, propynyl encompasses 1-propynyl and 2-propynyl, butynyl encompasses 1-, 2- and 3-butynyl, 1-methyl-1-propynyl, 1-methyl-2-propynyl, etc.

The term "$C_{1-12}$-alkoxy" refers (also when it is a constituent of other radicals) to branched and unbranched alkoxy groups having from 1 to 12 carbon atoms; correspondingly, the term "$C_{1-6}$-alkoxy" refers to branched and unbranched alkoxy groups having from 1 to 6 carbon atoms and the term "$C_{1-4}$-alkoxy" refers to branched and unbranched alkoxy groups having from 1 to 4 carbon atoms. Preference is given to alkoxy groups having from 1 to 6 carbon atoms, particularly preferably from 1 to 4 carbon atoms. Examples which may be mentioned are:

methoxy, ethoxy, propoxy, butoxy and pentoxy. The abbreviations MeO, EtO, PrO, etc., may also be used for the above-mentioned groups. Unless indicated otherwise, in the case of propoxy, butoxy and pentoxy, the definitions encompass all conceivable isomeric forms of the respective radicals. Thus, for example, propoxy encompasses n-propoxy and isopropoxy, butoxy encompasses isobutoxy, sec-butoxy and tert-butoxy, etc.

The term "$C_{5-12}$-cycloalkyl" refers (even when it is a constituent of other radicals) to cyclic alkyl groups having 5 to 12 carbon atoms. Examples which may be mentioned are: cyclopentyl and cyclohexyl. Unless indicated otherwise, the cyclic alkyl groups can be substituted by one or more radicals selected from the group consisting of methyl, ethyl, isopropyl, tert-butyl, hydroxy, fluorine, chlorine, bromine and iodine. Further, the cyclic alkyl groups can be substituted by one or more functions such as an amino function; they will then be referred to as aminocycloalkyl.

The term "aryl" refers (also when it is a constituent of other radicals) to aromatic ring systems having 6, 10 or more carbon atoms (up to approximately 20 carbon atoms). Examples which may be mentioned are: phenyl and naphthyl; the preferred aryl radical is phenyl. Unless indicated otherwise, the aromatics can be substituted by one or more radicals selected from the group consisting of methyl, ethyl, isopropyl, tert-butyl, hydroxy, fluorine, bromine and iodine. Further the aromatics can comprise one or more functional group; they will then be referred to as "heteroaryl".

The term "$C_{7-18}$-aralkyl" refers (also when it is a constituent of other radicals) to branched and unbranched alkyl groups which have from 1 to 8 carbon atoms and are substituted by an aromatic ring system having 6 or 10 carbon atoms; correspondingly, the term "$C_{7-11}$-aralkyl" refers to branched and unbranched alkyl groups which have from 1 to 4 carbon atoms and are substituted by an aromatic ring system having 6 carbon atoms. Examples which may be mentioned are: benzyl, 1- and 2-phenylethyl. Unless indicated otherwise, the aromatics can be substituted by one or more radicals selected from the group consisting of methyl, ethyl, isopropyl, tert-butyl, hydroxy, fluorine, bromine and iodine.

The term "indenylidene system" refers to a divalent radical derived from the cyclopentan ring of an indene wherein said indene consists of a benzene ring fused to a cyclopentadiene ring.

The sign:

stands for a cutoff in a covalent bond for the purpose of simplicity in representing side chains of compounds of the present invention. For instance, some examples of the present invention refer to a several optional side chains R3. A covalent bond cut by the above sign is actually linked to the Nitrogen (N) atom of the oxazine or oxazinone function.

The signs:

and stand for a E or Z configuration of a double bond (E/Z). Accordingly, atoms or atom-groups covalently linked to a double bond via this sign can be in CIS or TRANS position. It has to be understood that for the purpose of the present invention, compounds represented with the above sign can either comprise Z isomeres, E isomeres or a E/Z-mixture of said isomers.

Preparation of Compounds of General Formula 1 According to the Invention

The following preparation method encompasses examples of the present invention. A man skilled in the art will know how to prepare other embodiments falling within the scope of the present invention by inspection of the following operations. Particularly, different catalysts according to the invention can be obtained by modification of the side chains R1, R2 and/or R3 and/or a, b and/or c as defined within the present specification.

I-A—General Procedure for Cyclisation.

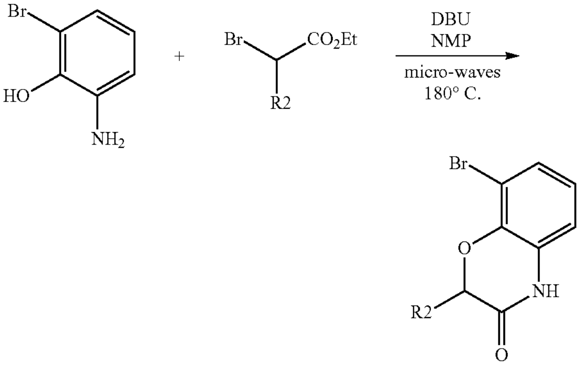

A mixture of 2-bromo-6-aminophenol, 0.9 eq of 1.8-diazabicyclo[5.4.0]undec-7-ene (DBU) and corresponding bromoester (1 eq) in 1-Methyl-2-pyrrolidinone (4 mL for 1 mmol of aminophenol) was warmed in micro-wave at 180° C. during 3 min. EtOAc (20 mL for 1 mmol of aminophenol was added. Organic layer was washed with Brine (3×), dried and concentrated. Products were purified on silica gel.

In the present preferred embodiment R1 is selected to be H. However, in other embodiments R1 is selected from the group consisting of H, $C_{2-12}$-alkenyl, $C_{2-12}$-alkynyl or aryl.

Depending on the side chain R2, compounds P1, P10 and P16 were obtained (see below). More generally R2 can be chosen to R2 is selected from the group consisting of H, $C_{1-12}$-alkyl, $C_{5-12}$-cycloalkyl, $C_{7-18}$-aralkyl or aryl. More preferentially, R2 is a methyl-, ethyl- or isopropyl-group.

P1

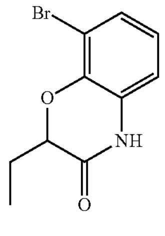

8-bromo-2-ethyl-2H-benzo[b][1,4]oxazin-3(4H)-one

Procedure & NMR Data: 1.5 g (7.9 mmol) of 2-bromo-6-aminophenol, 1.08 ml (0.9 eq, 7.11 mmol) of 1.8-diazabicyclo[5.4.0]undec-7-ene and 3.5 mL of DL-Ethyl 2-bromobutyrate (3 eq, 23.7 mmol)) in 30 mL of 1-Methyl-2-pyrrolidinone were mixed. 1.447 g of P1 were obtained, yield 71%.

$^1$H NMR (400 MHz, $CDCl_3$) δ 7.84 (s, 1H), 7.14 (dd, J=8.1, 1.4 Hz, 1H), 6.76 (dd, J=8.1, 7.9 Hz, 1H), 6.65 (dd, J=7.9, 1.4 Hz, 1H), 4.54 (dd, J=9.1, 4.2 Hz, 1H), 2.00-1.71 (m, 2H), 1.08 (t, J=7.4 Hz, 3H). $^{13}$C NMR (101 MHz, $CDCl_3$) δ 167.20, 139.69, 127.75, 127.27, 123.17, 114.43, 111.37, 79.04, 23.95, 9.61.

P10

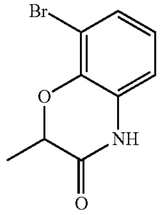

8-bromo-2-methyl-2H-benzo[b][1,4]oxazin-3(4H)-one

Procedure & NMR Data: 1.51 g (8 mmol) of 2-bromo-6-aminophenol, 1.1 ml (0.9 eq, 7.2 mmol) of 1,8-diazabicyclo[5.4.0]undec-7-ene and 2.1 mL (2 eq, 1.6 mmol) of Methyl 2-bromopropionate in 1-Methyl-2-pyrrolidinone (25 ml) were mixed. 1.55 g of P10 were obtained, yield 80%.

$^1$H NMR (400 MHz, $CDCl_3$) δ 8.09 (s broad, 1H), 7.23 (dd, J=8.1, 1.5 Hz, 1H), 6.86 (dd, J=8.1, 7.9 Hz, 1H), 6.76 (dd, J=7.9, 1.5 Hz, 1H), 4.78 (q, J=6.9 Hz, 1H), 1.64 (d, J=6.9 Hz, 3H). $^{13}$C NMR (101 MHz, $CDCl_3$) δ 168.4, 140.4, 127.8, 127.4, 123.3, 114.9, 111.1, 73.9, 16.3.

P16

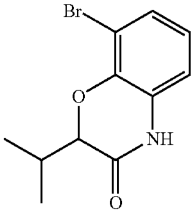

8-bromo-2-isopropyl-2H-benzo[b][1,4]oxazin-3(4H)-one

Procedure & NMR Data: 1.52 g (8 mmol) of 2-bromo-6-aminophenol, 1.1 mL (7.2 mmol, 0.9 eq) of 1,8-diazabicyclo[5.4.0]undec-7-ene and 3.35 g (2 eq, 16 mmol) of ethyl 2-bromo-3-methylbutyrate in 1-methyl-2-pyrrolidinone (20 mL) were mixed. 1.1 g of P16 were obtained, yield 50%.

$^1$H NMR (400 MHz, $CDCl_3$) δ 8.78 (s, 1H), 7.12 (dd, J=8.0, 1.5 Hz, 1H), 6.74 (dd, J=8.0, 7.9 Hz, 1H), 6.67 (dd, J=7.9, 1.5 Hz, 1H), 4.39 (d, J=6.2 Hz, 1H), 2.19 (qq, J=6.9, 6.7 Hz, 1H), 1.07 (d, J=6.9 Hz, 3H), 1.00 (d, J=6.7 Hz, 3H). $^{13}$C NMR (101 MHz, $CDCl_3$) δ 166.90, 140.59, 127.78, 126.96, 122.95, 114.59, 110.84, 82.49, 29.98, 18.62, 17.58.

In General, it should be noted that according to the invention R1 and R2 can each be, independently of one another, H or a substituted or unsubstituted, charged or uncharged side chain comprising up to 20 carbon atoms and optionally comprising one or more functional groups.

Also, it should be noted that the general procedure begins with z being a carbonyle group (cf. P1, P10 and P16). An amide reduction can be carried out in order to reduce the carbonyle group to a methylene group (see below procedure I-D).

I-B—General Procedure for Stille Reaction.

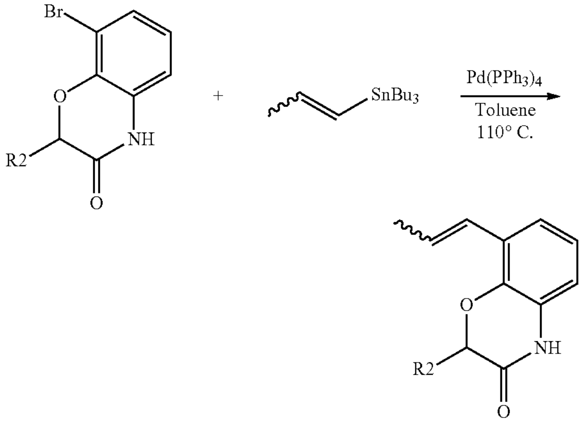

To a stirred solution of tetrakis(triphenylphosphine)Palladium (0) (5%) in toluene (1 mL for 10 mg of tetrakis) was added in solution of toluene (4 ml for 1 mmol of oxazinone) latter oxazinone. The mixture was degassed during 15 min and Propenyl-tributyltin (1.5 eq) was added and stirred at 110° C. for 12 h under nitrogen atmosphere. After filtration and washed on celite the product was purified on silica gel.

Depending on the side chain R2, compounds P2 (R2 is ethyl), P11 (R2 is methyl) and P17 (R2 is isopropyl) were obtained (see below).

P2

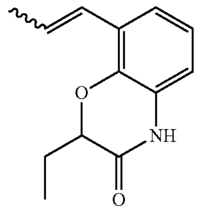

2-ethyl-8-(prop-1-enyl)-2H-benzo[b][1,4]oxazin-3(4H)-one

Procedure & NMR Data: 198.5 mg (5%, 0.17 mmol) of tetrakis(triphenylphosphine)Palladium (0) in toluene (7.5 mL) was added in solution of toluene (7.5 mL) of oxazinone P1. 1.84 g (1.5 eq, 5.55 mmol) of Propenyl-tributyltin were added. 786 mg of P2 was obtained, 98% yield.

$^1$H NMR (400 MHz, $CDCl_3$) δ 7.65 (s, 1H), 7.04 (dd, J=7.9, 1.3 Hz, 1H), 6.83 (dd, J=7.9, 7.7 Hz, 1H), 6.59 (dq, J=15.9, 1.7 Hz, 1H), 6.53 (dd, J=7.7, 1.3 Hz, 1H), 6.26 (dq, J=15.9, 6.7 Hz, 1H), 4.45 (dd, J=8.7, 4.3 Hz, 1H), 1.97-1.71 (m, 5H), 1.11-0.99 (m, 3H), 0.85 (t, J=7.3 Hz, 3H). $^{13}$C NMR (101 MHz, $CDCl_3$) δ 168.67, 168.65, 140.26, 139.51, 128.31, 127.91, 127.21, 126.71, 126.55, 126.33, 124.29, 123.63, 122.12, 121.53, 114.37, 114.04, 78.22, 78.21, 23.85, 23.79, 18.97, 17.31, 14.80, 13.60, 9.82, 9.69.

P11

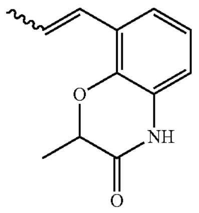

2-methyl-8-(prop-1-enyl)-2H-benzo[b][1,4]oxazin-3 (4H)-one

Procedure & NMR Data:to 370 mg (5%, 0.32 mmol) of tetrakis(triphenylphosphine)-Palladium (0) in toluene (10 mL) was added 1.55 g (6.4 mmol) of oxazinone P10 in solution of toluene (40 mL). The mixture was degassed during 15 min and 3.18 g (1.5 eq, 9.6 mmol) of propenyl-tributyltin were added. 1.27 g of P11 were obtained, yield 98%.

$^{1}H$ NMR (400 MHz, $CDCl_3$) δ 7.84 (d, J=10.4 Hz, 1H), 7.07-6.91 (m, 1H), 6.90-6.79 (m, 1H), 6.66-6.40 (m, 2H), 6.32-5.74 (m, 1H), 4.60 (q, J=6.8 Hz, 1H), 1.90-1.73 (m, 3H), 1.59-1.51 (m, 3H). $^{13}C$ NMR (101 MHz, $CDCl_3$) δ 168.7, 168.6, 140.7, 139.9, 128.4, 127.9, 127.2, 126.7, 126.5, 124.9, 124.3, 123.6, 122.2, 121.7, 121.1, 114.3, 113.9, 73.4, 73.3, 18.9, 16.3, 16.2, 14.8.

P17

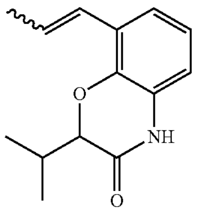

2-isopropyl-8-(prop-1-enyl)-2H-benzo[b][1,4]oxazin-3(4H)-one

Procedure & NMR Data: to 235 mg (5%, 0.2 mmol) of tetrakis(triphenylphosphine)Palladium (0) in toluene (6 mL) was added 1.1 g (4 mmol) of oxazinone P16 in solution of toluene (24 mL). The mixture was degassed during 15 min and 2.02 g (1.5 eq, 6 mmol) of propenyl-tributyltin were added. 907 mg of P17 were obtained, yield 98%.

$^{1}H$ NMR (400 MHz, $CDCl_3$) δ 9.32 (d, J=13.9 Hz, 1H), 6.96 (ddd, J=40.9, 7.9, 1.3 Hz, 1H), 6.80 (dt, J=13.9, 7.9 Hz, 1H), 6.68-6.60 (m, 1H), 6.60-6.41 (m, 1H), 6.32-5.76 (m, 1H), 4.31 (dd, J=6.0, 1.5 Hz, 1H), 2.23 (qq, J=6.9, 6.9 Hz, 1H), 1.80 (ddd, J=29.2, 6.9, 1.8 Hz, 3H), 1.05 (dd, J=9.0, 6.9 Hz, 3H), 0.97 (dd, J=6.9, 6.9 Hz, 3H). $^{13}C$ NMR (101 MHz, $CDCl_3$) δ 167.70, 140.75, 139.99, 128.23, 127.89, 126.84, 126.34, 126.29, 126.06, 124.95, 124.30, 123.67, 121.92, 121.31, 121.20, 114.23, 113.90, 81.81, 81.79, 29.72, 29.63, 26.91.

I-C—General Procedure for Amide Alkylation.

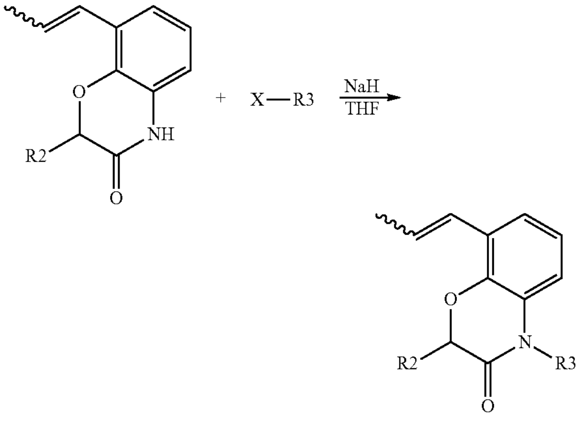

Appropriate halogen compound (1.2 eq) was added to a mixture of NaH (4 eq) and considered oxazinone in THF (1 mL for 0.1 mmol of oxazinone) at 0° C. The mixture was stirred at room temperature for 2-3 h. THF was removed under reduce pressure and EtOAc was added. The organic layer was washed with a saturated solution of $NaHCO_3$ and then with brine, dried over $MgSO_4$ and evaporated to dryness. Products were purified on silica gel.

Depending on the side chain R2 and/or the side chain R3, compounds P3 to P9, P12 to P15 and P18 to P21 were obtained (see below).

According to the invention, R3 can be H or a substituted or unsubstituted, charged or uncharged side chain comprising up to 20 carbon atoms and optionally comprising one or more functional groups Preference is given when R3 is selected from the group consisting of H, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyl, nitrile or a radical selected from the group consisting of ketones COR4, esters $CO_2R4$, oxalates $COCO_2R4$, sulfones $SO_2R4$ or amides CONHR4 wherein, R4 is selected from the group consisting of H, $C_{1-12}$-alkyl, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyle, nitrile.

In particularly preferred embodiments R3 is a side chain of the formula $R3^a$ or $R3^b$ as described above. However, in these embodiments z is chosen to be a methylene as shown in above formula $1^b$. For z to become a methylene, one can refer to general procedure I-D that shows a amide reduction.

In other particularly preferred embodiments R3 is a side chain of the formula $R3^c$, $R3^d$, $R3^e$, $R3^f$, $R3^g$, $R3^h$, $R3^i$, $R3^j$, $R3^k$, $R3^l$, $R3^m$, $R3^n$, $R3^o$ or $R3^p$ as described above. In these embodiments z is chosen to be either a methylene as shown in above formula $1^b$ or a carbonyl as shown in above formula $1^a$.

P3

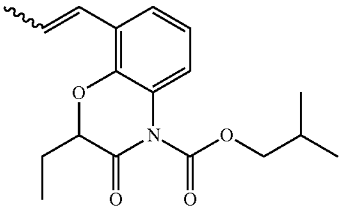

isobutyl 2-ethyl-3-oxo-8-(prop-1-enyl)-2H-benzo[b][1,4]oxazine-4(3H)-carboxylate Procedure & NMR Data: 85 μL (2.5 eq, 0.65 mmol) of isobutyl chloroformate was added to a mixture of 42 mg (4 eq, 1.04 mmol) of NaH and oxazinone P2 (56 mg, 0.26 mmol) in THF (5 mL). 42 mg of P3 were obtained, yield 51%.

$^1$H NMR (400 MHz, $CDCl_3$) δ 7.14 (dd, J=7.5, 1.6 Hz, 1H), 6.96-6.84 (m, 2H), 6.63-6.56 (m, 1H), 6.25 (dq, J=15.9, 6.6 Hz, 1H), 4.32 (dd, J=8.8, 4.4 Hz, 1H), 4.10 (d, J=6.6 Hz, 2H), 2.07-1.74 (m, 6H), 1.04 (t, J=7.4 Hz, 3H), 0.93 (d, J=6.7 Hz, 6H). $^{13}$C NMR (101 MHz, $CDCl_3$) δ 166.45, 166.40, 152.04, 142.32, 141.55, 128.69, 128.33, 128.00, 127.45, 126.63, 126.43, 126.38, 123.99, 123.40, 122.51, 122.28, 121.73, 117.47, 117.12, 79.23, 79.22, 74.62, 74.60, 73.94, 69.80, 27.67, 23.14, 23.12, 18.99, 18.94, 18.92, 14.75, 9.72, 9.60. (major signals are double due to two isomers Z/E for the double bond)

P4

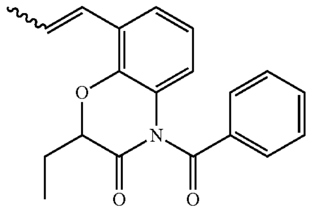

2-ethyl-4-(phenylcarbonyl)-8-(prop-1-enyl)-2H-benzo[b][1,4]oxazin-3(4H)-one

Procedure & NMR Data: 142 μL (2.5 eq, 1.23 mmol) of benzoyl chloride was added to a mixture of 78 mg of NaH (4 eq, 1.96 mmol) and 100 mg (0.49 mmol) of oxazinone P2 in THF (9.5 ml). 58 mg of P4 were obtained, yield 77%.

$^1$H NMR (400 MHz, $CDCl_3$) δ 7.86-7.77 (m, 2H), 7.57-7.49 (m, 1H), 7.43-7.32 (m, 2H), 7.15-6.99 (m, 1H), 6.90-6.71 (M, 2H), 6.69-6.46 (m, 1H), 6.34-5.83 (m, 1H), 4.48-4.42 (m, 1H), 2.05-1.74 (m, 5H), 1.09 (t, J=7.4 Hz, 3H).

P5

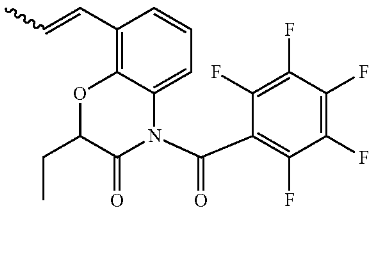

2-ethyl-4-(perfluorophenylcarbonyl)-8-(prop-1-enyl)-2H-benzo[b][1,4]oxazin-3(4H)-one Procedure & NMR Data: 265 μL of pentafluorobenzoyl chloride (2 eq, 1.84 mmol) was added to a mixture of 148 mg of NaH (4 eq, 3.68 mmol) and 200 mg (0.92 mmol) of oxazinone P2 in THF (22 ml). 240 mg of P5 were obtained, yield 63%.

$^1$H NMR (400 MHz, $CDCl_3$) δ 7.52 (ddd, J=22.9, 8.2, 1.3 Hz, 1H), 7.22 (ddd, J=43.6, 7.8, 1.2 Hz, 1H), 7.07-6.96 (m, 1H), 6.53 (ddd, J=13.8, 13.1, 1.6 Hz, 1H), 6.34-5.82 (m, 1H), 4.31 (ddd, J=8.7, 4.5, 3.3 Hz, 1H), 1.94-1.73 (m, 2H), 1.03 (dt, J=9.3, 7.4 Hz, 1H). $^{13}$C NMR (101 MHz, $CDCl_3$) δ 170.37, 170.27, 143.98, 143.21, 129.14, 128.79, 128.49, 128.07, 127.94, 125.49, 125.31, 124.15, 123.69, 123.08, 122.66, 122.13, 120.22, 119.92, 79.54, 79.49, 23.12, 18.94, 14.76, 9.55, 9.45. (major signals are double due to two isomers Z/E for the double bond). $^{19}$F NMR (376 MHz, $CDCl_3$) δ −142.42 (d, J=21.6 Hz, 2F), −150.02 (d, J=9.9 Hz), −160.44 (dd, J=21.6, 9.9 Hz, 2F).

P6

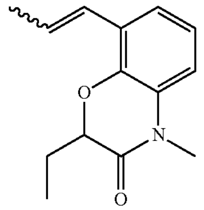

2-ethyl-4-methyl-8-(prop-1-enyl)-2H-benzo[b][1,4]oxazin-3(4H)-one

Procedure & NMR Data: 287 μL (10 eq, 4.6 mmol) of Methyl iodide was added to a mixture of 74 mg (4 eq, 1.84 mmol) of NaH and 100 mg (0.46 mmol) of oxazinone P2 in THF (10 mL). 75 mg of 6 were obtained, yield 71%.

$^1$H NMR (400 MHz, $CDCl_3$) δ 7.08-6.83 (m, 2H), 6.74 (m, 1H), 6.65-6.41 (m, 1H), 6.29-5.74 (m, 1H), 4.40 (dd, J=9.1, 4.2 Hz, 1H), 3.26 (dd, J=5.8, 0.2 Hz, 3H), 1.92-1.66 (m, 5H), 1.00 (dt, J=8.7, 7.4 Hz, 3H).

P7

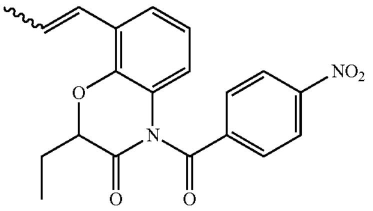

2-ethyl-4-(4-nitrophenylcarbonyl)-8-(prop-1-enyl)-2H-benzo[b][1,4]oxazin-3(4H)-one Procedure & NMR Data: 107 mg (2.5 eq, 0.58 mmol) of 4-Nitrobenzoyl chloride was added to a mixture of 37 mg (4 eq, 0.92 mmol) of NaH and 50 mg (0.23 mmol) of oxazinone P2 in THF (10 mL). 81 mg of P7 were obtained, yield 96%.

$^1$H NMR (400 MHz, $CDCl_3$) δ 8.30 (dd, J=9.0, 3.7 Hz, 2H), 7.95 (dd, J=9.0, 3.5 Hz, 2H), 7.26 (dd, J=7.7, 1.5 Hz, 1H), 7.17 (dd, J=7.7, 1.3 Hz, 1H), 7.07 (dd, J=8.2, 1.5 Hz, 1H), 7.03-6.91 (m, 2H), 6.71 (qd, J=16.2, 1.8 Hz, 1H), 6.56 (qd, J=11.5, 1.8 Hz, 1H), 6.38 (qd, J=15.8, 6.6 Hz, 1H), 5.96 (qd, J=11.5, 7.1 Hz, 1H), 4.48 (ddd, J=8.5, 4.5, 3.7 Hz, 1H), 1.95 (dd, J=6.6, 1.8 Hz, 3H), 2.10-1.89 (m, 2H), 1.87 (dd, J=7.1, 1.9 Hz, 3H), 1.14 (td, J=9.2, 7.4 Hz, 3H). $^{13}$C NMR (101 MHz, $CDCl_3$) δ 170.0, 170.0, 168.0, 150.4, 142.2, 141.3, 139.3, 139.2, 130.6, 130.3, 130.2, 129.1, 128.9, 128.4, 127.9, 127.0, 126.9, 126.6, 124.0, 123.8, 123.5, 123.2, 123.1, 122.7, 122.2, 118.9, 116.5, 78.9, 78.8, 23.0, 22.9, 18.9, 14.8, 9.6, 9.5. (major signals are double due to two isomers Z/E for the double bond).

P8

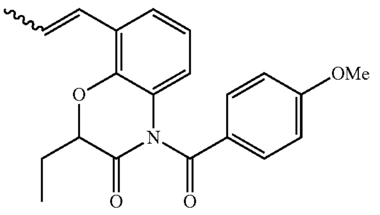

2-ethyl-4-(4-methoxyphenylcarbonyl)-8-(prop-1-enyl)-2H-benzo[b][1,4]oxazin-3(4H)-one Procedure & NMR Data: 137 mg (2.5 eq, 0.8 mmol) of p-Anisoyl chloride was added to a mixture of 49 mg (4 eq, 1.28 mmol) of NaH and 73 mg (0.32 mmol) of oxazinone P2 in THF (14 mL). 73 mg of P8 were obtained, yield 62%.

$^1$H NMR (400 MHz, $CDCl_3$) δ 7.85-7.76 (m, 2H), 7.13-6.98 (m, 1H), 6.91-6.75 (m, 3H), 6.69-6.46 (m, 2H), 6.38-5.81 (m, 1H), 4.47 (ddd, J=8.9, 4.4, 2.9 Hz, 1H), 3.79 (d, J=2.7 Hz, 3H), 2.03-1.74 (m, 5H), 1.08 (dt, J=14.9, 7.4 Hz, 3H). $^{13}$C NMR (101 MHz, $CDCl_3$) 170.5, 166.5, 164.9, 141.0, 140.2, 133.1, 128.7, 128.4, 128.0, 127.4, 127.4, 125.8, 125.0, 124.9, 124.1, 123.4, 122.4, 122.0, 121.9, 115.4, 115.0, 114.5, 78.7, 78.6, 55.6, 23.2, 23.1, 18.9, 14.8, 9.7, 9.6. (major signals are double due to two isomers Z/E for the double bond).

P9

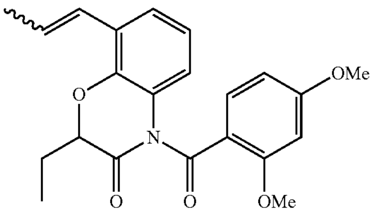

4-(2,4-dimethoxyphenylcarbonyl)-2-ethyl-8-(prop-1-enyl)-2H-benzo[b][1,4]oxazin-3(4H)-one Procedure & NMR Data: 162 mg (2.5 eq, 0.8 mmol) of 2,4-Dimethoxybenzoyl chloride was added to a mixture of 49 mg (4 eq, 1.28 mmol) of NaH and 73 mg (0.32 mmol) of oxazinone P2 in THF (14 mL). 109 mg of P9 were obtained, yield 84%.

$^1$H NMR (400 MHz, $CDCl_3$) δ 7.76 (dd, J=8.8, 1.2 Hz, 1H), 7.14-6.97 (m, 1H), 6.97-6.75 (m, 2H), 6.69-6.42 (m, 2H), 6.34-5.78 (m, 2H), 4.40-4.32 (m, 1H), 3.78 (d, J=2.3 Hz, 3H), 3.63 (d, J=4.4 Hz, 3H), 1.98-1.75 (m, 5H), 1.05 (dt, J=9.5, 7.4 Hz, 3H). $^{13}$C NMR (101 MHz, $CDCl_3$) δ 168.2, 166.7, 165.5, 160.5, 160.4, 142.1, 134.7, 134.7, 128.3, 127.9, 127.1, 125.8, 124.3, 123.7, 122.1, 121.9, 121.5, 116.6, 116.3, 105.8, 98.5, 78.9, 55.6, 26.9, 23.0, 18.9, 14.8, 9.9, 9.8. (major signals are double due to two isomers Z/E for the double bond).

P12

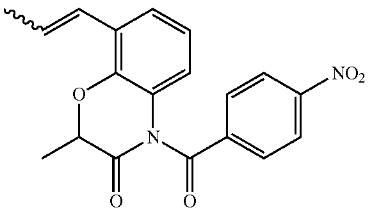

2-methyl-4-(4-nitrophenylcarbonyl)-8-(prop-1-enyl)-2H-benzo[b][1,4]oxazin-3(4H)-one Procedure & NMR Data: 160 mg (2.5 eq, 0.85 mmol) of 4-Nitrobenzoyl chloride was added to a mixture of 53 mg (4 eq, 1.36 mmol) of NaH and 73 mg (0.34 mmol) of oxazinone P10 in THF (14 mL). 108 mg of P12 were obtained, yield 86%.

$^1$H NMR (400 MHz, $CDCl_3$) δ 8.30-8.19 (m, 2H), 7.92-7.82 (m, 2H), 7.24-7.06 (m, 1H), 7.03-6.83 (m, 2H), 6.53 (dddd, J=11.5, 3.2, 2.6, 1.6 Hz, 1H), 6.36-5.81 (m, 1H), 4.58 (qd, J=6.7, 1.3

Hz, 1H), 1.91-1.76 (m, 3H), 1.56 (dd, J=8.2, 6.7 Hz, 3H). $^{13}$C NMR (101 MHz, $CDCl_3$) δ 170.03, 168.35, 150.47, 142.79, 142.00, 139.34, 139.25, 130.30, 130.25, 129.18, 128.90, 127.73, 127.03, 126.80, 124.05, 123.85, 123.21, 123.14, 122.82, 122.30, 117.12, 116.78, 74.05, 26.91, 18.96, 15.52, 14.82.

P13

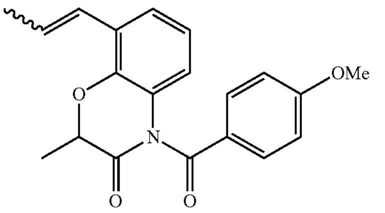

4-(4-methoxyphenylcarbonyl)-2-methyl-8-(prop-1-enyl)-2H-benzo[b][1,4]oxazin-3(4H)-one Procedure & NMR Data: 117 µL (2.5 eq, 0.85 mmol) of p-Anisoyl chloride was added to a mixture of 53 mg (4 eq, 1.36 mmol) of NaH and 73 mg (0.34 mmol) of oxazinone P10 in THF (14 mL). 85 mg of P13 were obtained, yield 69%.

$^1$H NMR (400 MHz, $CDCl_3$) δ 7.86-7.73 (m, 2H), 7.05 (ddd, J=42.8, 7.8, 1.2 Hz, 1H), 6.94-6.73 (m, 3H), 6.70-6.42 (m, 2H), 6.35-5.77 (m, 1H), 4.64 (td, J=6.8, 0.7 Hz, 1H), 3.79 (d, J=2.8 Hz, 3H), 1.83 (ddd, J=31.6, 6.9, 1.8 Hz, 3H), 1.58 (t, J=6.8 Hz, 3H). $^{13}$C NMR (101 MHz, $CDCl_3$) δ 170.13, 170.02, 166.87, 166.85, 164.94, 141.60, 140.83, 133.08, 133.06, 132.84, 128.78, 128.41, 127.87, 127.79, 127.59, 127.32, 125.86, 124.96, 124.87, 124.14, 123.50, 122.55, 122.01, 115.57, 115.26, 114.46, 114.13, 73.82, 55.64, 26.91, 18.95, 15.76, 14.84.

P14

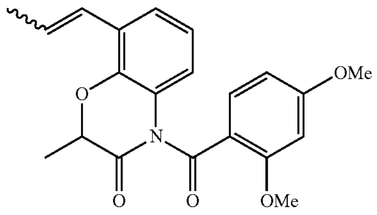

4-(2,4-dimethoxyphenylcarbonyl)-2-methyl-8-(prop-1-enyl)-2H-benzo[b][1,4]oxazin-3(4H)-one Procedure & NMR Data: 173 mg (2.5 eq, 0.85 mmol) of 2,4-Dimethoxybenzoyl chloride was added to a mixture of 53 mg (4 eq, 1.36 mmol) of NaH and 73 mg (0.34 mmol) of oxazinone P10 in THF (14 mL). 102 mg of P14 were obtained, yield 76%.

$^1$H NMR (400 MHz, $CDCl_3$) δ 7.76 (dd, J=8.8, 1.6 Hz, 1H), 7.16-6.71 (m, 3H), 6.68-6.39 (m, 2H), 6.34-5.74 (m, 2H), 4.52 (q, J=6.8 Hz, 1H), 3.77 (d, J=2.3 Hz, 3H), 3.63 (d, J=4.5 Hz, 3H), 1.82 (ddd, J=32.0, 6.9, 1.8 Hz, 1H), 1.53 (dd, J=8.0, 6.8 Hz, 1H). $^{13}$C NMR (101 MHz, $CDCl_3$) δ 168.20, 168.14, 167.17, 167.16, 165.53, 165.51, 160.41, 160.35, 142.66, 134.73, 134.68, 128.38, 127.82, 127.46, 127.42, 127.23, 126.94, 125.83, 124.29, 123.73, 122.17, 121.91, 121.65, 116.74, 116.37, 116.19, 116.07, 105.87, 105.85, 98.45, 73.92, 55.63, 55.60, 49.43, 30.67, 29.57, 26.90, 18.93, 17.65, 15.68, 15.64, 14.79.

P15

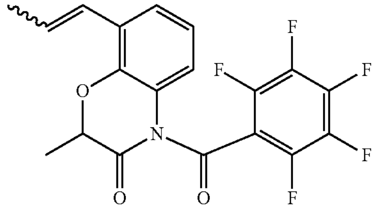

2-methyl-4-(perfluorophenylcarbonyl)-8-(prop-1-enyl)-2H-benzo[b][1,4]oxazin-3(4H)-one Procedure & NMR Data: 124 μL (2.5 eq, 0.85 mmol) of pentafluorobenzoyl chloride was added to a mixture of 53 mg (4 eq, 1.36 mmol) of NaH and 73 mg (0.34 mmol) of oxazinone P10 in THF (14 mL). 134 mg of P15 were obtained, yield 90%.

$^1$H NMR (400 MHz, $CDCl_3$) δ 7.52 (ddd, J=23.4, 8.3, 1.4 Hz, 1H), 7.22 (ddd, J=44.7, 7.8, 1.2 Hz, 1H), 7.10-6.95 (m, 1H), 6.64-6.40 (m, 1H), 6.35-5.79 (m, 1H), 4.47 (qd, J=6.8, 1.7 Hz, 1H), 1.82 (ddd, J=32.4, 6.9, 1.8 Hz, 3H), 1.52 (dd, J=8.5, 6.8 Hz, 3H). $^{19}$F NMR (376 MHz, $CDCl_3$) δ −142.42 (d, J=17.8 Hz, 2F), −149.92 (dd, J=34.2, 20.7 Hz, 1F), −160.38 (td, J=20.7, 6.1 Hz, 2F). $^{13}$C NMR (101 MHz, $CDCl_3$ ) δ 170.8, 170.7, 144.4, 143.7, 129.1, 128.7, 128.3, 128.0, 127.7, 125.5, 125.3, 124.1, 123.7, 123.1, 122.7, 122.2, 120.3, 120.0, 74.8, 74.7, 18.9, 15.5, 14.7, 14.1.

P18

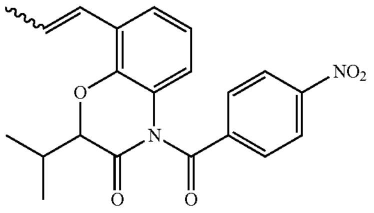

2-isopropyl-4-(4-nitrophenylcarbonyl)-8-(prop-1-enyl)-2H-benzo[b][1,4]oxazin-3(4H)-one Procedure & NMR Data: 151 mg (2.5 eq, 0.8 mmol) of 4-Nitrobenzoyl chloride was added to a mixture of 48 mg (4 eq, 1.28 mmol) of NaH and 74 mg (0.32 mmol) of oxazinone P17 in THF (14 ml). 100 mg of P18 were obtained, yield 83%.

$^1$H NMR (400 MHz, $CDCl_3$) δ 8.29-8.20 (m, 2H), 7.95-7.85 (m, 2H), 7.25-7.06 (m, 1H), 7.03-6.82 (m, 2H), 6.71-6.42 (m, 1H), 6.39-5.71 (m, 1H), 4.33-4.14 (m, 1H), 2.30-2.17 (m, 1H), 1.84 (ddd, J=31.2, 6.9, 1.8 Hz, 3H), 1.10-0.98 (m, 6H). $^{13}$C NMR (101 MHz, $CDCl_3$) δ 170.31, 167.45, 167.41, 150.46, 141.39, 139.53, 130.25, 130.19, 129.08, 128.91, 128.30, 127.76, 126.99, 126.51, 124.05, 123.79, 123.24, 123.09, 122.63, 122.07, 116.73, 116.36, 82.46, 82.43, 28.55, 28.50, 26.91, 19.01, 18.79, 18.72, 17.64, 17.53, 14.82.

P19

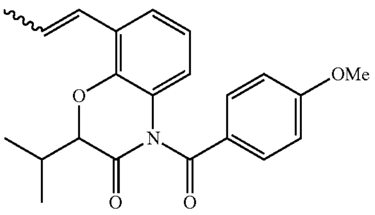

2-isopropyl-4-(4-methoxyphenylcarbonyl)-8-(prop-1-enyl)-2H-benzo[b][1,4]oxazin-3(4H)-one Procedure & NMR Data: 138 mg (2.5 eq, 0.8 mmol) of p-Anisoyl chloride was added to a mixture of 48 Mg (4 eq, 1.28 mmol) of NaH and 74 mg (0.32 mmol) of oxazinone P17 in THF (14 mL). 82 mg of P19 were obtained, yield 65%.

$^1$H NMR (400 MHz, $CDCl_3$) δ 7.80 (dd, J=9.0, 6.9 Hz, 2H), 7.04 (ddd, J=41.4, 7.8, 1.2 Hz, 1H), 6.90-6.83 (m, 2H), 6.78 (dt, J=10.7, 7.9 Hz, 1H), 6.70-6.47 (m, 2H), 6.36-5.81 (m, 1H), 4.28 (dd, J=6.8, 3.3 Hz, 1H), 3.79 (d, J=2.8 Hz, 3H), 2.32-2.20 (m, 1H), 1.84 (ddd, J=30.2, 6.9, 1.8 Hz, 3H), 1.12-0.99 (m, 6H). $^{13}$C NMR (101 MHz, $CDCl_3$) δ 171.15, 170.35, 165.82, 164.92, 141.23, 140.41, 133.05, 133.02, 128.63, 128.38, 127.76, 127.47, 127.24, 125.83, 125.14, 125.03, 124.09, 123.54, 122.31, 121.97, 121.72, 115.25, 114.94, 114.45, 82.29, 82.27, 60.39, 55.63, 28.79, 28.70, 21.04, 19.01, 18.81, 18.74, 17.83, 17.73, 14.83, 14.19.

P20

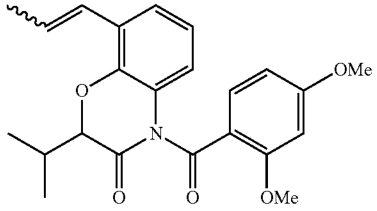

4-(2,4-dimethoxyphenylcarbonyl)-2-isopropyl-8-(prop-1-enyl)-2H-benzo[b][1,4]oxazin-3(4H)-one Procedure & NMR Data: 163 mg (2.5 eq, 0.8 mmol) of 2,4-Dimethoxybenzoyl chloride was added to a mixture of 48 mg (4 eq, 1.28 mmol) of NaH and 74 mg (0.32 mmol) of oxazinone P17 in THF (14 mL). 106 mg of P20 were obtained, yield 80%.

$^{1}$H NMR (400 MHz, $CDCl_3$) δ 7.75 (dd, J=8.8, 1.0 Hz, 1H), 7.04 (ddd, J=43.6, 7.5, 1.6 Hz, 1H), 6.93-6.72 (m, 2H), 6.69-6.45 (m, 2H), 6.34-5.78 (m, 2H), 4.17 (dd, J=7.0, 4.6 Hz, 1H), 3.77 (d, J=2.3 Hz, 3H), 3.62 (d, J=4.7 Hz, 3H), 2.26-2.12 (m, 1H), 1.82 (ddd, J=31.4, 6.9, 1.8 Hz, 3H), 1.09-0.95 (m, 6H). $^{13}$C NMR (101 MHz, $CDCl_3$) δ 171.15, 168.45, 165.80, 165.74, 165.53, 165.49, 160.51, 160.43, 142.27, 134.72, 134.66, 128.29, 127.84, 127.38, 127.19, 126.98, 126.89, 125.80, 124.24, 123.76, 121.94, 121.88, 121.37, 116.47, 116.35, 116.20, 116.07, 105.79, 105.77, 98.42, 82.46, 60.39, 55.60, 28.48, 28.43, 21.04, 18.99, 18.85, 18.78, 17.88, 17.78, 14.77, 14.19.

P21

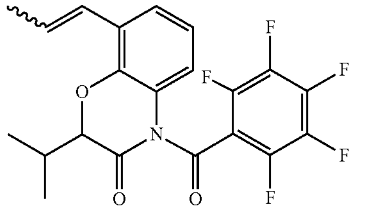

2-isopropyl-4-(perfluorophenylcarbonyl)-8-(prop-1-enyl)-2H-benzo[b][1,4]oxazin-3(4H)-one Procedure & NMR Data: 187 mg (2.5 eq, 0.8 mmol) of pentafluorobenzoyl chloride was added to a mixture of 48 mg (4 eq, 1.28 mmol) of NaH and 74 mg (0.32 mmol) of oxazinone P17 in THF (14 mL). 133 mg of P21 were obtained, yield 96%.

$^{1}$H NMR (400 MHz, $CDCl_3$) δ 7.49 (ddd, J=22.9, 8.2, 1.4 Hz, 1H), 7.22 (ddd, J=44.9, 7.8, 1.2 Hz, 1H), 7.05-6.94 (m, 1H), 6.54 (ddq, J=55.1, 11.6, 1.7 Hz, 1H), 6.35-5.81 (m, 1H), 4.14 (dd, J=6.3, 4.2 Hz, 1H), 2.20-2.09 (m, 1H), 1.83 (ddd, J=31.3, 6.9, 1.8 Hz, 3H), 1.01 (dd, J=8.6, 6.9 Hz, 3H), 0.95 (dd, J=7.5, 6.8 Hz, 3H). $^{19}$F NMR (376 MHz, $CDCl_3$) δ −142.33--142.68 (m, 2F), −150.12 (t, J=20.4 Hz, 1F), −160.22--160.69 (m, 2F). $^{13}$C NMR (101 MHz, $CDCl_3$) δ 169.56, 169.51, 144.02, 143.22, 129.14, 128.80, 128.07, 127.86, 125.31, 125.14, 124.14, 123.69, 123.15, 122.55, 122.00, 120.13, 119.81, 83.13, 83.07, 29.69, 28.66, 26.91, 18.97, 18.75, 18.68, 17.33, 17.22, 14.79.

I-D—General Procedure for Amide Reduction.

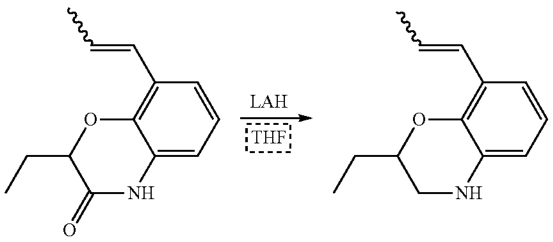

Appropriate oxazinone was added in solution in THF (Tetrahydrofuran) (16.4 mL for 1 mmol) to a suspension of 418 mg (2 eq, 11 mmol) of LAH (Lithium Aluminium Hydride) in THF (5 mL for 1.1 mmol) at 0° C. The result suspension was stirred at room temperature for 1 h. $H_2O$ and a solution af NaOH 1N was slowly added. The precipitate was filtered off on celite and washed with warm THF. No further purification is done for these products. Product P22 was obtained (NMR DATA are shown below)

In this way, catalysts compounds of the present invention can be obtained where z is methylene. Of course, different preparation of those compounds depend on selected R1, R2 and R3 side chains (see below procedure I-E).

P22

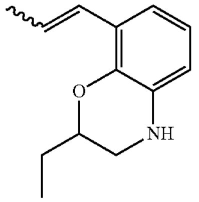

2-ethyl-8-(prop-1-enyl)-3,4-dihydro-2H-benzo[b][1,4]oxazine

Procedure & NMR Data: 1.2 g (5.5 mmol) of oxazinone P1 was added in solution in THF (90 mL) to a suspension of 418 mg (2 eq, 11 mmol) of LAH in THF (50 mL) at 0° C. The result suspension was stirred at room temperature for 1 h. $H_2O$ and a solution af NaOH 1N was slowly added. The precipitate was filtered off on celite and washed with warm THF. No further purification is done for these products. 1.1 g of P22 were obtained, yield 99%.

$^{1}$H NMR (400 MHz, $CDCl_3$) δ 6.75-6.34 (m, 4H), 6.23-5.68 (m, 1H), 3.98-3.91 (m, 1H), 3.65 (d, J=10.1 Hz, 1H), 3.34-3.01 (m, 2H), 2.04-1.86 (m, 2H), 1.84-1.74 (m, 3H), 1.05-0.96 (m, 3H). $^{13}$C NMR (101 MHz, $CDCl_3$) δ 141.48, 140.80, 133.27, 133.12, 126.63, 126.39, 126.15, 125.85, 125.42, 124.84, 120.55, 119.88, 119.86, 116.11, 113.94, 113.64, 107.96, 75.37, 75.35, 67.70, 45.13, 45.11, 29.13, 27.92, 27.17, 25.97, 25.93, 23.92, 18.98, 15.46, 14.89, 14.82, 13.65, 9.85, 9.78.

I-E—General Procedure for Amine Alkylation.

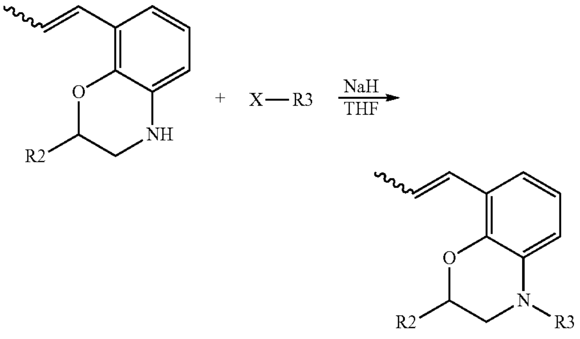

Appropriate halogen compound (1.2 eq) was added to a mixture of NaH (4 eq) and considered oxazinone in THF (10 mL for 0.5 mmol of oxazinone) at 0° C. The mixture was stirred at room temperature for 2-3 h. THF was removed under reduce pressure and EtOAc was added. The organic layer was washed with a saturated solution of NaHCO3 and then with brine, dried over $MgSO_4$ and evaporated to dryness. Products were purified on silica gel.

Depending on the side chain R2 and/or the side chain R3, compounds P23 to P31 were obtained (see below).

According to the invention, R3 can be H or a substituted or unsubstituted, charged or uncharged side chain comprising up to 20 carbon atoms and optionally comprising one or more functional groups Preference is given when R3 is selected from the group consisting of H, $C_{1-12}$-alkyl, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyl, nitrile or a radical selected from the group consisting of ketones COR4, esters $CO_2R4$, oxalates $COCO_2R4$, sulfones $SO_2R4$ or amides CONHR4 wherein, R4 is selected from the group consisting of H, $C_{1-12}$-alkyl, $C_{5-12}$-cycloalkyl, $C_{7-18}$-aralkyl, aryl, $C_{1-12}$-halogeno-alkyl, $C_{1-12}$-ammonium-alkyl, $C_{1-12}$-pyridinum-alkyl, $C_{1-12}$-aldehyde-alkyl, $C_{1-12}$-nitro-alkyle, nitrile.

In particularly preferred embodiments R3 is a side chain of the formula $R3^{a}$ or $R3^{b}$ as described above. This results in the catalysts according to the invention P30 and P31 respectively. It must be noted here that P30 and P31 do not follow general procedure I-E. Synthesis details are given below at corresponding products P30 and P31.

In other particularly preferred embodiments R3 is a side chain of the formula $R3^{c}$, $R3^{d}$, $R3^{e}$, $R3^{f}$, $R3^{g}$, $R3^{h}$, $R3^{i}$, $R3^{j}$, $R3^{k}$, $R3^{l}$, $R3^{m}$, $R3^{h}$, $R3^{o}$ or $R3^{p}$ as described above. In these embodiments z is chosen to be either a methylene as shown in above formula $1^{b}$ or a carbonyl as shown in above formula $1^{a}$.

P23

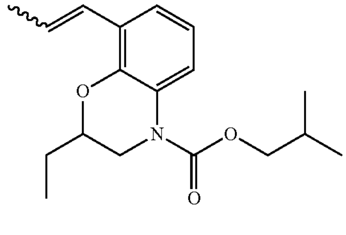

isobutyl 2-ethyl-8-(prop-1-enyl)-2H-benzo[b][1,4] oxazine-4(3H)-carboxylate

Procedure & NMR Data: 392 µL (2.5 eq, 3 mmol) of isobutyl chloroformate was added to a mixture of 192 mg (4 eq, 4.8 mmol) of NaH and 261 mg (1.2 mmol) of oxazine P22 in THF (24 mL). 380 mg of P23 were obtained, yield 99%.

$^{1}$H NMR (400 MHz, $CDCl_3$) δ 7.67-7.49 (m, 1H), 7.01 (ddd, J=47.8, 7.7, 1.5 Hz, 1H), 6.83-6.69 (m, 1H), 6.52 (ddd, J=13.7, 13.0, 1.6 Hz, 1H), 6.24-5.69 (m, 1H), 4.19-3.97 (m, 2H), 3.97-3.86 (m, 2H), 3.29-3.16 (m, 1H), 2.00-1.88 (m, 1H), 1.80 (ddd, J=20.6, 6.9, 1.8 Hz, 3H), 1.02 (dt, J=11.4, 7.5 Hz, 3H), 0.90 (ddd, J=6.7, 3.5, 0.6 Hz, 6H). $^{13}$C NMR (101 MHz, $CDCl_3$) δ 143.83, 143.07, 126.89, 126.64, 126.59, 125.92, 125.56, 125.52, 125.50, 125.25, 124.79, 121.74, 119.49, 118.86, 76.15, 72.39, 45.76, 30.32, 29.70, 27.93, 26.91, 25.66, 25.61, 22.70, 19.20, 19.18, 18.96, 14.77, 9.58, 9.51.

P24

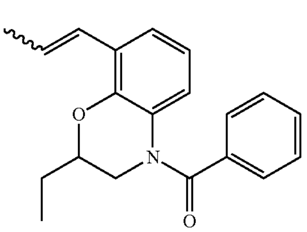

(2-ethyl-8-(prop-1-enyl)-2H-benzo[b][1,4]oxazin-4 (3H)-yl)(phenyl)methanone

Procedure & NMR Data: 348 µL (2.5 eq, 3 mmol) of benzoyl chloride was added to a mixture of 192 mg (4 eq, 4.8 mmol) of NaH and 260 mg (1.2 mmol) of oxazine P22 in THF (25 mL). 300 mg of P24 were obtained, yield 78%.

$^{1}$H NMR (400 MHz, $CDCl_3$) δ 7.46-7.38 (m, 2H), 7.38-7.31 (m, 1H), 7.31-7.22 (m, 2H), 6.98 (ddd, J=42.5, 7.5, 1.2 Hz, 1H), 6.70-6.39 (m, 3H), 6.29-5.72 (m, 1H), 4.28-4.12 (m, 2H), 3.38 (ddd, J=12.8, 7.7, 6.1 Hz, 1H), 1.81 (ddd, J=23.1, 6.9, 1.8 Hz, 3H), 1.76-1.53 (m, 2H), 1.01 (dt, J=14.9, 7.5 Hz, 3H). $^{13}$C NMR (101 MHz, $CDCl_3$) δ 143.31, 135.35, 135.32, 130.61, 130.59, 128.64, 128.60, 128.36, 128.31, 127.27, 127.08, 126.82, 126.27, 126.16, 125.03, 124.47, 123.02, 122.92, 122.56, 119.06, 118.46, 25.99, 18.99, 14.83, 9.59, 9.50.

P25

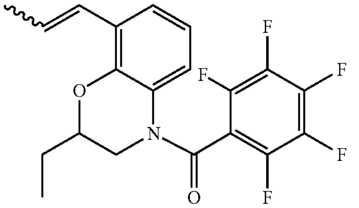

(2-ethyl-8-(prop-1-enyl)-2H-benzo[b][1,4]oxazin-4 (3H)-yl)(perfluorophenyl)methanone Procedure & NMR Data: 141 µL (2 eq, 0.98 mmol) of pentafluorobenzoyl chloride was added to a mixture of 78 mg (4 eq, 1.96 mmol) of NaH and 100 mg (0.49 mmol) of oxazine P22 in THF (11 mL). 118 mg of P25 were obtained, yield 61%.

$^1$H NMR (400 MHz, $CDCl_3$) δ 7.05 (ddd, J=45.1, 7.7, 1.2 Hz, 1H), 6.64-6.37 (m, 2H), 6.28 (ddd, J=18.8, 8.0, 1.1 Hz, 1H), 6.22-5.72 (m, 1H), 4.59 (ddd, J=13.1, 3.1, 1.4 Hz, 1H), 4.28-4.04 (m, 1H), 3.38-3.17 (m, 1H), 1.87-1.64 (m, 5H), 1.06 (dt, J=12.3, 7.5 Hz, 3H). $^{13}$C NMR (101 MHz, $CDCl_3$) δ 156.94, 145.29, 144.49, 128.11, 127.96, 127.81, 127.61, 127.48, 127.27, 127.22, 126.73, 124.80, 124.57, 124.39, 124.21, 123.96, 123.79, 122.08, 121.90, 120.34, 120.17, 119.98, 119.37, 119.18, 118.58, 75.86, 48.65, 44.13, 26.90, 26.12, 26.08, 25.36, 18.94, 14.78, 9.44, 9.35. $^{19}$F NMR (376 MHz, $CDCl_3$) δ −139.59-−140.69 (m, 2F), −150.30-−151.23 (m, 1F), −158.61-−160.29 (m, 2F).

P26

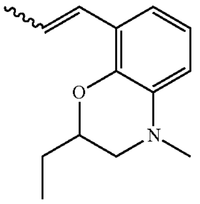

2-ethyl-4-methyl-8-(prop-1-enyl)-3,4-dihydro-2H-benzo[b][1,4]oxazine

Procedure & NMR Data: 287 μL (10 eq, 4.6 mmol) of methyl iodide was added to a mixture of 74 mg (4 eq, 1.84 mmol) of NaH and 100 mg (0.46 mmol) of oxazine P22 in THF (10 mL). 75 mg of P26 were obtained, yield 71%.

$^1$H NMR (400 MHz, $CDCl_3$) δ 6.77-6.64 (m, 2H), 6.63-6.49 (m, 1H), 6.48-6.42 (m, 1H), 6.20-5.65 (m, 1H), 4.03 (tdd, J=7.9, 5.6, 2.5 Hz, 1H), 3.12 (ddd, J=11.3, 3.1, 2.5 Hz, 1H), 2.95-2.87 (m, 1H), 2.82-2.75 (m, 3H), 1.79 (ddd, J=14.4, 6.9, 1.8 Hz, 3H), 1.75-1.50 (m, 2H), 1.02-0.95 (m, 1H)

P27

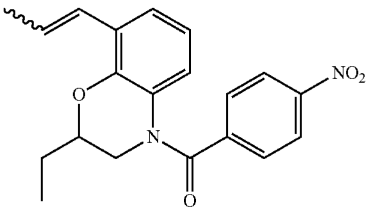

(2-ethyl-8-(prop-1-enyl)-2H-benzo[b][1,4]oxazin-4(3H)-yl)(4-nitrophenyl)methanone Procedure & NMR Data: 199 mg (2.5 eq, 1.08 mmol) of 4-Nitrobenzoyl chloride was added to a mixture of 66 mg (4 eq, 1.72 mmol) of NaH and 87 mg (0.43 mmol) of oxazine P22 in THF (18 mL). 150 mg of P27 were obtained, yield 99%.

$^1$H NMR (400 MHz, $CDCl_3$) δ 8.20-8.04 (m, 2H), 7.65-7.48 (m, 2H), 7.02 (dd, J=43.8, 8.9 Hz, 1H), 6.69-6.38 (m, 2H), 6.27-5.72 (m, 1H), 4.52-4.40 (m, 1H), 4.05 (q, J=7.2 Hz, 2H), 3.30 (ddd, J=13.1, 8.3, 6.7 Hz, 1H), 1.81 (ddd, J=27.4, 6.9, 1.8 Hz, 3H), 1.40 (dd, J=11.6, 6.3 Hz, 2H), 1.18 (t, J=7.1 Hz, 3H): $^{13}$C NMR (101 MHz, $CDCl_3$) δ 171.12, 148.74, 144.29, 143.52, 141.38, 129.64, 127.81, 127.70, 127.21, 127.13, 126.52, 124.73, 124.18, 123.65, 123.60, 123.39, 122.85, 122.71, 119.30, 118.72, 60.37, 21.03, 18.95, 18.67, 14.82, 14.18.

P28

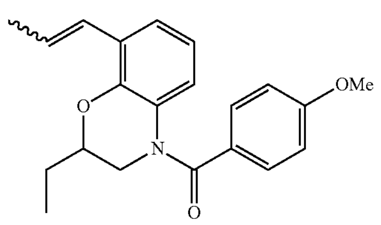

(2-ethyl-8-(prop-1-enyl)-2H-benzo[b][1,4]oxazin-4(3H)-yl)(4-methoxyphenyl)methanone Procedure & NMR Data: 133 mg (2.5 eq, 0.77 mmol) of p-Anisoyl chloride was added to a mixture of 48 mg (4 eq, 1.24 mmol) of NaH and 63 mg (0.31 mmol) of oxazine P22 in THF (12 mL). 103 mg of P28 were obtained, yield 98%.

$^1$H NMR (400 MHz, $CDCl_3$) δ 7.46-7.35 (m, 2H), 7.08-6.89 (m, 1H), 6.84-6.72 (m, 2H), 6.62 (d, J=15.8 Hz, 1H), 6.57-6.41 (m, 2H), 6.27-5.71 (m, 1H), 4.22 (dd, J=23.3, 8.8 Hz, 2H), 3.76 (d, J=3.8 Hz, 3H), 3.37 (dt, J=12.8, 7.6 Hz, 1H), 1.82 (ddd, J=21.5, 6.9, 1.8 Hz, 3H), 1.75-1.56 (m, 2H), 1.01 (dt, J=14.7, 7.5 Hz, 3H). $^{13}$C NMR (101 MHz, $CDCl_3$) δ 168.61, 161.53, 143.93, 130.90, 130.87, 127.21, 127.03, 126.14, 126.00, 125.07, 124.50, 123.00, 122.90, 122.30, 119.07, 118.46, 113.56, 113.51, 77.48, 77.33, 77.01, 76.69, 55.34, 53.42, 26.91, 25.93, 18.99, 14.85, 9.60, 9.51.

P29

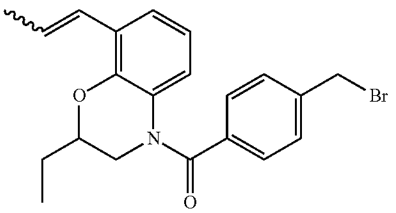

(4-(bromomethyl)phenyl)(2-ethyl-8-(prop-1-enyl)-2H-benzo[b][1,4]oxazin-4(3H)-yl)methanone Procedure & NMR Data: 96 mg (1.5 eq, 0.41 mmol) of 4-(bromomethyl)benzoyl chloride was added to a mixture of 33 μL (1.5 eq, 0.41 mmol) of pyridine and oxazine P22 in DCM (15 mL). 53 mg of P29 were obtained, yield 48%.

$^1$ H NMR (400 MHz, $CDCl_3$) δ 7.47 (q, J=8.30 Hz, 2H), 7.36 (t, J=8.36 Hz, 2H), 7.12 (d, J=9.03 Hz, 1H), 7.01 (d, J=8.68 Hz, 1H), 6.69 (dd, J=15.94, 1.66 Hz, 1H), 6.60 (dd, J=13.96, 6.13 Hz, 1H), 6.53 (dd, J=11.61, 1.63 Hz, 1H), 6.26 (qd, J=15.86, 6.63 Hz, 1H), 5.85 (qd, J=11.61, 7.08 Hz, 1H), 4.47 (s, 2H), 4.37-4.20 (m, 2H), 3.44 (ddd, J=12.82, 7.71, 5.45 Hz, 1H), 1.91 (dd, J=6.66, 1.73 Hz, 3H), 1.85 (dd, J=7.10, 1.85 Hz, 3H), 1.84-1.62 (m, 2H), 1.08 (td, J=14.75, 7.47 Hz, 1H). $^{13}$C NMR (101 MHz, $CDCl_3$) δ 168.1, 144.0, 143.2, 140.2, 140.2, 139.8, 135.2, 135.2, 129.1, 129.1, 129.0, 129.0, 128.9, 128.4, 128.4, 127.25.8, 18.9, 14.8, 9.5, 9.5.

P30

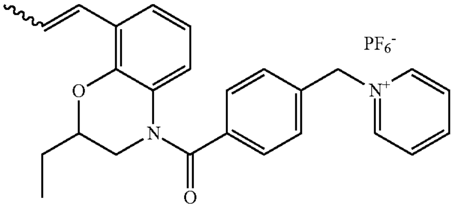

1-(4-(2-ethyl-8-(prop-1-enyl)-3,4-dihydro-2H-benzo[b][1,4]oxazine-4-carbonyl)benzyl)pyridinium hexafluorophosphate(V)

Procedure & NMR Data: 53 mg (0.13 mmol) of oxazine P22 were added to 3004 of pyridine in toluene (15 mL). The mixture warm up to reflux for the night. Volatiles were removed then 17 mg (1.5 eq) of potassium hexafluorophosphate and water (10 mL) were added. 30 mg of P30 were obtained, yield 42%.

$^1$H NMR (400 MHz, $CDCl_3$) δ 8.90 (d, J=5.54 Hz, 2H), 8.52 (t, J=7.77 Hz, 1H), 8.05 (t, J=7.02 Hz, 2H), 7.51 (t, J=7.86 Hz, 2H), 7.44 (t, J=7.85 Hz, 2H), 7.09 (d, J=7.90 Hz, 1H), 6.97 (d, J=7.96 Hz, 1H), 6.61 (dd, J=15.88, 1.46 Hz, 1H), 6.58-6.48 (m, 1H), 6.44 (dd, J=11.57, 1.43 Hz, 1H), 6.21 (qd, J=15.75, 6.51 Hz, 1H), 5.84-5.73 (m, 3H), 4.32-4.02 (m, 2H), 3.43 (ddd, J=12.93, 7.72, 2.55 Hz, 1H), 1.85 (dd, J=6.62, 1.48 Hz, 3H), 1.78 (dd, J=7.09, 1.73 Hz, 3H), 1.75-1.55 (m, 2H), 1.02 (td, J=14.48, 7.44 Hz, 3H). $^{19}$F NMR (376 MHz, $CD_2Cl_2$) δ −73.3 (d, 6F, J=711 Hz) $^{31}$P NMR (162 MHz, CDCl3) δ −144.5 (sept, 1P, J=711 Hz); $^{13}$C NMR (101 MHz, $CDCl_3$) δ 168.0, 145.8, 144.1, 143.8, 143.1, 136.5, 134.5, 129.1, 128.7, 128.6, 128.3, 126.8, 126.7, 126.7, 126.4, 126.0, 124.3, 123.8, 122.7, 122.3, 122.2, 118.6, 118.0, 63.7, 77.6, 46.4, 18.1, 13.9, 8.7, 8.6.

P31

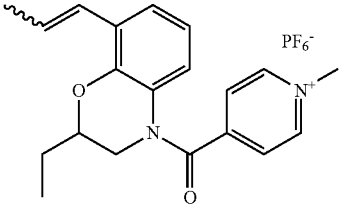

4-(2-ethyl-8-(prop-1-enyl)-3,4-dihydro-2H-benzo[b][1,4]oxazine-4-carbonyl)-1-methylpyridinium hexafluorophosphate(V)

Procedure & NMR Data: 123 mg (2.5 eq, 0.67 mmol) of isonicotinoyl chloride was added to a mixture of 42 mg (4 eq, 1.08 mmol) of NaH and 56 mg (0.27 mmol) of oxazine P22 in DMF (15 mL). 66 mg were purified.

This product was added to 5004 of Iodomethane in toluene (15 mL). This mixture warm up to reflux for the night then cooled to room temperature then volatiles were removed under reduce pressure. Water (15 mL) and 59 mg of potassium hexafluorophosphate (1.5 eq) were added to crude and stirred for 1 h. 62 mg of 31 were obtained, yield 62%.

$^1$H NMR (400 MHz, CDCl3) δ 8.78-8.36 (m, 2H), 8.03-7.62 (m, 2H), 7.10 (d, J=7.35 Hz, 1H), 7.02 (d, J=7.25 Hz, 1H), 6.86-6.61 (m, 1H), 6.56 (dd, J=15.78, 1.51 Hz, 1H), 6.42 (dd, J=11.48, 1.48 Hz, 1H), 6.17 (dd, J=15.71, 6.75 Hz, 1H), 6.26-6.03 (m, 1H), 5.89-5.72 (m, 2H), 4.30 (s, 3H), 4.57-3.91 (m, 2H), 3.37-3.13 (m, 1H), 1.83 (dd, J=6.59, 1.52 Hz, 3H), 1.78 (dd, J=7.09, 1.77 Hz, 3H), 1.75-1.37 (m, 2H), 1.16-0.96 (m, 3H). $^{19}$F NMR (376 MHz, CDCl3 ) δ −72.3 (d, 6F, J=711 Hz). $^{31}$P NMR (162 MHz, CDCl3) δ −144.9 (sept, 1P, J=711 Hz). $^{13}$C NMR (101 MHz, CDCl3) δ 150.7, 146.2, 144.5, 143.7, 127.5, 127.5, 126.1, 124.4, 123.7, 123.6, 119.0, 75.6, 51.0, 48.7, 18.9, 18.4, 14.8, 9.1.

I-F—General Procedure for Ligand Exchange.

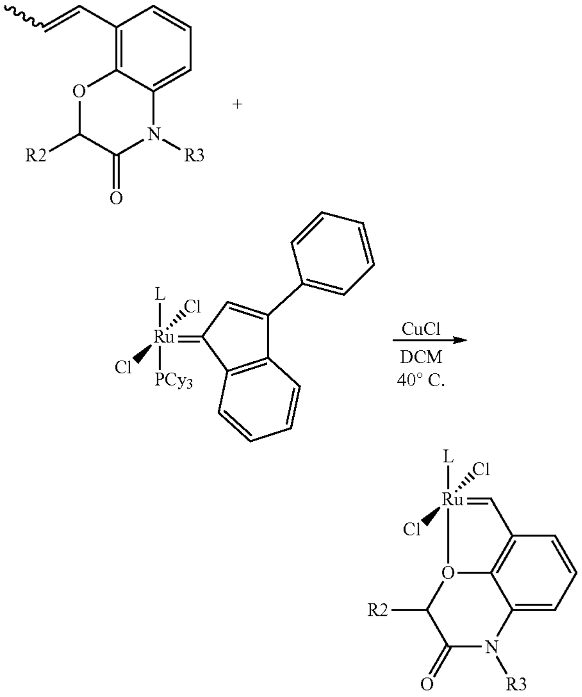

To a solution of SIPr (N,N'-bis(2,6-diisopropylphenyl)imidazol-2-ylidène) (or SIMes (1,3-dimésityl-4,5-dihydroimidazol-2-ylidène)) containing Ru-indenylidene complex (1.2 eq) and copper chloride (1.1 eq) in dry DCM (Dichloromethane) (1 mL for 0.07 mmol of oxazinone), oxazinone in DCM solution (1 mL for 0.035 mmol of oxazinone) was added. The resulting mixture was stirred at 35° C. for 5 h. Volatiles were removed under reduce pressure, acetone was added to the residue and the solution is filtered on a plug of Celite. The filtrate was concentrated and purified by chromatography on silica gel.

Depending on R2 and R3 products P32 to P52 are obtained (attention is drawn to the fact that products P52 to P57 were obtained after amide reduction—see below). See below for specific procedure and NMR data for Catalysts according to the invention P32 to P59.

According to a preferred embodiment, L is a phosphine $P(R8)_3$ or a phosphate $P(OR9)_3$, wherein R8 and R9 are each independently of one another $C_{1-6}$-alkyl, $C_{5-12}$-cycloalkyl or ary.

According to another preferred embodiment, L is a ligand of the formula L1, L2, L3 or L4 as described above and wherein R10 and R11 are each, independently of one another a substituted or an unsubstituted side chain comprising 1 to 30 carbon atoms and optionally comprising one or more functional groups, and wherein R12 and R13 are each, independently of one another, H, $C_{1-6}$-alkyl optionally substituted by a alkoxy radical OR15, or aryl optionally substituted by a alkoxy radical OR15, or form a 3- or 4-membered alkylene bridge, and wherein R15 is selected from the group consisting of $C_{1-20}$-alkyl, aryl and $C_{7-18}$-aralkyl, and wherein g and g' are each halogen, preferably Cl or Br. Particular preference is given when R10 and R11 are each, independently of one another, $C_{1-30}$-alkyl optionally substituted by a alkoxy radical OR15, $C_{2-30}$-alkenyl optionally substituted by a alkoxy radical OR15, aryl optionally substituted by a alkoxy radical OR15, aminoalkyl or aminocycloalkyl.

In a particular preferred embodiment L is a ligand that respond to one of formulae $L1^a$, $L1^b$, $L1^c$, $L1^d$, $L1^e$, $L1^f$ or $L1^g$ as described above.

As mentioned above, it must be noted that from products P23 to P28 are respectively obtained the catalysts of the present invention P52 to P57 (where z is methylene). The general procedure when z is methylene is similar to the one shown in I-F where z is carbonyle. For simplicity the reaction mechanism is not shown herein.

P32

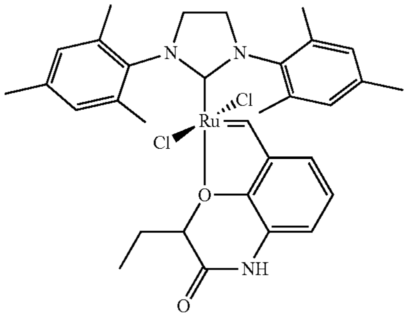

(1,3-dimesitylimidazolidin-2-yl)((2-ethyl-3-oxo-3,4-dihydro-2H-benzo[b][1,4]oxazin-8-yl)methylene) ruthenium(II) chloride Procedure & NMR Data: 50 mg (0.23 mmol) of P2 were added to 218 mg (1 eq, 0.23 mmol) of Umicore-M2 and 25 mg (1.1 eq, 0.25 mmol) of copper chloride in dry DCM (4.6 mL). 20 mg of P32 were obtained, yield 13%.

$^1$H NMR (400 MHz, $CD_2Cl_2$) δ 16.51 (s, 1H), 7.43 (s, 1H), 7.00 (d, J=5.1 Hz, 4H), 6.92 (d, J=7.7 Hz, 1H), 6.85 (dd, J=7.7, 7.6 Hz, 1H), 6.59 (d, J=7.6 Hz, 1H), 4.95-4.88 (m, 1H), 4.11 (s, 4H), 2.36 (s, 6H), 2.33 (d, J=5.5 Hz, 12H), 1.93-1.69 (m, 2H), 0.84-0.64 (m, 3H).

P33

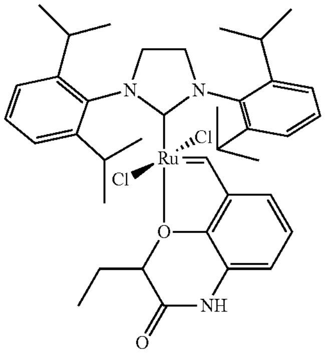

(1,3-bis(2,6-diisopropylphenyl)imidazolidin-2-yl) ((2-ethyl-3-oxo-3,4-dihydro-2H-benzo[b][1,4]oxazin-8-yl)methylene)ruthenium(II) chloride Procedure & NMR Data: 50 mg (0.23 mmol) of P2 were added to 238 mg (1 eq, 0.23 mmol) of SIPr-indenylidene and 25 mg (1.1 eq, 0.25 mmol) of copper chloride in dry DCM (6 mL). 84 mg of P33 were obtained, yield 49%.

$^1$H NMR (400 MHz, $CD_2Cl_2$) δ 16.29 (s, 1H), 7.63 (s, 1H), 7.50-7.42 (m, 2H), 7.33-7.26 (m, 4H), 6.84 (dd, J=7.7, 1.3 Hz, 1H), 6.78 (t, J=7.7 Hz, 1H), 6.47 (dd, J=7.7, 1.3 Hz, 1H), 5.00 (dd, J=5.1, 2.8 Hz, 1H), 4.18-4.08 (m, 4H), 3.54-3.39 (m, 4H), 1.91-1.77 (m, 2H), 1.22-1.07 (m, 24H), 0.81 (t, J=7.3 Hz, 3H).

P34

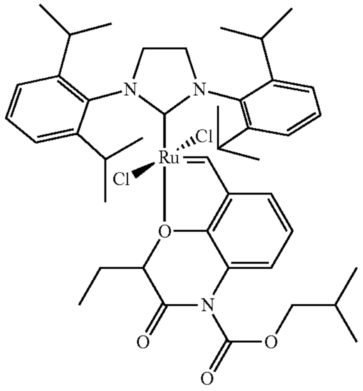

(1,3-bis(2,6-diisopropylphenyl)imidazolidin-2-yl) ((2-ethyl-4-(isobutoxycarbonyl)-3-oxo-3,4-dihydro-2H-benzo[b][1,4]oxazin-8-yl)methylene)ruthenium (II) chloride Procedure & NMR Data: 154 mg (0.48 mmol) of P3 were added to 500 mg (1 eq, 0.48 mmol) of SIPr-indenylidene and 52 mg (1.1 eq, 0.53 mmol) of copper chloride in dry DCM (9 mL). 262 mg of P34 were obtained, yield 64%.

$^1$H NMR (400 MHz, $CD_2Cl_2$) δ 16.29 (s, 1H), 7.46 (t, J=7.7 Hz, 2H), 7.40 (dd, J=8.2, 1.2 Hz, 1H), 7.30 (td, J=7.7, 1.4 Hz, 4H), 6.89 (dd, J=7.7, 8.2 Hz, 1H), 6.60 (dd, J=7.7, 1.2 Hz, 1H), 4.95 (dd, J=5.4, 2.6 Hz, 1H), 4.22-4.06 (m, 4H), 4.03 (dd, J=6.5, 1.9 Hz, 2H), 3.54-3.37 (m, 4H), 1.92 (dt, J=13.5, 6.7 Hz, 1H), 1.88-1.66 (m, 2H), 1.23-1.09 (m, 24H), 0.86 (d, J=6.7 Hz, 6H), 0.83 (t, J=7.3 Hz, 3H).

P35

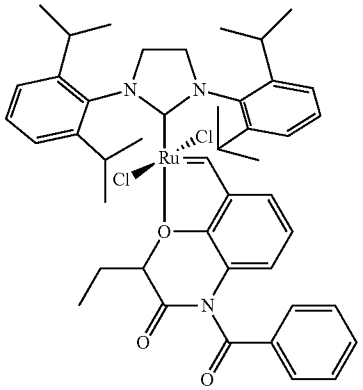

(1,3-bis(2,6-diisopropylphenyl)imidazolidin-2-yl) ((2-ethyl-3-oxo-4-(phenylcarbonyl)-3,4-dihydro-2H-benzo[b][1,4]oxazin-8-yl)methylene)ruthenium(II) chloride Procedure & NMR Data: 58 mg (0.18 mmol) of P4 were added to 187 mg (1 eq, 0.18 mmol) of SIPr-indenylidene and 20 mg (1.1 eq, 0.20 mmol) of copper chloride in dry DCM (5.4 mL). 74 mg of P35 were obtained, yield 48%.

$^1$H NMR (400 MHz, $CD_2Cl_2$) δ 16.33 (s, 1H), 7.72 (dd, J=8.4, 1.3 Hz, 2H), 7.58-7.51 (m, 1H), 7.47 (t, J=7.7 Hz, 2H), 7.41-7.34 (m, 2H), 7.31 (td, J=7.7, 1.5 Hz, 4H), 7.13 (dd, J=8.1, 1.2 Hz, 1H), 6.82 (t, J=7.9 Hz, 1H), 6.59 (dd, J=7.7, 1.3 Hz, 1H), 5.11 (dd, J=5.3, 2.7 Hz, 1H), 4.22-4.07 (m, 4H), 3.57-3.39 (m, 4H), 1.89-1.67 (m, 2H), 1.27-1.11 (m, 24H), 0.84 (t, J=6.8 Hz, 3H).

P36

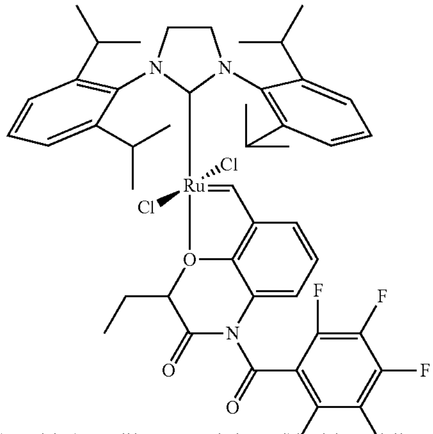

(1,3-bis(2,6-diisopropylphenyl)imidazolidin-2-yl) ((2-ethyl-3-oxo-4-(perfluorophenylcarbonyl)-3,4-dihydro-2H-benzo[b][1,4]oxazin-8-yl)methylene) ruthenium(II) chloride Procedure & NMR Data: 50 mg (0.12 mmol) of P5 were added to 126 mg (1 eq, 0.12 mmol) of SIPr-indenylidene and 13 mg (1.1 eq, 0.13 mmol) of copper chloride in dry DCM (5.4 mL). 68 mg of P36 were obtained, yield 60%.

$^1$H NMR (400 MHz, $CD_2Cl_2$) δ 16.33 (s, 1H), 7.93 (dd, J=8.3, 1.3 Hz, 1H), 7.46 (t, J=7.7 Hz, 2H), 7.30 (td, J=7.7, 1.4 Hz, 4H), 7.05-6.94 (m, 1H), 6.74 (dd, J=7.7, 1.3 Hz, 1H), 5.01 (dd, J=5.0, 3.2 Hz, 1H), 4.26-4.06 (m, 4H), 355-3.36 (m, 4H), 1.87-1.68 (m, 2H), 1.22-1.07 (m, 24H), 0.73 (t, J=7.3 Hz, 3H). $^{19}$F NMR (376 MHz, $CD_2Cl_2$) β −142.62 (2F), −150.67, −161.20 (2F).

P37

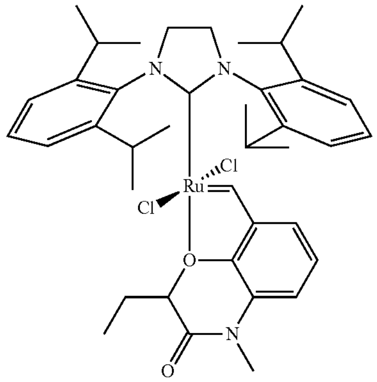

(1,3-bis(2,6-diisopropylphenyl)imidazolidin-2-yl) ((2-ethyl-4-methyl-3-oxo-3,4-dihydro-2H-benzo[b] [1,4]oxazin-8-yl)methylene)ruthenium(II) chloride Procedure & NMR Data: 75 mg (0.33 mmol) of P6 were added to 335 mg (1 eq, 0.33 mmol) of SIPr-indenylidene and 36 mg (1.1 eq, 0.36 mmol) of copper chloride in dry DCM (14 mL). 132 mg of P37 were obtained, yield 52%.

$^1$H NMR (400 MHz, $CD_2Cl_2$) δ 16.30 (s, 1H), 7.46 (t, J=7.7 Hz, 2H), 7.34-7.25 (m, 4H), 7.02 (dd, J=8.0, 1.1 Hz, 1H), 6.89 (dd, J=8.0, 7.7 Hz, 1H), 6.50 (dd, J=7.7, 1.1 Hz, 1H), 4.96 (dd, J=5.0, 2.7 Hz, 1H), 4.24-4.03 (m, 4H), 3.56-3.35 (m, 4H), 3.16 (s, 3H), 1.93-1.58 (m, 2H), 1.22-1.06 (m, 24H), 0.80 (t, J=7.3 Hz, 3H).

P38

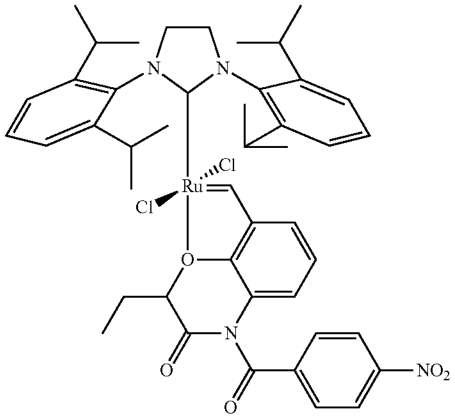

(1,3-bis(2,6-diisopropylphenyl)imidazolidin-2-yl) ((2-ethyl-4-(4-nitrophenylcarbonyl)-3-oxo-3,4-dihydro-2H-benzo[b][1,4]oxazin-8-yl)methylene)ruthenium(II) chloride Procedure & NMR Data: 29 mg (0.08 mmol) of P7 were added to 100 mg (1.2 eq, 0.097 mmol) of SIPr-indenylidene and 11 mg (1.3 eq, 0.11 mmol) of copper chloride in dry DCM (10 mL). 37 mg of P38 were obtained, yield 52%.

$^1$H NMR (400 MHz, $CD_2Cl_2$) δ 16.34 (s, 1H), 8.22-8.14 (m, 2H), 7.83-7.76 (m, 2H), 7.49-7.40 (m, 3H), 7.31 (td, J=7.7, 1.5 Hz, 4H), 6.90 (t, J=7.9 Hz, 1H), 6.67 (dd, J=7.7, 1.3 Hz, 1H), 5.10 (dd, J=5.4, 2.8 Hz, 1H), 4.30-3.98 (m, 4H), 3.61-3.27 (m, 4H), 1.88-1.67 (m, 2H), 1.22-1.10 (m, 24H), 0.81 (t, J=7.3 Hz, 3H).

P39

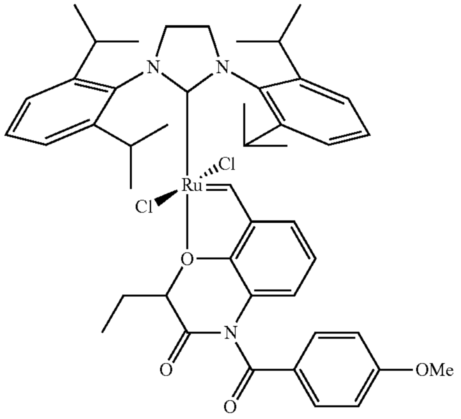

(1,3-bis(2,6-diisopropylphenyl)imidazolidin-2-yl)((2-ethyl-4-(4-methoxyphenylcarbonyl)-3-oxo-3,4-dihydro-2H-benzo[b][1,4]oxazin-8-yl)methylene)ruthenium(II) chloride Procedure & NMR Data: 28 mg (0.08 mmol) of P8 were added to 100 mg (1.2 eq, 0.097 mmol) of SIPr-indenylidene and 11 mg (1.3 eq, 0.11 mmol) of copper chloride in dry DCM (10 mL). 61 mg of P39 were obtained, yield 86%.

$^1$H NMR (400 MHz, Acetone) δ 16.32 (s, 1H), 7.87-7.75 (m, 2H), 7.50-7.40 (m, 2H), 7.35-7.25 (m, 3H), 6.98-6.89 (m, 4H), 6.84 (t, J=7.9 Hz, 1H), 6.52 (dd, J=7.6, 1.2 Hz, 1H), 5.11 (dd, J=5.0, 3.0 Hz, 1H), 4.31-4.15 (m, 4H), 3.77 (s, 3H), 3.62-3.43 (m, 4H), 1.83-1.73 (m, 2H), 1.18-1.05 (m, 24H), 0.80 (t, J=7.3 Hz, 3H).

P40

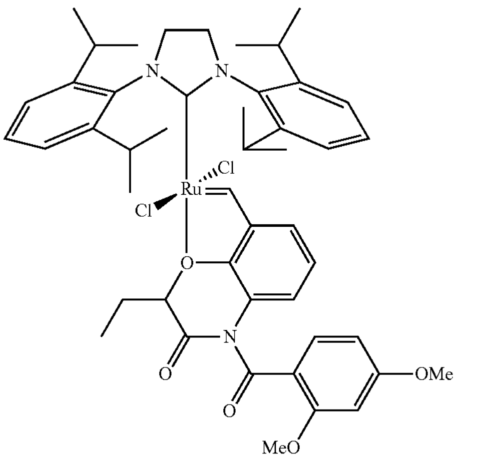

(1,3-bis(2,6-diisopropylphenyl)imidazolidin-2-yl)((4-(2,4-dimethoxyphenylcarbonyl)-2-ethyl-3-oxo-3,4-dihydro-2H-benzo[b][1,4]oxazin-8-yl)methylene)ruthenium(II) chloride Procedure & NMR Data: 31 mg (0.08 mmol) of P9 were added to 100 mg (1.2 eq, 0.097 mmol) of SIPr-indenylidene and 11 mg (1.3 eq, 0.11 mmol) of copper chloride in dry DCM (10 mL). 59 mg of P40 were obtained, yield 80%.

$^1$H NMR (400 MHz, Acetone) δ 16.34 (s, 1H), 7.71 (d, J=8.8 Hz, 1H), 7.45 (t, J=7.7 Hz, 2H), 7.31 (td, J=7.7, 1.5 Hz, 4H), 7.13 (dd, J=8.1, 1.2 Hz, 1H), 6.81 (t, J=7.9 Hz, 1H), 6.56-6.47 (m, 2H), 6.35 (d, J=2.3 Hz, 1H), 4.86 (t, J=4.3 Hz, 1H), 4.28-4.19 (m, 4H), 3.74 (s, 3H), 3.60-3.50 (m, 4H), 3.49 (s, 3H), 1.80-1.71 (m, 2H), 1.18-1.07 (m, 24H), 0.78 (t, J=7.3 Hz, 3H).

P41

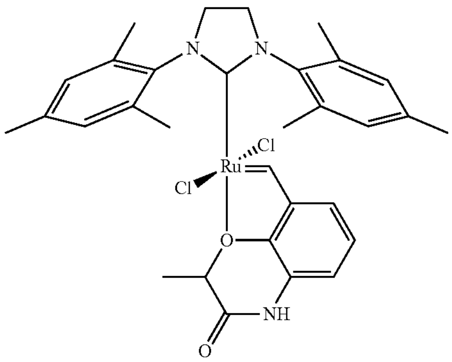

(1,3-dimesitylimidazolidin-2-yl)((2-methyl-3-oxo-3,4-dihydro-2H-benzo[b][1,4]oxazin-8-yl)methylene)ruthenium(II) chloride Procedure & NMR Data: 50 mg (0.25 mmol) of P11 were added to 237 mg (1 eq, 0.25 mmol) of Umicore-M2 and 27 mg (1.1 eq, 0.27 mmol) of copper chloride in dry DCM (4.6 mL). 9 mg of P41 were obtained, yield 6%.

$^1$H NMR (400 MHz, $CD_2Cl_2$) δ 16.46 (s, 1H), 7.93 (s, 1H), 7.00 (s, 4H), 6.82 (d, J=7.2 Hz, 1H), 6.76 (dd, J=7.3, 7.2 Hz, 1H), 6.53 (d, J=7.3 Hz, 1H), 4.89 (q, J=6.5 Hz, 1H), 4.10 (s, J=9.0 Hz, 4H), 2.35 (d, J=2.9 Hz, 12H), 2.32 (s, 6H), 1.12 (d, J=6.5 Hz, 3H).

P42

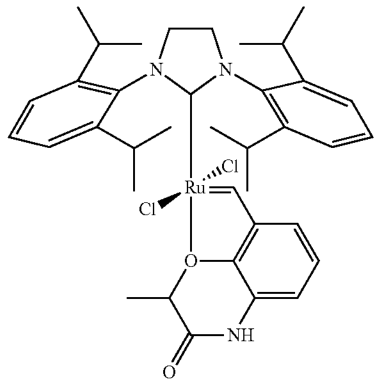

(1,3-bis(2,6-diisopropylphenyl)imidazolidin-2-yl)((2-methyl-3-oxo-3,4-dihydro-2H-benzo[b][1,4]oxazin-8-yl)methylene)ruthenium(II) chloride Procedure & NMR Data: 50 mg (0.25 mmol) of P11 were added to 258 mg (1 eq, 0.25 mmol) of SIPr-indenylidene and 27 mg (1.1 eq, 0.27 mmol) of copper chloride in dry DCM (5.4 mL). 50 mg of P42 were obtained, yield 27%.

$^1$H NMR (400 MHz, $CD_2Cl_2$) δ 16.29 (s, 1H), 8.14 (s, 1H), 7.46 (t, J=7.7 Hz, 2H), 7.30 (td, J=7.7, 1.5 Hz, 4H), 6.63-6.50 (m, 2H), 6.35 (dd, J=7.4, 1.3 Hz, 1H), 4.81 (q, J=6.6 Hz, 1H), 4.19-4.05 (m, 4H), 3.55-3.37 (m, 4H), 1.27 (d, J=6.6 Hz, 3H), 1.21-1.09 (m, 24H).

P43

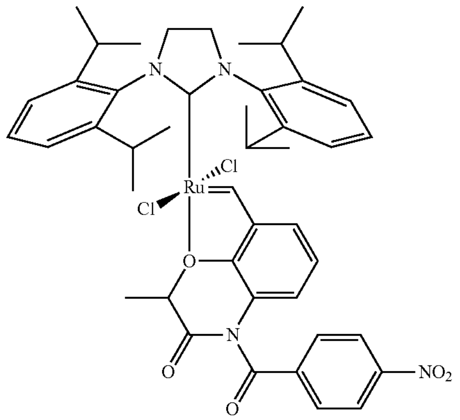

(1,3-bis(2,6-diisopropylphenyl)imidazolidin-2-yl) ((2-methyl-4-(4-nitrophenylcarbonyl)-3-oxo-3,4-dihydro-2H-benzo[b][1,4]oxazin-8-yl)methylene) ruthenium(II) chloride Procedure & NMR Data: 47 mg (0.14 mmol) of P12 were added to 137 mg (1 eq, 0.14 mmol) of SIPr-indenylidene and 15 mg (1.1 eq, 0.15 mmol) of copper chloride in dry DCM (10 mL). 89 mg of P43 were obtained, yield 76%.

$^1$H NMR (400 MHz, Acetone) δ 16.28 (s, 1H), 8.25-8.18 (m, 2H), 8.12-8.05 (m, 2H), 7.45 (t, J=7.7 Hz, 2H), 7.37 (dd, J=8.1, 1.1 Hz, 1H), 7.31 (td, J=7.7, 1.5 Hz, 4H), 6.99-6.90 (m, 1H), 6.62 (dd, J=7.7, 1.1 Hz, 1H), 5.20 (q, J=6.5 Hz, 1H), 4.28-4.16 (m, 4H), 3.62-3.43 (m, 4H), 1.24 (d, J=6.5 Hz, 3H), 1.19-1.05 (m, 24H).

P44

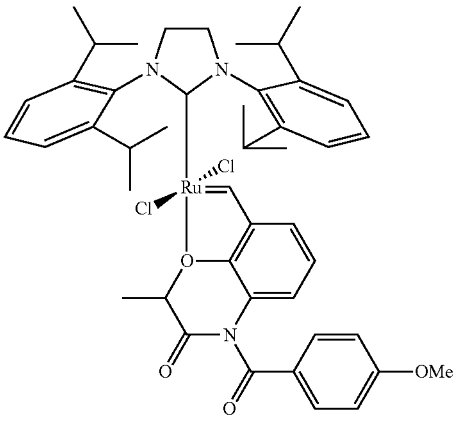

(1,3-bis(2,6-diisopropylphenyl)imidazolidin-2-yl) ((4-(4-methoxyphenylcarbonyl)-2-methyl-3-oxo-3,4-dihydro-2H-benzo[b][1,4]oxazin-8-yl)methylene) ruthenium(II) chloride Procedure & NMR Data: 29 mg (0.087 mmol) of P13 were added to 102 mg (1.2 eq, 0.097 mmol) of SIPr-indenylidene and 11 mg (1.3 eq, 0.11 mmol) of copper chloride in dry DCM (10 ml). 77 mg of P44 were obtained, yield 90%.

$^1$H NMR (400 MHz, Acetone) δ 16.27 (s, 1H), 7.88-7.75 (m, 2H), 7.45 (t, J=7.7 Hz, 2H), 7.31 (td, J=7.7, 1.5 Hz, 4H), 6.97-6.89 (m, 3H), 6.89-6.82 (m, 1H), 6.54 (dd, J=7.6, 1.2 Hz, 1H), 5.16 (q, J=6.5 Hz, 1H), 4.27-4.16 (m, 4H), 3.77 (s, 3H), 3.63-3.43 (m, 4H), 1.29 (d, J=6.5 Hz, 3H), 1.18-1.04 (m, 24H).

P45

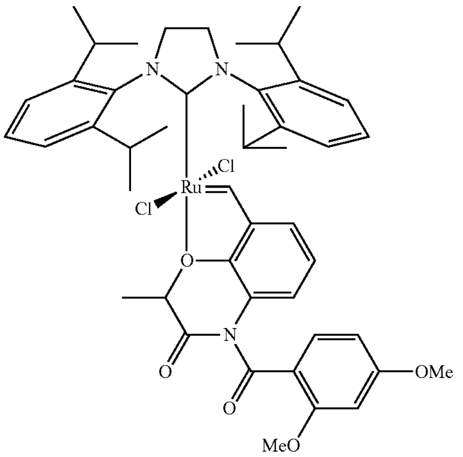

(1,3-bis(2,6-diisopropylphenyl)imidazolidin-2-yl) ((4-(2,4-dimethoxyphenylcarbonyl)-2-methyl-3-oxo-3,4-dihydro-2H-benzo[b][1,4]oxazin-8-yl)methylene)ruthenium(II) chloride Procedure & NMR Data: 32 mg (0.087 mmol) of P14 were added to 102 mg (1.2 eq, 0.097 mmol) of SIPr-indenylidene and 11 mg (1.3 eq, 0.11 mmol) of copper chloride in dry DCM (10 mL). 79 mg of P45 were obtained, yield 95%.

$^1$H NMR (400 MHz, Acetone) δ 16.29 (s, 1H), 7.75-7.66 (m, 1H), 7.45 (t, J=7.7 Hz, 1H), 7.33 (dd, J=7.6, 1.3 Hz, 2H), 7.29 (dt, J=7.6, 1.3 Hz, 4H), 6.84 (t, J=7.9 Hz, 1H), 6.57-6.49 (m, 2H), 6.35 (d, J=2.3 Hz, 1H), 4.94 (q, J=6.5 Hz, 1H), 4.28-4.15 (m, 4H), 3.74 (s, 3H), 3.54 (s, 3H), 3.62-3.42 (m, 4H), 1.33-1.26 (m, 3H), 1.18-1.04 (m, 24H).

P46

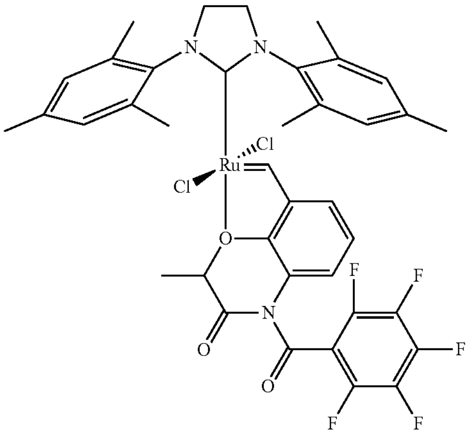

(1,3-dimesitylimidazolidin-2-yl)((2-methyl-3-oxo-4-(perfluorophenylcarbonyl)-3,4-dihydro-2H-benzo[b][1,4]oxazin-8-yl)methylene)ruthenium(II) chloride Procedure & NMR Data: 52 mg (0.13 mmol) of P15 were added to 118 mg (1 eq, 0.13 mmol) of Umicore-M2 and 17 mg (1.1 eq, 0.17 mmol) of copper chloride in dry DCM (10 ml). 69 mg of P46 were obtained, yield 62%.

$^1$H NMR (400 MHz, Acetone) δ 16.45 (s, 1H), 7.92 (dd, J=8.3, 1.0 Hz, 1H), 7.06-6.99 (m, 1H), 6.95 (d, J=9.3 Hz, 4H), 6.80 (dd, J=7.6, 1.0 Hz, 1H), 5.05 (q, J=6.5 Hz, 1H), 4.16 (s, 4H), 2.31 (d, J=10.6 Hz, 12H), 2.26 (s, 6H), 1.07 (d, J=6.5 Hz, 3H). $^{19}$F NMR (376 MHz, Acetone) δ 33.47 (2F), 25.58, 14.45 (2F).

P47

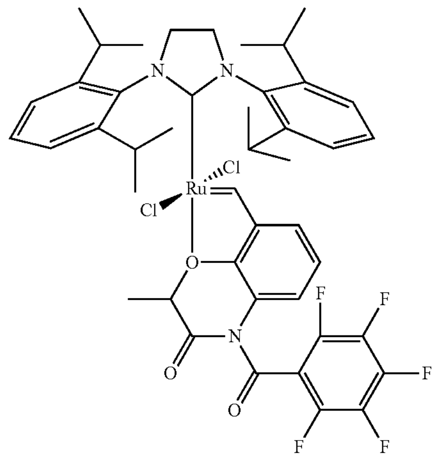

(1,3-bis(2,6-diisopropylphenyl)imidazolidin-2-yl) ((2-methyl-3-oxo-4-(perfluorophenylcarbonyl)-3,4-dihydro-2H-benzo[b][1,4]oxazin-8-yl)methylene) ruthenium(II)chloride Procedure & NMR Data: 50 mg (0.13 mmol) of P15 were added to 137 mg (1 eq, 0.13 mmol) of SIPr-indenylidene and 14 mg (1.1 eq, 0.14 mmol) of copper chloride in dry DCM (10 mL). 99 mg of P47 were obtained, yield 92%.

$^{1}$H NMR (400 MHz, Acetone) δ 16.27 (s, 1H), 7.87 (dd, J=8.3, 1.2 Hz, 1H), 7.44 (t, J=7.7 Hz, 2H), 7.32 (dd, J=7.7, 1.5 Hz, 2H), 7.27 (dd, J=7.7, 1.5 Hz, 2H), 7.06-6.98 (m, 1H), 6.71 (dd, J=7.7, 1.2 Hz, 1H), 5.07 (q, J=6.5 Hz, 1H), 4.33-4.14 (m, 4H), 3.64-3.39 (m, 4H), 1.26 (d, J=6.5 Hz, 3H), 1.18-1.04 (m, 24H). $^{19}$F NMR (376 MHz, Acetone) δ 33.56 (2F), 25.62, 14.37 (2F).

P48

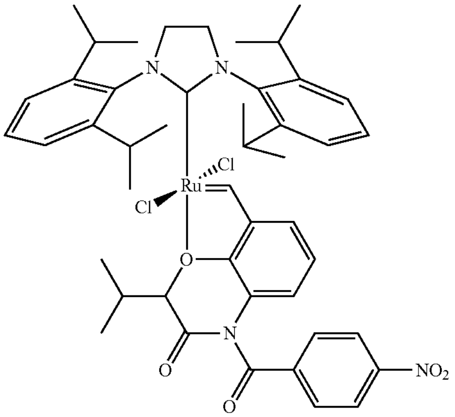

(1,3-bis(2,6-diisopropylphenyl)imidazolidin-2-yl) ((2-isopropyl-4-(4-nitrophenylcarbonyl)-3-oxo-3,4-dihydro-2H-benzo[b][1,4]oxazin-8-yl)methylene) ruthenium(II) chloride Procedure & NMR Data: 19 mg (0.05 mmol) of P18 were added to 61 mg (1.2 eq, 0.059 mmol) of SIPr-indenylidene and 11 mg (1.3 eq, 0.11 mmol) of copper chloride in dry DCM (10 mL). 39 mg of P48 were obtained, yield 85%.

$^{1}$H NMR (400 MHz, Acetone) δ 16.32 (s, 1H), 8.30-8.20 (m, 2H), 8.09-8.01 (m, 2H), 7.46 (t, J=7.7 Hz, 2H), 7.41 (dd, J=8.2, 1.2 Hz, 1H), 7.34-7.28 (m, 4H), 6.94-6.85 (m, 1H), 6.60 (dd, J=7.7, 1.2 Hz, 1H), 5.01 (d, J=2.6 Hz, 1H), 4.30-4.23 (m, 4H), 3.58-3.43 (m, 4H), 2.10-2.03 (m, 1H), 1.18-1.05 (m, 24H), 0.84 (d, J=7.2 Hz, 3H), 0.80 (d, J=6.8 Hz, 3H).

P49

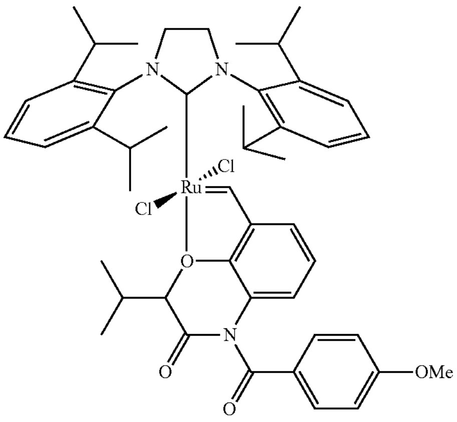

(1,3-bis(2,6-diisopropylphenyl)imidazolidin-2-yl) ((2-isopropyl-4-(4-methoxyphenylcarbonyl)-3-oxo-3,4-dihydro-2H-benzo[b][1,4]oxazin-8-yl)methylene)ruthenium(II) chloride Procedure & NMR Data: 30 mg (0.08 mmol) of P19 were added to 100 mg (1.2 eq, 0.097 mmol) of SIPr-indenylidene and 11 mg (1.3 eq, 0.11 mmol) of copper chloride in dry DCM (10 mL). 70 mg of P49 were obtained, yield 98%.

$^{1}$H NMR (400 MHz, Acetone) δ 16.32 (s, 1H), 7.83-7.78 (m, 2H), 7.46 (t, J=7.7 Hz, 2H), 7.33-7.27 (m, 4H), 6.96-6.91 (m, 3H), 6.83 (t, J=7.9 Hz, 1H), 6.51 (dd, J=7.7, 1.3 Hz, 1H), 4.99 (d, J=2.5 Hz, 1H), 4.29-4.19 (m, 4H), 3.78 (s, 3H), 3.58-3.45 (m, 4H), 2.10-2.04 (m, 1H), 1.18-1.05 (m, 24H), 0.91 (d, J=7.1 Hz, 3H), 0.85 (d, J=6.8 Hz, 3H).

P50

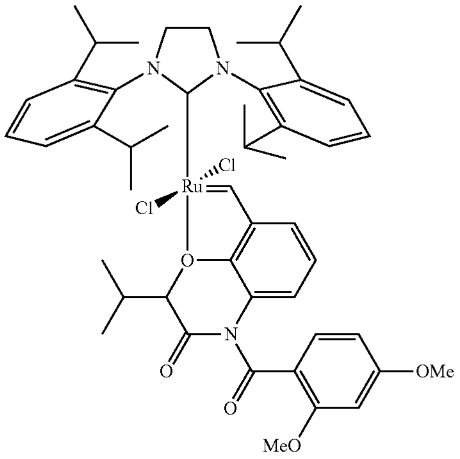

(1,3-bis(2,6-diisopropylphenyl)imidazolidin-2-yl) ((4-(2,4-dimethoxyphenylcarbonyl)-2-isopropyl-3-oxo-3,4-dihydro-2H-benzo[b][1,4]oxazin-8-yl)methylene)ruthenium(II) chloride Procedure & NMR Data: 30 mg (0.08 mmol) of P20 were added to 100 mg (1.2 eq, 0.097 mmol) of SIPr-indenylidene and 11 mg (1.3 eq, 0.11 mmol) of copper chloride in dry DCM (10 mL). 73 mg of P50 were obtained, yield 98%.

$^{1}$H NMR (400 MHz, Acetone) δ 16.34 (s, 1H), 7.76-7.68 (m, 1H), 7.45 (t, J=7.7 Hz, 2H), 7.34-7.28 (m, 4H), 7.00 (dd, J=8.1, 1.2 Hz, 1H), 6.79 (t, J=7.9 Hz, 2H), 6.55-6.51 (m, 1H), 6.49 (dd, J=7.7, 1.2 Hz, 1H), 6.35 (d, J=2.3 Hz, 1H), 4.81 (d, J=2.5 Hz, 1H), 4.30-4.20 (m, 4H), 3.74 (s, 3H), 3.57-3.48 (m, 4H), 3.46 (s, 3H), 2.09-2.04 (m, 1H), 1.18-1.06 (m, 24H), 0.90 (d, J=7.1 Hz, 3H), 0.83 (d, J=6.8 Hz, 3H).

P51

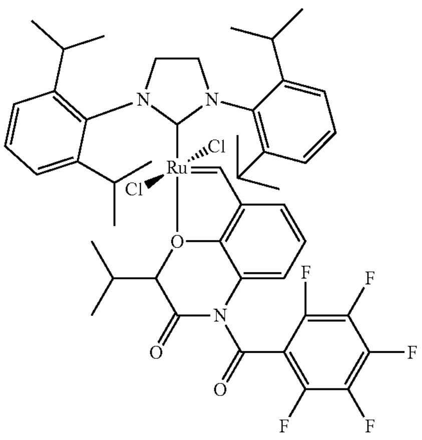

(1,3-bis(2,6-diisopropylphenyl)imidazolidin-2-yl) ((2-isopropyl-3-oxo-4-(perfluorophenylcarbonyl)-3, 4-dihydro-2H-benzo[b][1,4]oxazin-8-yl)methylene) ruthenium(II) chloride Procedure & NMR Data: 32 mg (0.076 mmol) of P21 were added to 95 mg (1.2 eq, 0.092 mmol) of SIPr-indenylidene and 11 mg (1.3 eq, 0.11 mmol) of copper chloride in dry DCM (10 mL). 42 mg of P51 were obtained, yield 59%.

$^{1}$H NMR (400 MHz, Acetone) δ 16.31 (s, 1H), 7.99 (dd, J=8.3, 1.3 Hz, 1H), 7.46 (t, J=7.7 Hz, 2H), 7.31 (ddd, J=13.2, 7.7, 1.4 Hz, 4H), 7.07-6.99 (m, 1H), 6.71 (dd, J=7.7, 1.3 Hz, 1H), 4.95 (d, J=2.7 Hz, 1H), 4.29-4.16 (m, 4H), 3.58-3.39 (m, 4H), 2.12-2.02 (m, 1H), 1.18-1.04 (m, 24H), 0.81 (d, J=7.1 Hz, 3H), 0.74 (d, J=6.9 Hz, 3H). $^{19}$F NMR (376 MHz, Acetone) δ −144.00 (2F), −152.28, −163.04 (2F).

P52

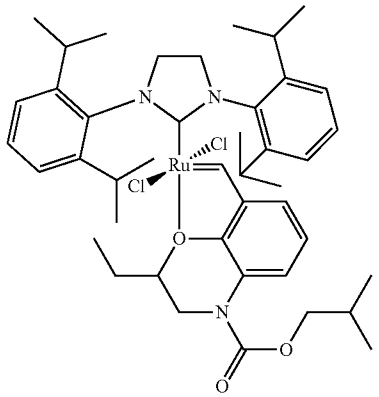

(1,3-bis(2,6-diisopropylphenyl)imidazolidin-2-yl) ((2-ethyl-4-(isobutoxycarbonyl)-3,4-dihydro-2H-benzo[b][1,4]oxazin-8-yl)methylene)ruthenium(II) chloride Procedure & NMR Data: 50 mg (0.17 mmol) of P23 were added to 170 mg (1 eq, 0.17 mmol) of SIPr-indenylidene and 18 mg (1.1 eq, 0.18 mmol) of copper chloride in dry DCM (5.2 mL). 59 mg of P52 were obtained, yield 43%.

$^{1}$H NMR (400 MHz, $CD_2Cl_2$) δ 16.22 (s, 1H), 8.04-7.93 (m, 1H), 7.45 (t, J=7.7 Hz, 2H), 7.29 (d, J=7.7 Hz, 4H), 6.82-6.73 (m, 1H), 6.53 (dd, J=7.6, 1.3 Hz, 1H), 4.23 (dd, J=13.9, 2.2 Hz, 1H), 4.13-4.06 (m, 5H), 3.92-3.79 (m, 2H), 3.54-3.41 (m, 4H), 3.22 (dd, J=13.9, 8.5 Hz, 1H), 1.92-1.75 (m, 2H), 1.17 (d, J=7.0 Hz, 24H), 0.84 (dd, J=6.7, 1.4 Hz, 6H), 0.75 (t, J=7.6 Hz, 3H).

P53

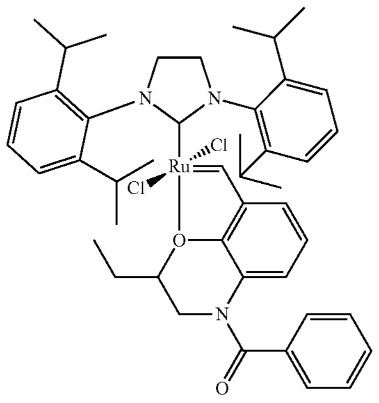

(1,3-bis(2,6-diisopropylphenyl)imidazolidin-2-yl) ((2-ethyl-4-(phenylcarbonyl)-3,4-dihydro-2H-benzo [b][1,4]oxazin-8-yl)methylene)ruthenium(II) chloride Procedure & NMR Data: 50 mg (0.16 mmol) of P24 were added to 170 mg (1 eq, 0.16 mmol) of SIPr-indenylidene and 18 mg (1.1 eq, 0.18 mmol) of copper chloride in dry DCM (5.2 mL). 30 mg of P53 were obtained, yield 22%.

$^{1}$H NMR (400 MHz, $CD_2Cl_2$) δ 16.24 (s, 1H), 7.45 (t, J=7.7 Hz, 2H), 7.40-7.32 (m, 4H), 7.31-7.25 (m, 6H), 6.61-6.50 (m, 2H), 4.37-4.26 (m, 1H), 4.17-4.05 (m, 4H), 4.01-3.92 (m, 1H), 3.58-3.53 (m, 1H), 3.53-3.42 (m, 4H), 1.88-1.76 (m, 2H), 1.25-1.06 (m, 24H), 0.64 (t, J=7.6 Hz, 3H).

P54

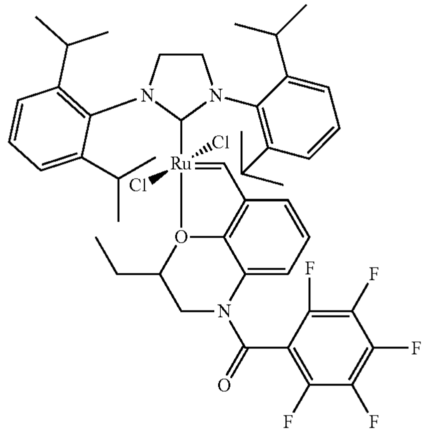

(1,3-bis(2,6-diisopropylphenyl)imidazolidin-2-yl) ((2-ethyl-4-(perfluorophenylcarbonyl)-3,4-dihydro-2H-benzo[b][1,4]oxazin-8-yl)methylene)ruthenium (II) chloride Procedure & NMR Data: 118 mg (0.297 mmol) of P25 were added to 307 mg (1 eq, 0.297 mmol) of SIPr-indenylidene and 32 mg (1.1 eq, 0.32 mmol) of copper chloride in dry DCM (13.4 mL). 125 mg of P54 were obtained, yield 45%.

$^{1}$H NMR (400 MHz, $CD_2Cl_2$) δ 16.22 (d, J=6.6 Hz, 1H), 7.45 (t, J=7.7 Hz, 2H), 7.29 (d, J=7.7 Hz, 4H), 7.22-6.82 (m, 1H), 6.72-6.59 (m, 1H), 6.57-6.44 (m, 1H), 4.33-4.21 (m, 1H), 4.16-4.04 (m, 4H), 3.70-3.59 (m, 1H), 3.57-3.41 (m, 4H), 3.41-3.29 (m, 1H), 1.96-1.71 (m, 2H), 1.27-1.02 (m, 24H), 0.60 (t, J=7.6 Hz, 3H). $^{19}$F NMR (376 MHz, Acetone) δ −142.94 (2F), −154.00, −161.93, (2F).

P55

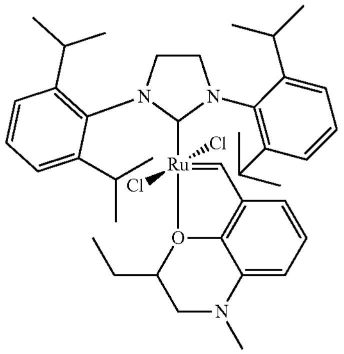

(1,3-bis(2,6-diisopropylphenyl)imidazolidin-2-yl) ((2-ethyl-4-methyl-3,4-dihydro-2H-benzo[b][1,4] oxazin-8-yl)methylene)ruthenium(II) chloride Procedure & NMR Data: 39 mg (0.18 mmol) of P26 were added to 186 mg (1 eq, 0.18 mmol) of SIPr-indenylidene and 20 mg (1.1 eq, 0.20 mmol) of copper chloride in dry DCM (5.5 mL). 34 mg of P55 were obtained, yield 25%.

$^1$H NMR (400 MHz, $CD_2Cl_2$) δ 16.22 (s, 1H), 7.44 (t, J=7.7 Hz, 2H), 7.28 (dt, J=7.7, 1.5 Hz, 4H), 6.71 (dd, J=8.0, 1.7 Hz, 1H), 6.68 (d, J=7.2 Hz, 1H), 6.14 (dd, J=7.2, 1.7 Hz, 1H), 4.32-4.17 (m, 1H), 4.13-4.05 (m, 4H), 3.56-3.41 (m, 4H), 3.16 (dd, J=12.1, 2.3 Hz, 1H), 3.01 (dd, J=12.1, 9.2 Hz, 1H), 2.74 (s, 3H), 1.80-1.68 (m, 2H), 1.20-1.06 (m, 24H), 0.70 (t, J=7.6 Hz, 4H).

P56

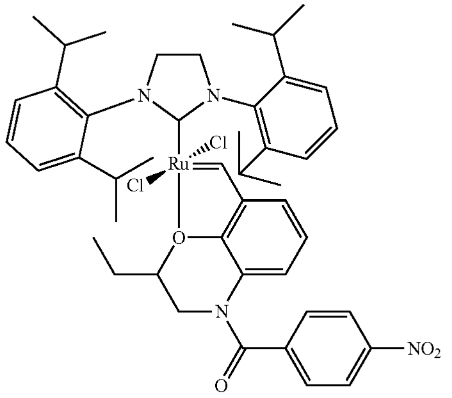

(1,3-bis(2,6-diisopropylphenyl)imidazolidin-2-yl) ((2-ethyl-4-(4-nitrophenylcarbonyl)-3,4-dihydro-2H-benzo[b][1,4]oxazin-8-yl)methylene)ruthenium(II) chloride Procedure & NMR Data: 27 mg (0.077 mmol) of P27 were added to 100 mg (1.2 eq, 0.097 mmol) of SIPr-indenylidene and 11 mg (1.3 eq, 0.11 mmol) of copper chloride in dry DCM (10 mL). 65 mg of P56 were obtained, yield 92%.

$^1$H NMR (400 MHz, Acetone) δ 16.32 (s, 1H), 8.35-8.29 (m, 2H), 7.87-7.78 (m, 3H), 7.56 (t, J=7.7 Hz, 2H), 7.46-7.39 (m, 4H), 6.82 (t, J=7.7 Hz, 1H), 6.66 (dd, J=7.6, 1.1 Hz, 1H), 4.68-4.55 (m, 1H), 4.37-4.26 (m, 4H), 4.15 (d, J=13.1 Hz, 1H), 3.73-3.62 (m, 4H), 3.59 (dd, J=13.1, 8.6 Hz, 1H), 1.87-1.64 (m, 2H), 1.32-1.15 (m, 27H).

P57

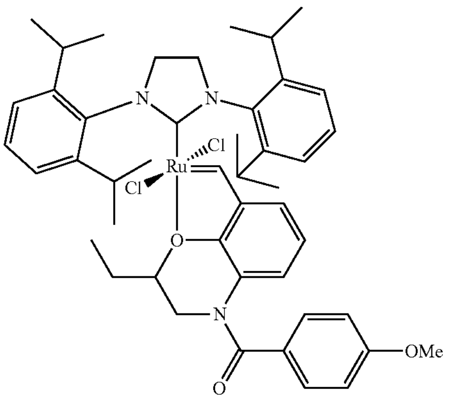

(1,3-bis(2,6-diisopropylphenyl)imidazolidin-2-yl) ((2-ethyl-4-(4-methoxyphenylcarbonyl)-3,4-dihydro-2H-benzo[b][1,4]oxazin-8-yl)methylene)ruthenium (II) chloride Procedure & NMR Data: 27 mg (0.077 mmol) of P28 were added to 100 mg (1.2 eq, 0.097 mmol) of SIPr-indenylidene and 11 mg (1.3 eq, 0.11 mmol) of copper chloride in dry DCM (10 mL). 62 mg of P57 were obtained, yield 89%.

$^1$H NMR (400 MHz, Acetone) δ 16.21 (s, J=9.5 Hz, 1H), 7.42 (t, J=7.7 Hz, 2H), 7.38-7.32 (m, 3H), 7.31-7.24 (m, 4H), 6.86-6.79 (m, 2H), 6.60 (t, J=7.9 Hz, 1H), 6.46 (dd, J=7.6, 1.3 Hz, 1H), 4.34-4.23 (m, 1H), 4.22-4.12 (m, 4H), 3.94 (dd, J=13.7, 2.5 Hz, 1H), 3.75-3.68 (m, 4H), 3.62-3.48 (m, 4H), 1.73-1.50 (m, 2H), 1.19-1.03 (m, 24H), 0.60 (t, J=7.6 Hz, 3H).

P58

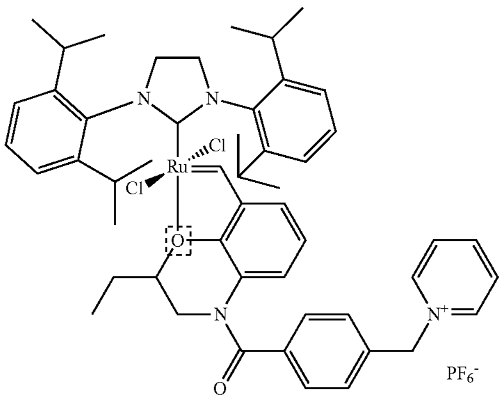

(1,3-bis(2,6-diisopropylphenyl)imidazolidin-2-yl) ((2-ethyl-3-oxo-4-(4-(pyridinium-1-ylmethyl)phenylcarbonyl)-3,4-dihydro-2H-benzo[b][1,4]oxazin-8-yl)methylene)ruthenium(II)dichloride hexafluorophosphate(V)

Procedure & NMR Data: 14 mg (0.025 mmol) of P30 were added to 35 mg (1.2 eq, 0.34 mmol) of SIPr-indenylidene and 3.5 mg (1.3 eq, 0.035 mmol) of copper chloride in dry DCM (4 mL). 13 mg of P58 were obtained, yield 48%.

$^1$H NMR (400 MHz, CD2Cl2) 616.33 (s, 1H), 8.69 (d, J=5.62 Hz, 2H), 8.47 (t, J=7.81 Hz, 1H), 8.01 (dd, J=7.59, 6.74 Hz, 2H), 7.74-7.16 (m, 13H), 6.64 (s, 2H), 4.44-4.33 (m, 1H), 4.22-4.15 (m, 4H), 4.02 (d, J=13.01 Hz, 1H), 3.70-3.60 (m, 1H), 3.55 (dt, J=13.48, 6.37 Hz, 4H), 1.97-1.77 (m, 1H), 1.55-1.45 (m, 1H), 1.28-1.14 (m, 24H), 0.72 (t, J=7.50 Hz, 3H). $^{19}$F NMR (376 MHz, CD2Cl2) δ −72.6 (d, 6F, J=711 Hz). $^{31}$P NMR (162 MHz, CD2Cl2) δ −144.5 (sept, 1P, J=711 Hz)

P59

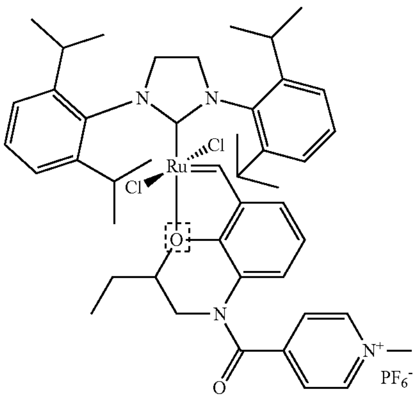

(1,3-bis(2,6-diisopropylphenyl)imidazolidin-2-yl) ((2-ethyl-4-(1-methylpyridin-4-iumcarbonyl)-3,4-dihydro-2H-benzo[b][1,4]oxazin-8-yl)methylene) ruthenium(II)dichloride hexafluorophosphate(V)

Procedure & NMR Data: 23 mg (0.05 mmol) of P31 were added to 68 mg (1.2 eq, 0.066 mmol) of SIPr-indenylidene and 6.5 mg (1.3 eq, 0.065 mmol) of copper chloride in dry DCM (7 mL). 8 mg of P59 were obtained, yield 15%.

$^{1}$H NMR (400 MHz CD2Cl2) δ 16.34 (s, 1H), 8.52 (s, 2H), 7.89 (d, J=5.50 Hz, 2H), 7.85-7.56 (m, 2H), 7.53 (t, J=7.73, 7.73 Hz, 2H), 7.48-7.39 (m, 1H), 7.39-7.31 (m, 4H), 6.73 (d, J=6.76

Hz, 1H), 4.65-4.40 (m, 1H), 4.34 (s, 3H), 4.19 (qd, J=8.53, 4.26, 4.26, 4.26 Hz, 4H), 3.75-3.59 (m, 1H), 3.52 (tt, J=13.34, 13.34, 6.72, 6.72 Hz, 4H), 3.45-3.29 (m, 1H), 1.45-1.27 (m, 2H), 1.29-1.10 (m, 24H), 0.91 (t, J=7.31, 7.31 Hz, 3H). $^{19}$F NMR (376 MHz, CD2Cl2) δ −73.0 (d, 6F, J=712 Hz). $^{31}$P NMR (162 MHz, CD2Cl2) δ −114.8 (sept, 1P, J=711 Hz).

Kinetic and Stability Studies

Chosen synthesized catalysts according to the invention were tested on performance and stability.

Kinetic studies were performed on diethyl 2-allyl-2-(2-methylallyl)propanedioate P60 in NMR tube.

A NMR tube equipped with a septum was filled with diethylallylmethallyl malonate P60 (25.4 mg, 0.1 mmol) and $CD_2Cl_2$ (0.90 mL) under argon. The sample was equilibrated at 30° C. in the NMR probe. The sample was locked and shimmed before the catalyst addition (0.1 mL, 1 μmol, 0.01 M solution of catalyst). The reaction progress was monitored in NMR by the periodical acquisition of data over 1 h and integrating the characteristic signals for allylic proton resonances

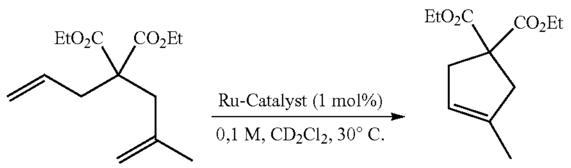

P60 P61

Figure 1:
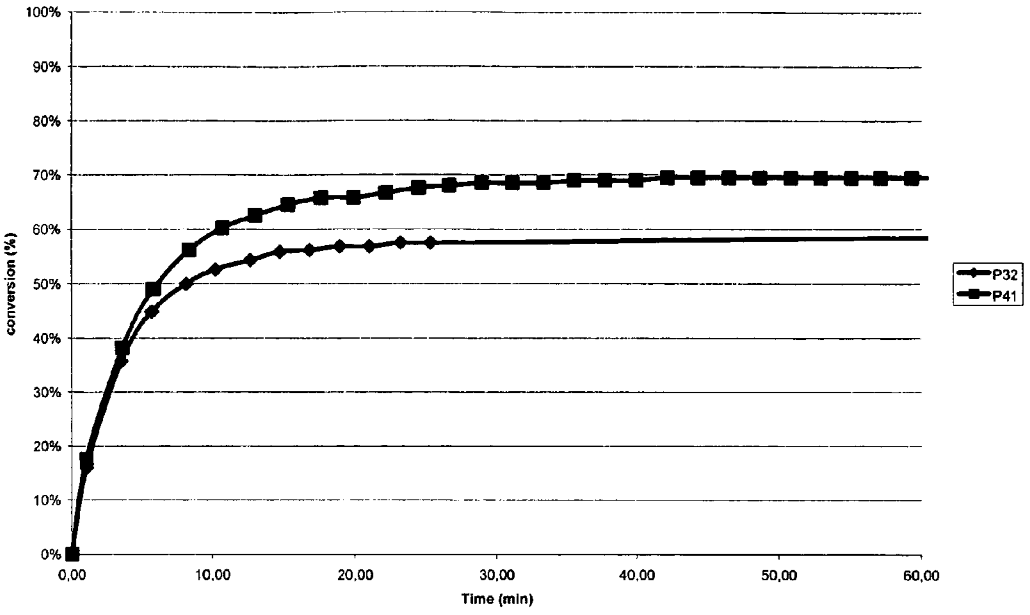
FIG. 1 is a graph showing the conversion rate over time of a product P60 into a product P61 a by a metathesis reaction and in the presence of catalysts P32 and P41 according to the present invention. The conversion rate of P60 to P61 reflects high catalytic activity of the compounds of the present invention.
Figure 2:
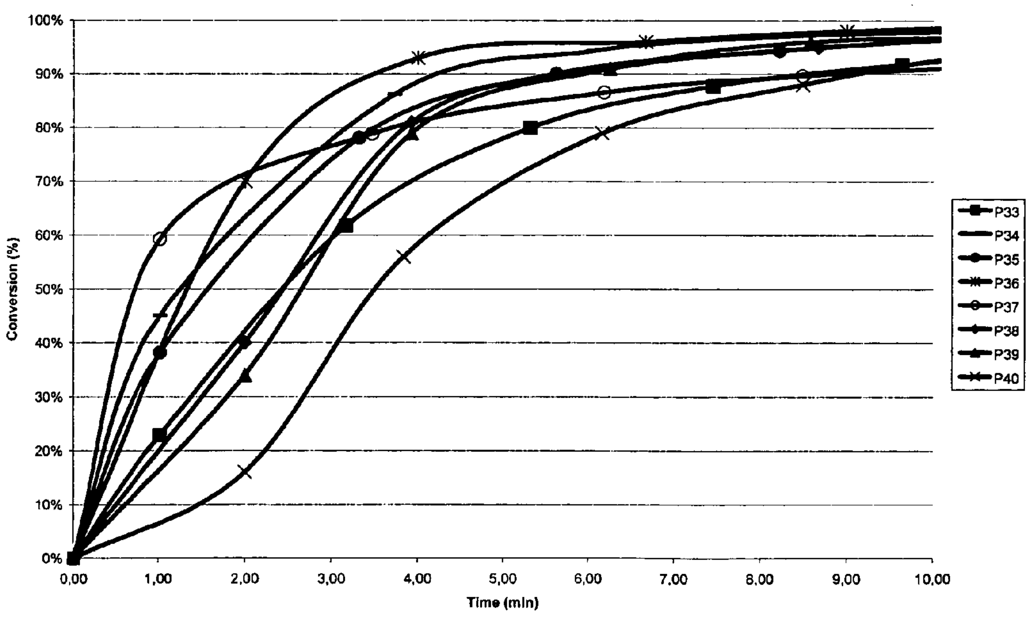
FIG. 2 is a graph showing the conversion rate over time of the product P60 into the product P61 by a metathesis reaction and in the presence of catalysts P33, P34, P35, P36 P37, P38, P39 and P40 according to the present invention. The conversion rate of P60 to P61 reflects high catalytic activity of the compounds of the present invention.
Figure 3:
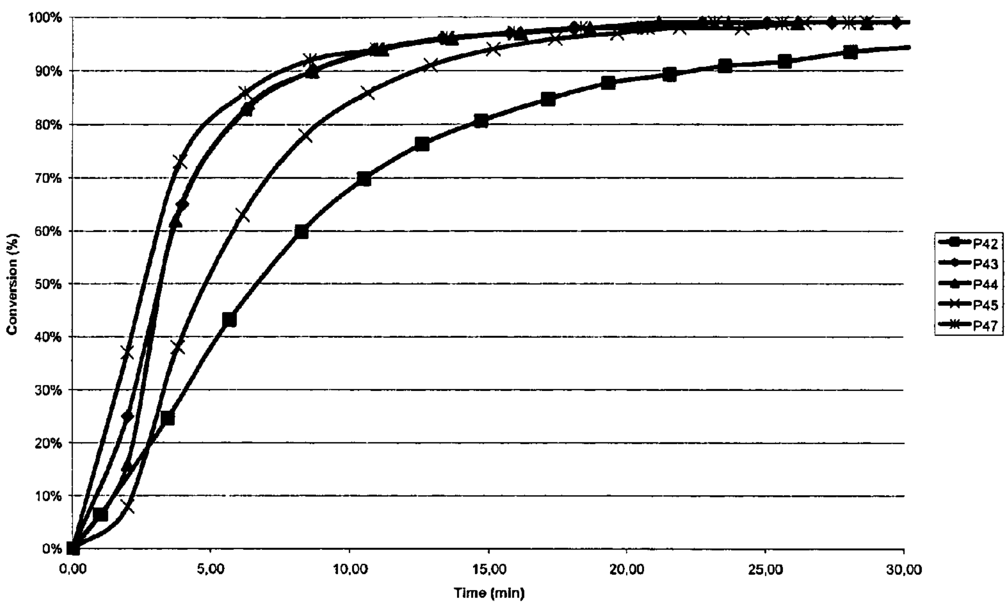
FIG. 3 is a graph showing the conversion rate over time of the product P60 into the product P61 by a metathesis reaction and in the presence of catalysts P42, P43, P44, P45 and P47 according to the present invention. The conversion rate of P60 to P61 reflects high catalytic activity of the compounds of the present invention.
Figure 4:
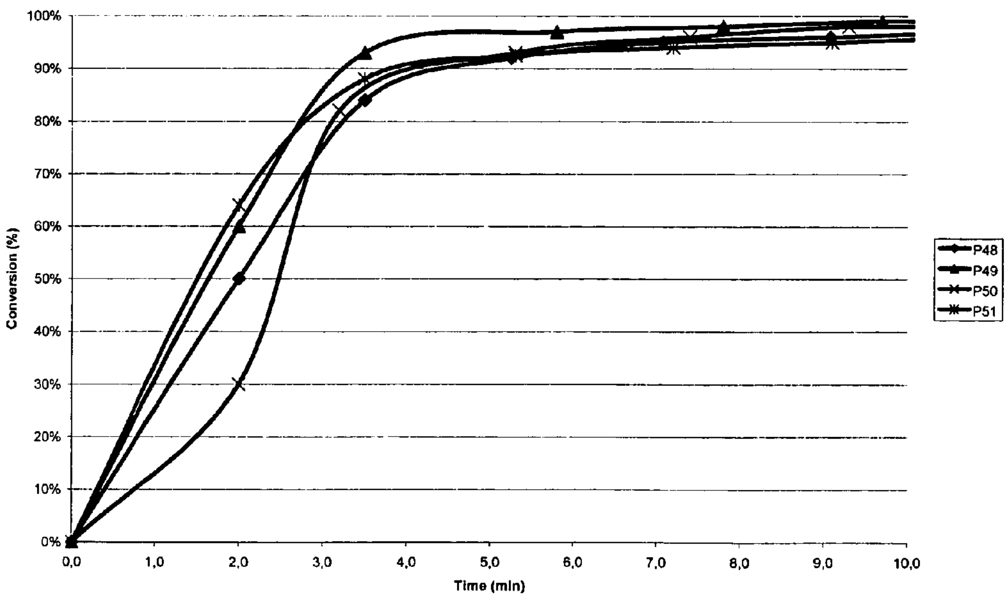
FIG. 4 is a graph showing the conversion rate over time of the product P60 into the product P61 by a metathesis reaction and in the presence of catalysts P48, P49, P50 and P51 according to the present invention. The conversion rate of P60 to P61 reflects high catalytic activity of the compounds of the present invention.
Figure 5:
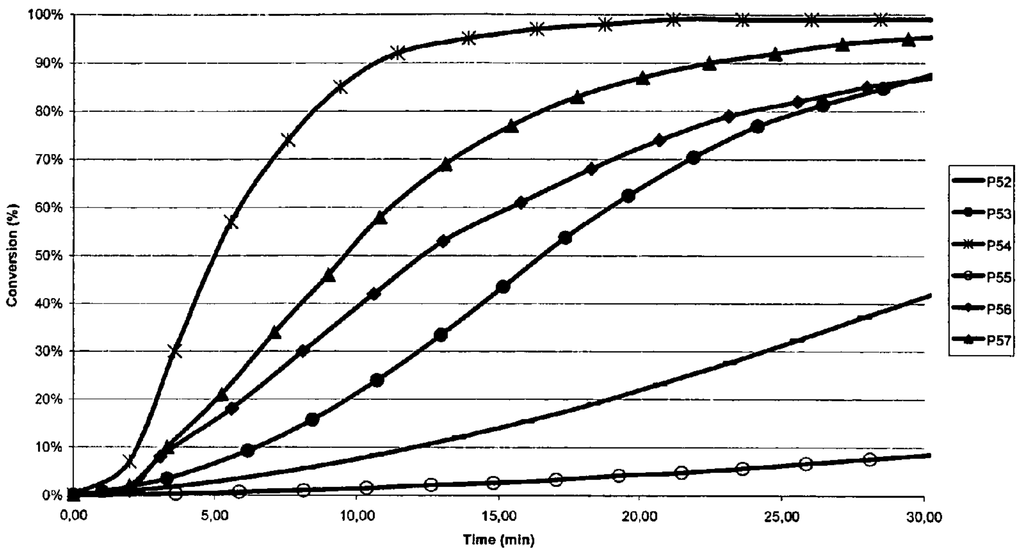

FIG. 5 is a graph showing the conversion rate over time of the product P60 into the product P61 by a metathesis reaction and in the presence of catalysts P52, P53, P54, P55, P56 and P57 according to the present invention. The conversion rate of P60 to P61 reflects high catalytic activity of most compounds of the present invention. It is noted that compounds P52 and P55 show lower activity than P53, P54, P56, P57. These Compounds can be used in appropriate chemical reactions that need to be performed in the presence of moderate catalyst.

Further, FIG. 5 clearly reflects how the compounds of the present invention can be designed for performance control. This is mainly due to the side chains (R1, R2, R3, a, b and c). Indeed the compounds of FIG. 5 show an identical ligand L and greatly differ in their side chain R1. By simply alternating said side chain R1, a significant catalytic activity difference is observed between each compound of FIG. 5.

Figure 6:
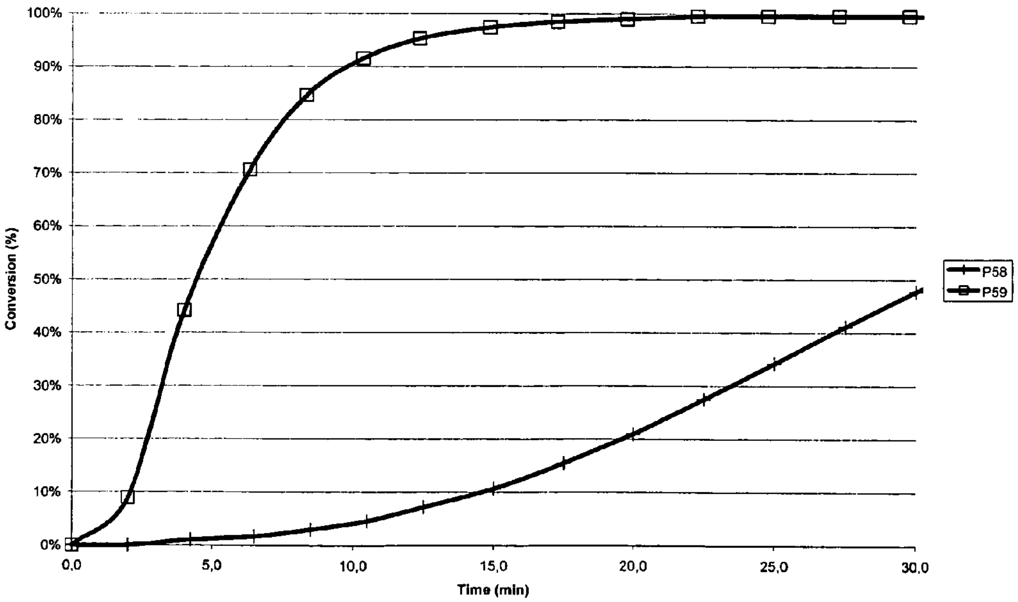

FIG. 6 is a graph showing the conversion rate over time of the product P60 into the product P61 by metathesis reaction and in the presence of catalysts P58 and P59 according to the present invention. The conversion rate of P60 to P61 reflects high catalytic activity of the compounds of the present invention. Here again it can be observed how the catalytic activity is controlled by designing side chain R1.

Furthermore, comparative tests between compounds of general formula 1 and prior art catalysts were performed. Prior art catalysts that were used for the tests are defined by following formulae:

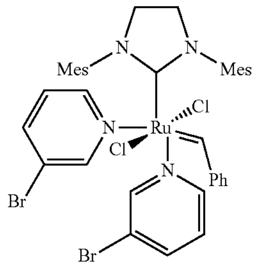

Grubbs III

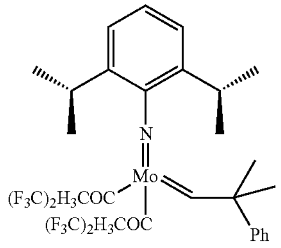

Schrock catalysts

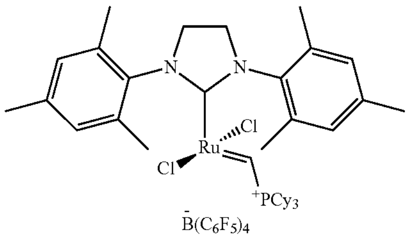

Piers-Grubbs II

-continued

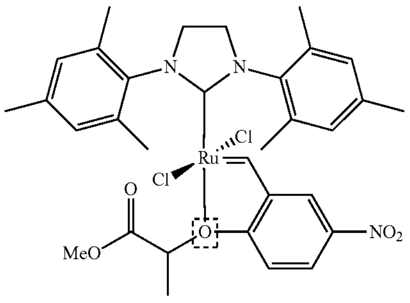

Compound G

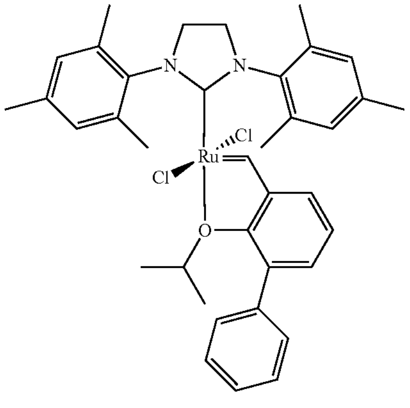

Blechert

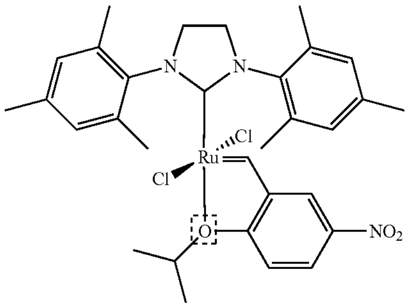

Grela

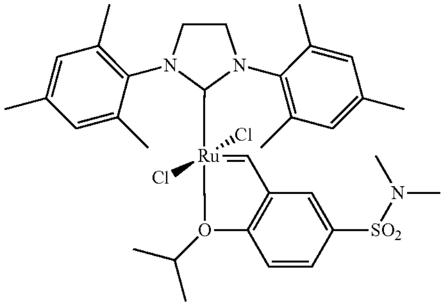

Zannan

-continued

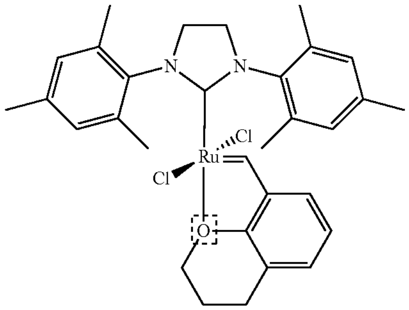

Compound I

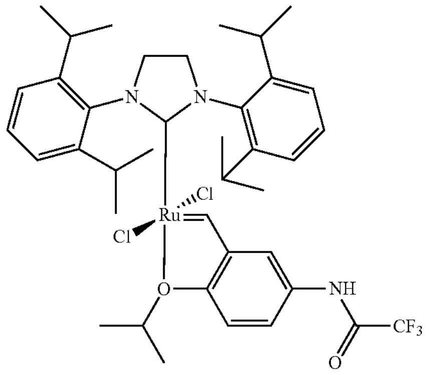

Umicore M71 SIPr

Figure 7:
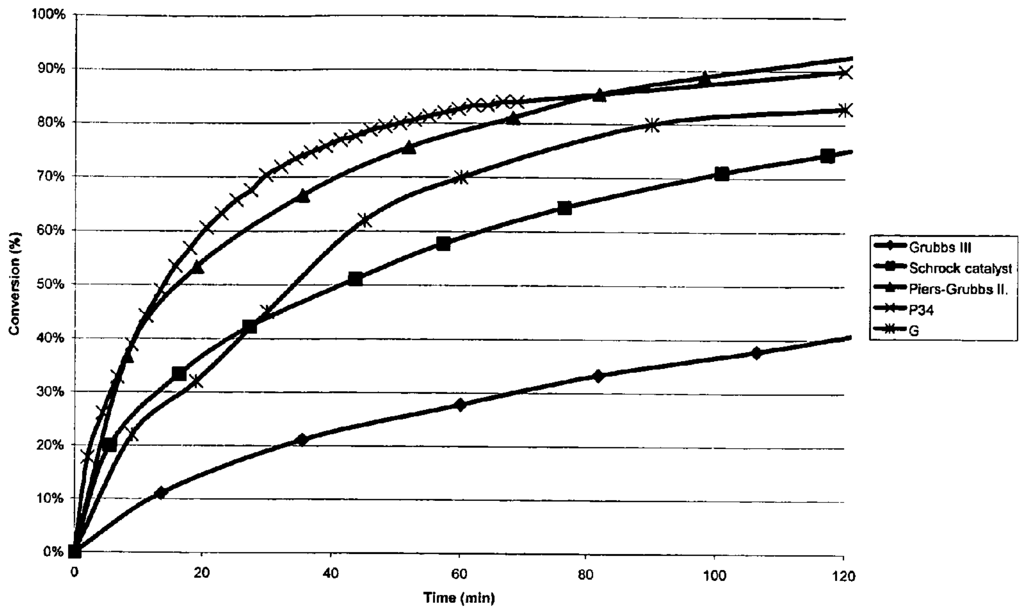

FIG. 7 is a graph showing the conversion rate over time of a product P62 into a product P63 by metathesis reaction and in the presence of four different prior art catalysts (Grubbs III; Schrock catalyst; Piers-Grubbs II; and compound of formula G) in comparison with catalyst P34 according to the present invention.

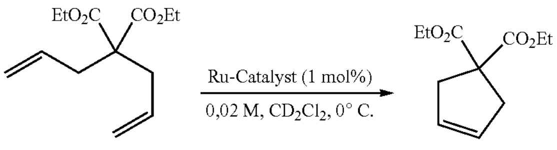

P62 P63

In FIG. 7, it is clearly shown that the compound P34 shows higher catalytic activity than the catalysts of the prior art. However, it should be reminded that when desired the catalytic activity can be reduced in selecting appropriate side chains.

Figure 8:
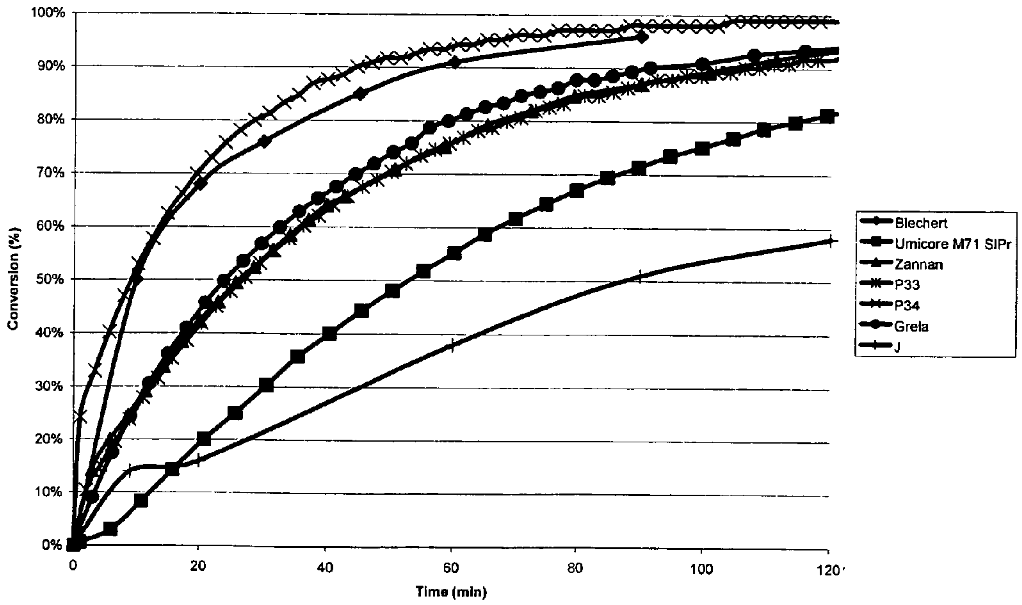

FIG. 8 is a graph showing the conversion rate over time of a product P64 into a product P65 by metathesis reaction and in the presence of three different prior art catalysts (Blechert; Umicore M71 SIPr of formula D; Grela of formula B—*J. AM. CHEM. SOC.* 2006, 128, 13652-13653; Zannan of formula C; and compound of formula I) in comparison with catalysts P33 and P34 according to the present invention.

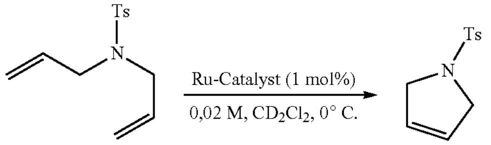

P64 P65

As can be seen on FIG. 8, catalysts of the present invention can be designed to either show a higher catalytic activity than prior art catalysts, or can be designed to show similar activity than prior art catalysts.

In general it can be noted that the compounds of the present invention according to general formula 1 show high catalytic activity. This activity can be enhanced or allayed when alternating the side chains of general formula 1.

Further to the above kinetic studies, stability studies were performed.

Figure 9:
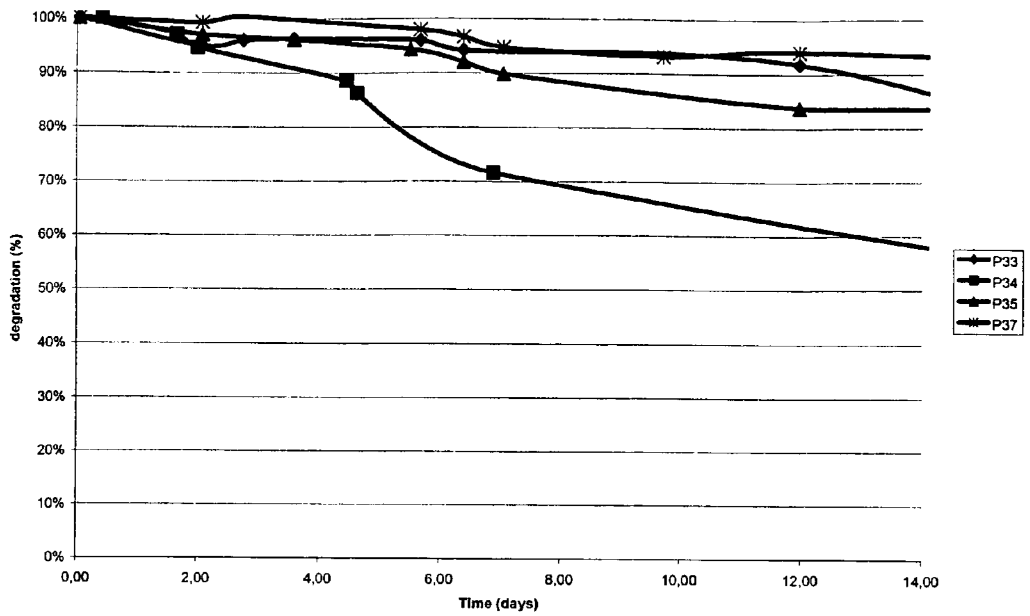
Figure 10:
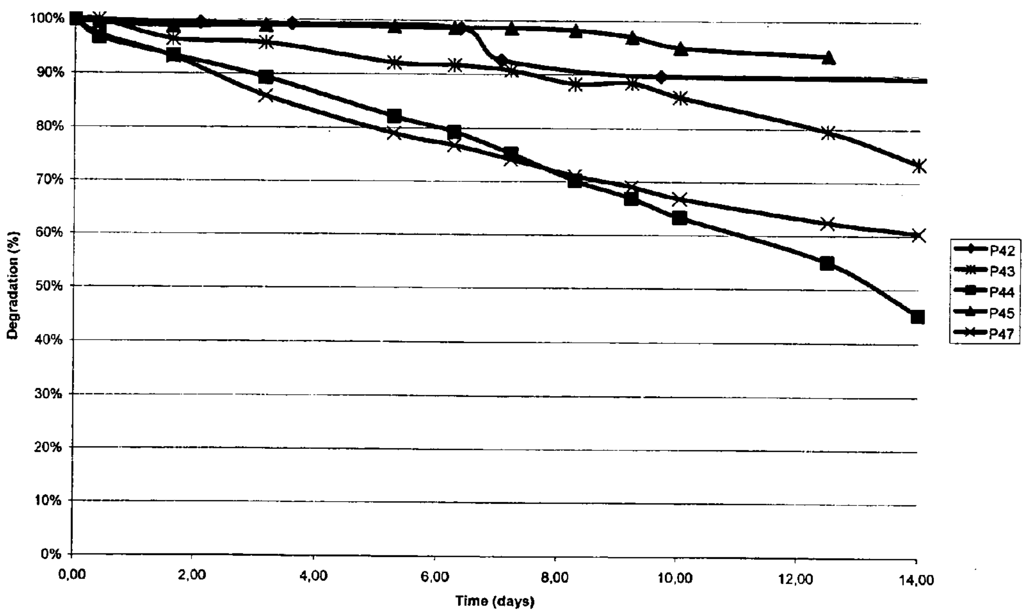
Figure 11:
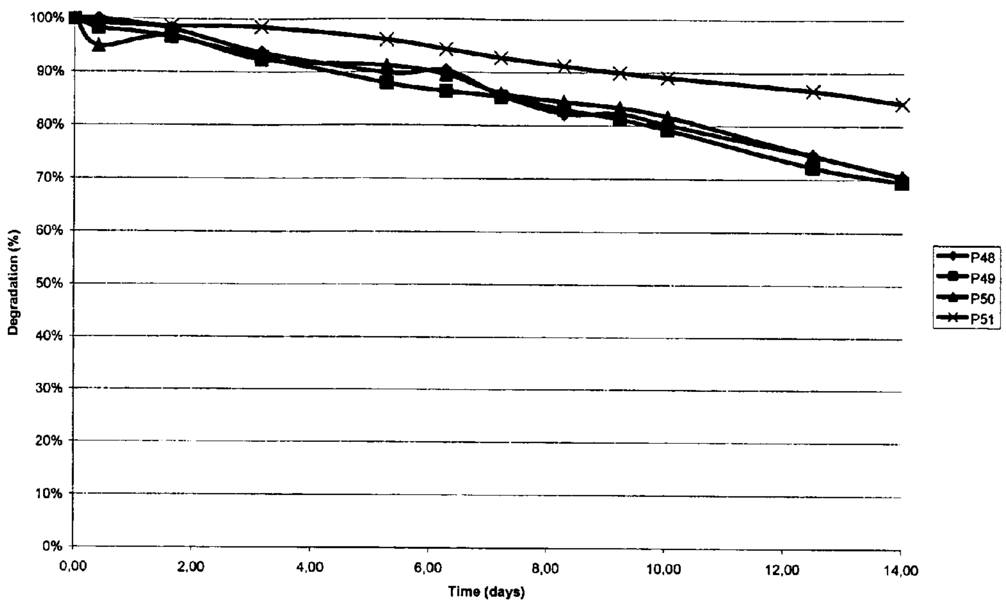
Figure 12:
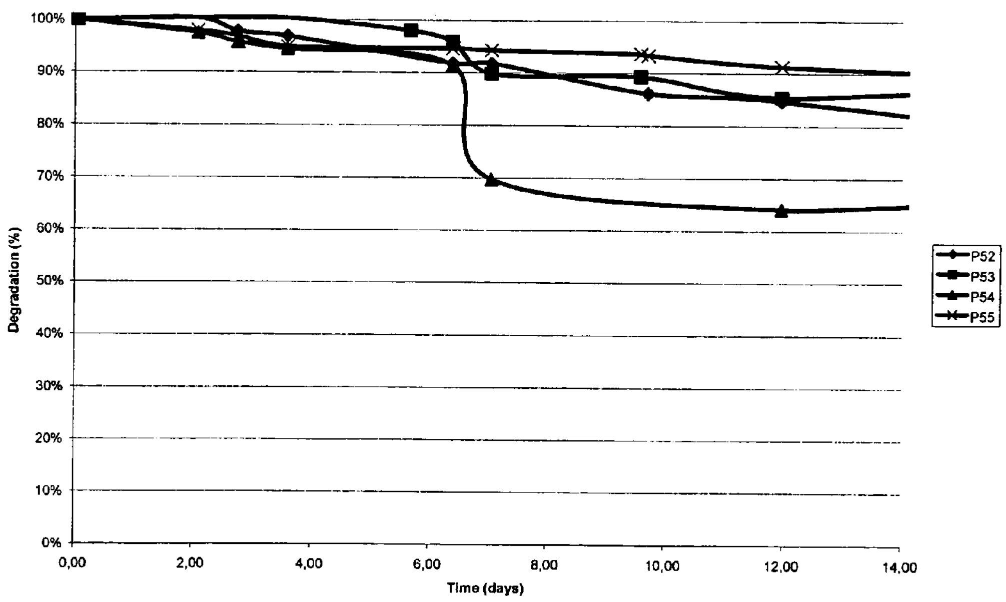

Metathesis catalysts according to the present invention were added to a solution of anthracene (1 eq) in $CD_2Cl_2$ (500 μL) in NMR tube. Tubes were sealed with paraffin. Anthracene was used as internal standard. Degradation of catalysts was monitored in NMR by the periodical acquisition of data over 14 days. Comparison between characteristic signals for carbene proton resonances and anthracene were performed and are reproduced in FIGS. 9 to 12. FIG. 9 shows stability of catalysts P33, P34, P35 and P37 according to the present invention. FIG. 10 shows stability over time of catalysts P42, P43, P44, P45 and P47 according to the present invention; FIG. 11 shows the stability of P48, P49, P50, and P51 according to the present invention; and FIG. 12 shows the stability of catalysts P52, P53, P54 and P55 according to the present invention.

In general it is noted that the compounds of the present invention show great stability.

In the present invention the applicant identified a new backbone (or core) for metathesis catalysts. The compounds of the present invention show high catalytic activity and stability. Furthermore, three different activation sites within the new chelating benzylidene ligand were identified. These activation sites allow efficient and specific control of the catalytic activity of the ruthenium complexes in olefin metathesis transformation. Particularly, R2 and R3 show efficient control of the catalysts activity as can be seen in the non-limitative examples of the present specification.

The invention claimed is:

1. A compound of formula 1, (1)

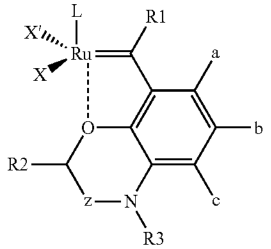

wherein,

X and X' are anionic ligands;

L is an uncharged ligand;

z is a methylene or a carbonyl group;

each of a, b and c is independently H, $NO_2$ or a substituted or unsubstituted, charged or uncharged hydrocarbon group comprising up to 20 carbon atoms or a heteroatom-containing hydrocarbon group comprising up to 20 carbon atoms and one or more heteroatoms;

each of R1, R2 and R3 is independently H or a substituted or unsubstituted, charged or uncharged hydrocarbon group comprising up to 20 carbon atoms or a heteroatom-containing hydrocarbon group comprising up to 20 carbon atoms and optionally comprising one or more heteroatoms.

2. The compound of claim 1, wherein each of X and X' is a halogen.

3. The compound of claim 1, wherein each of a, b and c is independently selected from the group consisting of H; —$NO_2$; $C_{1-12}$-alkyls; $C_{5-12}$-cycloalkyls; $C_{1-12}$-alkoxys; cyano; aryls; heteroaryls, phenyl radicals optionally substituted by a radical selected from the group consisting of $C_{1-6}$-alkyls and $C_{1-6}$-alkoxys; monohalogenated and polyhalogenated aryl radicals and hetero-aryl radicals; monohalogenated and polyhalogenated $C_{1-6}$-alkyl radicals; monohalogenated and polyhalogenated $C_{l-6}$-alkyl-substituted aryl radicals; $C_{1-6}$-alkylcarbonyl radicals; monohalogenated and polyhalogenated $C_{1-6}$-alkylcarbonyl radicals; $C_{1-6}$-alkoxycarbonyl radicals; monohalogenated and polyhalogenated $C_{1-6}$-alkoxycarbonyl radicals; arylcarbonyl radicals; monohalogenated and polyhalogenated arylcarbonyl radicals; aryloxycarbonyl radicals; monohalogenated and polyhalogenated aryloxycarbonyl radicals; —(C═O)—N$(R^a)_2$ radicals wherein $R^a$ is a $C_{1-6}$-alkyl or aryl radical; —NH—(C═O)—$R^a$ radicals wherein $R^a$ is a $C_{1-6}$-alkyl or aryl radical; $C_{1-6}$-alkylsulfonyl radicals; $C_{1-6}$-alkylsulfinyl radicals; —P(═O)$(R^a)_2$ radicals wherein $R^a$ is a $C_{1-6}$alkyl or aryl radical; —NH—$SO_2$—$R^a$ radicals wherein $R^a$ is a $C_{1-6}$-alkyl or aryl radical; $(SO_2)NR^a_2$ radicals wherein $R^a$ is a $C_{1-6}$-alkyl or a aryl radical; and P(═O)($OR^a$)($R^a$) radicals wherein $R^a$ is a $C_{1-6}$-alkyl or aryl radical.

4. The compound of claim 1 wherein a, b and c are each H.

5. The compound of claim 1 wherein R1 is H, a $C_{2-12}$-alkenyl, a $C_{2-12}$-alkynyl or an aryl.

6. The compound of claim 1 wherein R1 is H.

7. The compound of claim 1 wherein R2 is H, a $C_{1-12}$-alkyl, a $C_{5-12}$-cycloalkyl, a $C_{7-18}$-aralkyl or an aryl.

8. The compound of claim 1 wherein R2 is a methyl-, ethyl- or isopropyl-group.

9. The compound of claim 1, wherein R3 is selected from the group consisting of H, $C_{1-12}$-alkyls, $C_{5-12}$-cycloalkyls, $C_{7-18}$-aralkyls, aryls, $C_{1-12}$-halogeno-alkyls, $C_{1-12}$-ammonium-alkyls, $C_{1-12}$-pyridinum-alkyls, $C_{1-12}$-aldehyde-alkyls, $C_{1-12}$-nitro-alkyls, nitriles, and radicals selected from the group consisting of ketones COR4, esters $CO_2$R4, oxalates $COCO_2$R4, sulfones $SO_2$R4 and amides CONHR4 wherein, R4 is selected from the group consisting of H, $C_{1-12}$-alkyls, $C_{5-12}$-cycloalkyls, $C_{7-18}$-aralkyls, aryls, $C_{1-12}$-halogeno-alkyls, $C_{1-12}$-ammonium-alkyls, $C_{1-12}$-pyridinum-alkyls, $C_{1-12}$-aldehyde-alkyls, $C_{1-12}$-nitro-alkyls, and nitriles.

10. The compound of claim 1, wherein, z is methylene, and

R3 is of the formula $R3^a$ or $R3^b$:

-continued $(R3^{a}$

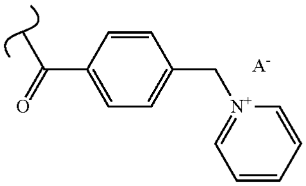

$(R3^{b}$

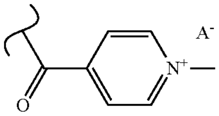

wherein $A^-$ is selected from the group consisting of $F^-$, $Cl^-$, $Br^-$, $I^-$, tetrafluoroborate $BF_4^-$, hexafluorophosphate $PF_6^-$ and bis(trifluoromethylsulfonyl)amide $NTf_2^-$.

11. The compound of claim 1, wherein,

R3 is of the formula $R3^c$, $R3^d$, $R3^e$, $R3^f$, $R3^g$, $R3^h$, $R3^i$, $R3^j$, $R3^k$, $R3^l$, $R3^m$, $R3^n$, $R3^o$ or $R3^p$:

$(R3^{c})$

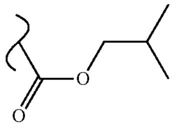

$(R3^{d})$

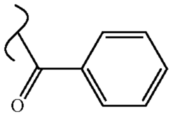

$(R3^{e})$

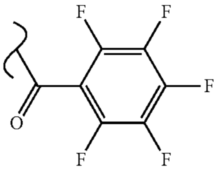

$(R3^{f})$

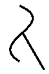

$(R3^{g})$

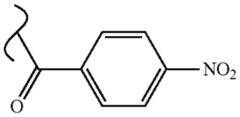

$(R3^{h})$

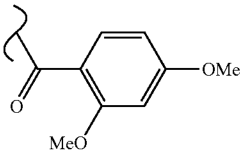

$(R3^{i})$

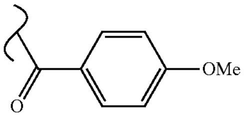

$(R3^{j})$

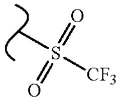

$(R3^{k})$

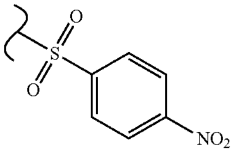

$(R3^{l})$

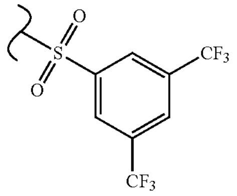

$(R3^{m})$

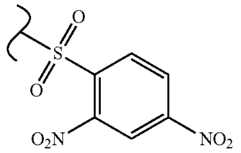

$(R3^{n})$

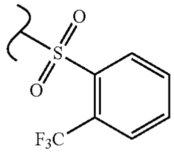

$(R3^{o})$

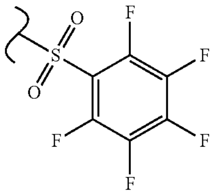

$(R3^{p})$

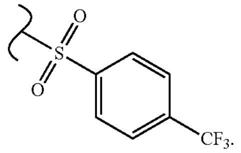

12. The compound of claim 1, wherein L is a phosphine $P(R8)_3$ or a phosphate $P(OR9)_3$ wherein R8 and R9 are each independently a $C_{1-6}$-alkyl, a $C_{5-12}$-cycloalkyl or an aryl.

13. The compound of claim 1, wherein L is a ligand of the formula L1, L2, L3 or L4:

(L1)

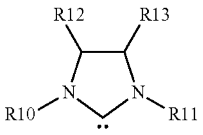

-continued (L2)

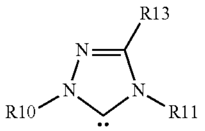

(L3)

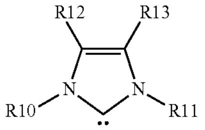

(L4)

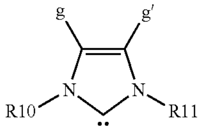

wherein R10 and R11 are each independently a substituted or an unsubstituted hydrocarbon comprising 1 to 30 carbon atoms, and R12 and R13 are each independently H, a $C_{1-6}$-alkyl optionally substituted by a alkoxy radical OR15, or aryl optionally substituted by a alkoxy radical OR15, or form a 3- or 4-membered alkylene bridge, wherein R15 is selected from the group consisting of $C_{1-20}$-alkyls, aryls and $C_{7-18}$-aralkyls, and g and g' are each a halogen.

14. The compound of claim 13, wherein R10 and R11 are each independently a $C_{1-30}$-alkyl optionally substituted by an alkoxy radical OR15, a $C_{2-30}$-alkenyl optionally substituted by an alkoxy radical OR15, aryl optionally substituted by an alkoxy radical OR15, an aminoalkyl or an aminocycloalkyl.

15. The compound claim 1, wherein L is a ligand of the formula $L1^a$, $L1^b$, $L1^c$, $L1^d$, $L1^e$, $L1^f$ or $L1^g$:

($L1^a$)

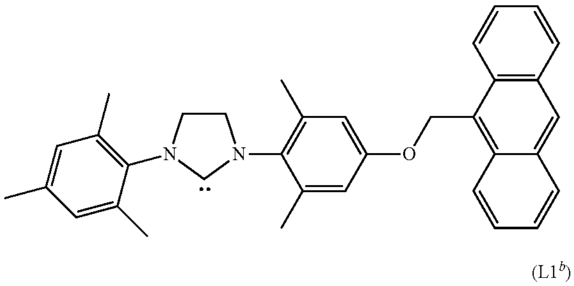

($L1^b$)

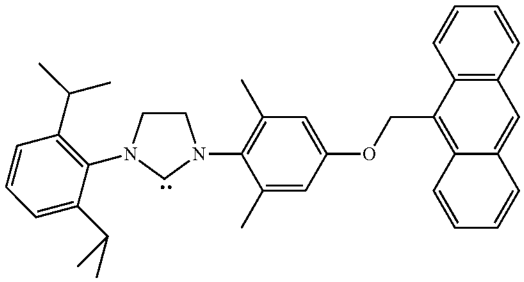

-continued ($L1^c$)

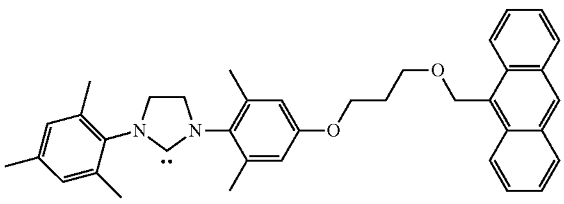

($L1^d$)

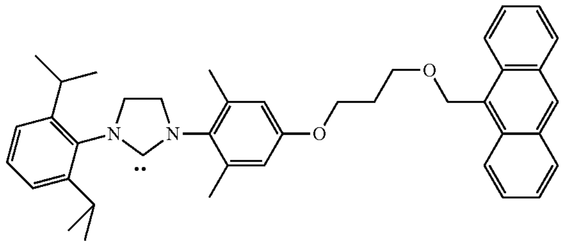

($L1^e$)

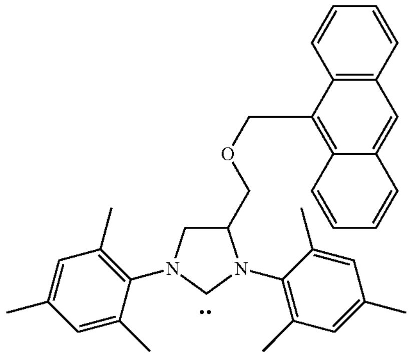

($L1^f$)

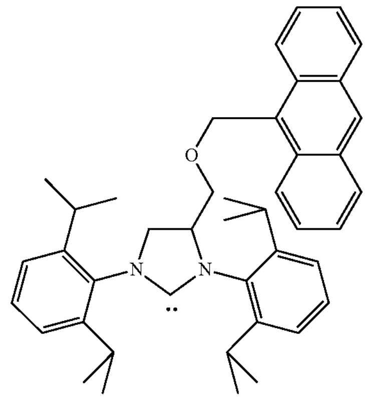

($L1^g$)

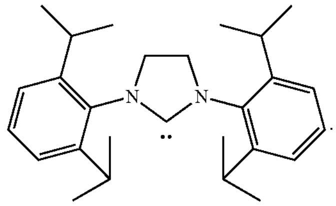

16. A method comprising contacting one or more chemical reactants with a catalyst comprising the compound of claim 1 to promote a chemical reaction of the reactants.

17. The method of claim 16 wherein said chemical reaction is a metathesis reaction.

18. A method of preparing the compound of claim 1 comprising reacting a compound of formula (2)

(2)

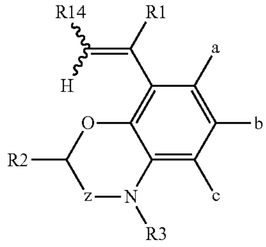

with a ruthenium complex of formula (3)

(3)

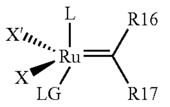

wherein,

LG is a leaving group

R14 is H or a $C_{1-12}$-alkyl, each of R16 and R17 is independently H, a $C_{1-6}$-alkyl, optionally substituted by one or more halogens, or an aryl, optionally substituted by one or more halogens or by a $C_{1-6}$-alkyl; or R16 and R17 together form a 5- to 12-membered aliphatic and/or aromatic ring system, optionally substituted by one or more halogens, a $C_{1-6}$-alkyl or by an aryl.

19. The method of claim 18, wherein each of X and X' is a halogen.

20. The method of claim 18, wherein each of a, b and c is independently selected from the group consisting of H; —$NO_2$; $C_{1-12}$-alkyls; $C_{5-12}$-cycloalkyls; $C_{1-12}$-alkoxys; cyano; aryls; heteroaryls; phenyl optionally substituted by a radical selected from the group consisting of $C_{1-6}$-alkyls and $C_{1-6}$-alkoxys; monohalogenated and polyhalogenated aryl radicals and hetero-aryl radicals; monohalogenated and polyhalogenated $C_{1-6}$-alkyl radicals; monohalogenated and polyhalogenated $C_{1-6}$-alkyl-substituted aryl radicals; $C_{1-6}$-alkylcarbonyl radicals; monohalogenated and polyhalogenated $C_{1-6}$-alkylcarbonyl radicals; $C_{1-6}$-alkoxycarbonyl radicals; monohalogenated and polyhalogenated $C_{1-6}$-alkoxycarbonyl radicals; arylcarbonyl radicals; monohalogenated and polyhalogenated arylcarbonyl radicals; aryloxycarbonyl radicals; monohalogenated and polyhalogenated aryloxycarbonyl radicals; —(C═O)—N$(R^a)_2$ radicals wherein $R^a$ is a $C_{1-6}$-alkyl or aryl radical; —NH—(C═O)—$R^a$ radicals wherein $R^a$ is a $C_{1-6}$-alkyl or aryl radical; $C_{1-6}$-alkylsulfonyl radicals; $C_{1-6}$-alkylsulfinyl radicals; —P(═O)$(R^a)_2$ radicals wherein $R^a$ is a $C_{1-6}$ -alkyl or aryl radical; —NH—$SO_2$—$R^a$ radicals wherein $R^a$ is a $C_{1-6}$-alkyl or aryl radical; $(SO_2)NR_2{}^a$ radicals wherein $R^a$ is a $C_{1-6}$-alkyl or aryl radical; and P(═O)$(OR^a)$ $(R^a)$ radicals wherein $R^a$ is a $C_{1-6}$-alkyl or aryl radical.

21. The method of claim 18, wherein a, b and c are each H.

22. The method of claim 18, wherein R1 is H, a $C_{2-12}$-alkenyl, a $C_{2-12}$-alkynyl or an aryl.

23. The method of claim 18, wherein R1 is H.

24. The method of claim 18, wherein R2 is H, a $C_{1-12}$-alkyl, a $C_{5-12}$cycloalkyl, a $C_{7-18}$-aralkyl or an aryl.

25. The method of claim 18, wherein R2 is a methyl-, ethyl- or isopropyl-group.

26. The method of claim 18, wherein R3 is selected from the group consisting of H, $C_{1-12}$-alkyls, $C_{5-12}$-cycloalkyls, $C_{7-8}$-aralkyls, aryls, $C_{1-12}$-halogeno-alkyls, $C_{1-12}$-ammonium-alkyls, $C_{1-12}$-pyridinum-alkyls, $C_{1-12}$-aldehyde-alkyls, $C_{1-12}$-nitro alkyls, nitriles, and radicals selected from the group consisting of ketones COR4, esters $CO_2R4$, oxalates $COCO_2R4$, sulfones $SO_2R4$ and amides CONHR4 wherein, R4 is selected from the group consisting of H, $C_{1-12}$-alkyls, $C_{5-12}$-cycloalkyls, $C_{7-18}$-aralkyls, aryl, $C_{1-12}$ -halogeno-alkyls, $C_{1-12}$-ammonium-alkyls, $C_{1-12}$-pyridinum-alkyls, $C_{1-12}$-aldehyde-alkyls, $C_{1-12}$-nitro-alkyls, and nitriles.

27. The method of claim 18, wherein, z is methylene, and

R3 is of the formula $R3^a$ or $R3^b$:

($R3^a$

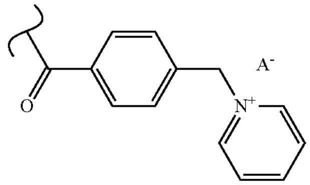

($R3^b$

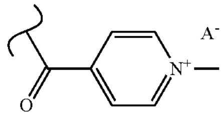

wherein $A^-$ is selected from the group consisting of $F^-$, $Cl^-Br^-$, $I^-$, tetrafluoroborate $BF_4{}^-$, hexafluorophosphate $PF_6{}^-$ and bis(trifluoromethylsulfonyl)amide $NTf_2{}^-$.

28. The method of claim 18, wherein, R3 is of the formula $R3^c$, $R3^d$, $R3^e$, $R3^f$, $R3^g$, $R3^h$, $R3^i$, $R3^j$, $R3^k$, $R3^l$, $R3^m$, $R3^n$, $R3^o$ or $R3^p$:

($R3^c$)

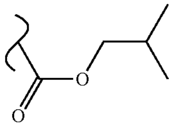

($R3^d$)

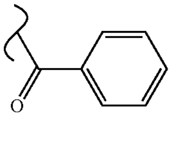

($R3^e$)

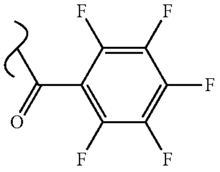

($R3^f$)

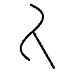

-continued (R3[g])

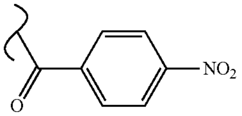

(R3[h])

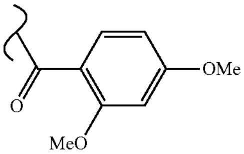

(R3[i])

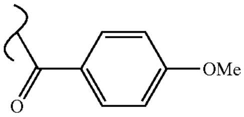

(R3[j])

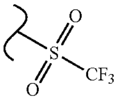

(R3[k])

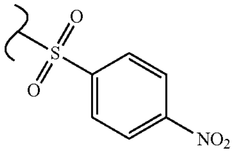

(R3[l])

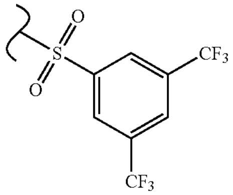

(R3[m])

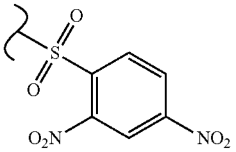

(R3[n])

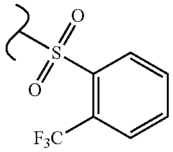

(R3[o])

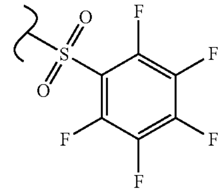

-continued (R3[p])

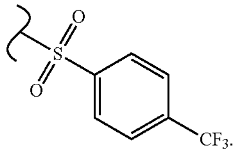

29. The method of claim 18, wherein L is a phosphine $P(R8)_3$ or a phosphate $P(OR9)_3$ and R8 and R9 are each independently a $C_{1-6}$-alkyl, a $C_{5-12}$-cycloalkyl or an aryl.

30. The method of claim 18, wherein L is a ligand of the formula L1, L2, L3 or L4:

(L1)

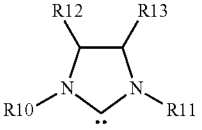

(L2)

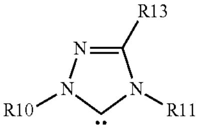

(L3)

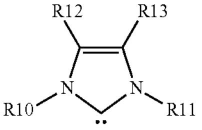

(L4)

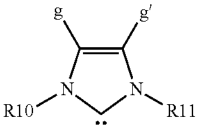

wherein R10 and R11 are each independently a substituted or an unsubstituted hydrocarbon comprising 1 to 30 carbon atoms, and wherein R12 and R13 are each independently H, a $C_{1-6}$-alkyl optionally substituted by a alkoxy radical OR15, or aryl optionally substituted by a alkoxy radical OR15, or form a 3- or 4-membered alkylene bridge, wherein R15 is selected from the group consisting of $C_{1-20}$-alkyls, aryl and $C_{7-18}$-aralkyls, and g and g' are each a halogen.

31. The method of claim 30, wherein R10 and R11 are each independently a $C_{1-30}$-alkyl optionally substituted by a alkoxy radical OR15, a $C_{2-30}$-alkenyl optionally substituted by a alkoxy radical OR15, an aryl optionally substituted by a alkoxy radical OR15, an aminoalkyl or an aminocycloalkyl.

32. The method of claim 18, wherein L is a ligand of the formula $L1^a$, $L1^b$, $L1^c$, $L1^d$, $L1^e$, $L1^f$ or $L1^g$:

-continued (L1a)

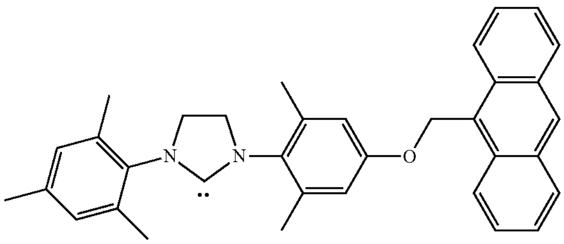

(L1b)

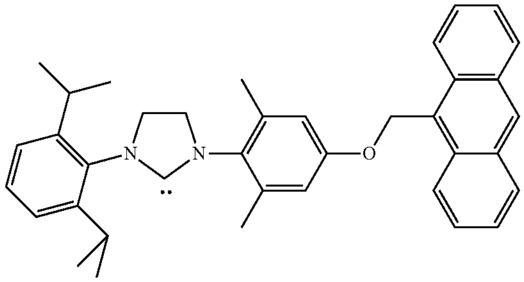

(L1c)

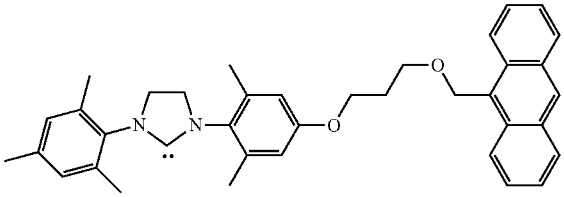

(L1d)

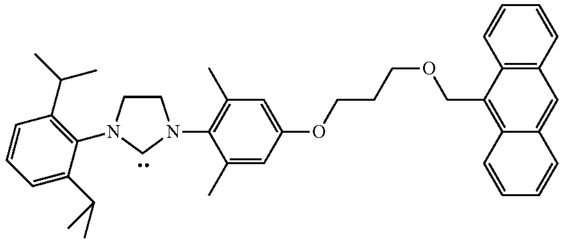

(L1e)

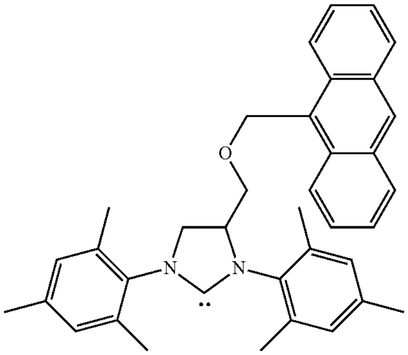

(L1f)

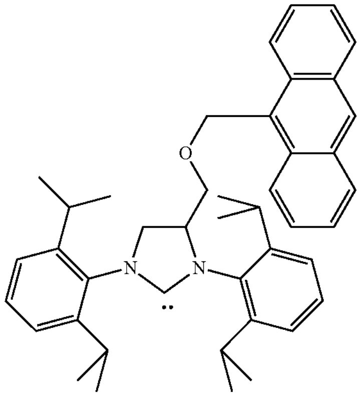

(L1g)

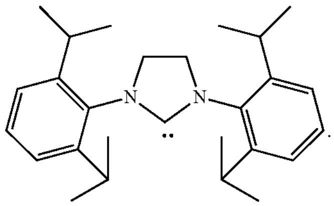

33. The compound of claim 1 wherein each of X and $X^1$ is independently Cl or Br.

34. The compound of claim 13 wherein each of g and $g^1$ is independently Cl or Br.

35. The method of claim 17 wherein the metathesis reaction is a ring-closing metathesis (RCM) reaction, a cross-metathesis (CM) reaction, or a ring-opening metathesis polymerization (ROMP) reaction.

36. The method of claim 18 wherein

LG is a phosphine $P(R8)_3$ where R8 is selected from the group consisting of $C_{1-6}$-alkyls; $C_{5-12}$-cycloalkyls; and aryls;

R14 is H or a $C_{1-12}$-alkyl; and

R16 and R17 are each independently H, a $C_{1-6}$-alkyl optionally substituted with one or more halogens, an aryl, optionally substituted with one or more halogens or a $C_{1-6}$-alkyl; or R16 and R17 together form a 5- to 12-membered aliphatic or aromatic ring system, optionally substituted with one or more halogens, a $C_{1-6}$-alkyl or an aryl.

37. The method of claim 18 wherein

LG is a pyridine or a pyridine substituted with a charged or uncharged hydrocarbon group comprising up to 20 carbon atoms, R14 is a methyl group; and R16 and R17 together form an indenylidene system.

38. The method of claim 19 wherein each of X and $X^1$ is independently Cl or Br.

39. The method of claim 30 wherein each of g and $g^1$ is independently Cl or Br.

40. A compound of formula 1, (1)

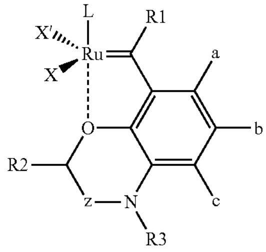

wherein, each of X and X' is a an anionic ligand independently selected from the group consisting of halogens;

z is a methylene or a carbonyl group;

each of a, b and c is independently selected from the group consisting of H; —$NO_2$; $C_{1-12}$-alkyls; $C_{5-12}$-cycloalkyls; $C_{1-12}$-alkoxys; cyano; aryls; heteroaryls, phenyl radicals optionally substituted by a radical selected from the group consisting of $C_{1-6}$-alkyls and $C_{1-6}$-alkoxys; monohalogenated and polyhalogenated aryl radicals and hetero-aryl radicals; monohalogenated and polyhalogenated $C_{1-6}$-alkyl radicals; monohalogenated and polyhalogenated $C_{1-6}$-alkyl-substituted aryl radicals; $C_{1-6}$-alkylcarbonyl radicals; monohalogenated and polyhalogenated $C_{1-6}$-alkylcarbonyl radicals; $C_{1-6}$-alkoxycarbonyl radicals; monohalogenated and polyhalogenated $C_{1-6}$-alkoxycarbonyl radicals; arylcarbonyl radicals; monohalogenated and polyhalogenated arylcarbonyl radicals; aryloxycarbonyl radicals; monohalogenated and polyhalogenated aryloxycarbonyl radicals; —(C═O)—$N(R^a)_2$ radicals wherein $R^a$ is a $C_{1-6}$-alkyl or aryl radical; —NH—(C═O)—$R^a$ radicals wherein $R^a$ is a $C_{1-6}$-alkyl or aryl radical; $C_{1-6}$-alkylsulfonyl radicals; $C_{1-6}$-alkylsulfinyl radicals; —P(═O)$(R^a)_2$ radicals wherein $R^a$ is a $C_{1-6}$-alkyl or aryl radical; —NH—$SO_2$—$R^a$ radicals wherein $R^a$ is a $C_{1-6}$-alkyl or aryl radical; $(SO_2)NR_2^a$ radicals wherein $R^a$ is a $C_{1-6}$-alkyl or aryl radical; and P(═O)$(OR^a)(R^a)$ radicals wherein $R^a$ is a $C_{1-6}$-alkyl or aryl radical;

R1 is selected from the group consisting of H, $C_{2-12}$-alkenyls, $C_{2-12}$-alkynyls, and aryls;

R2 is selected from the group consisting of H, $C_{1-12}$-alkyls, $C_{5-12}$-cycloalkyls, $C_{7-18}$-aralkyls, and aryls; and R3 is selected from the group consisting of H, $C_{1-12}$-alkyls, $C_{5-12}$-cycloalkyls, $C_{7-18}$-aralkyls, aryls, $C_{1-12}$-halogeno-alkyls, $C_{1-12}$-ammonium-alkyls, $C_{1-12}$-pyridinum-alkyls, $C_{1-12}$-aldehyde-alkyls, $C_{1-12}$-nitro-alkyls, nitriles, ketone radicals of the form COR4, ester radicals of the form $CO_2R4$, oxalate radicals of the form $COCO_2R4$, sulfone radicals of the form $SO_2R4$ and amide radicals of the form CONHR4 where R4 is selected from the group consisting of H, $C_{1-12}$-alkyls, $C_{5-12}$-cycloalkyls, $C_{7-8}$-aralkyls, aryls, $C_{1-12}$-halogeno-alkyls, $C_{1-12}$-ammonium-alkyls, $C_{1-12}$-pyridinum-alkyls, $C_{1-12}$-aldehyde-alkyls, $C_{1-12}$-nitro-alkyls, and nitriles; and L is an uncharged ligand selected from the group consisting of phosphines $P(R8)_3$ and phosphates $P(OR9)_3$ where each R8 and R9 is independently selected from the group consisting of $C_{1-6}$-alkyls, $C_{5-12}$-cycloalkyls and $C_{5-12}$-aryls, and ligands of the formula L1, L2, L3 or L4:

(L1)

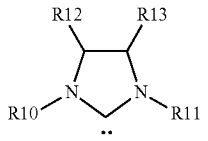

(L2)

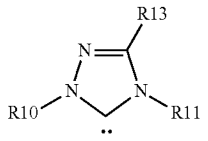

(L3)

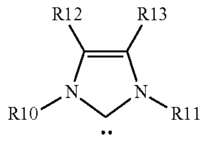

(L4)

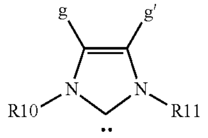

wherein R10 and R11 are each independently a $C_{1-30}$-alkyl optionally substituted by an alkoxy radical OR15, a $C_{2-30}$-alkenyl optionally substituted by an alkoxy radical OR15, aryl optionally substituted by an alkoxy radical OR15, an aminoalkyl or an aminocycloalkyl, R12 and R13 are each independently H, a $C_{1-6}$-alkyl optionally substituted by a alkoxy radical OR15, or aryl optionally substituted by a alkoxy radical OR15, or form a 3- or 4-membered alkylene bridge, R15 is selected from the group consisting of $C_{1-20}$-alkyls, aryls, and $C_{7-18}$-aralkyls, and g and g' are each a halogen.

* * * * *